United States Patent
Schleef

(10) Patent No.: US 9,382,552 B2
(45) Date of Patent: Jul. 5, 2016

(54) MINICIRCLES WITH VIRAL EXPRESSION CASSETTES AND THEIR USE IN THE TRANSFORMATION OF CELLS FOR GENERATING RECOMBINANT VIRUS OR VIRAL GENE VECTORS

(71) Applicant: PLASMIDFACTORY GMBH & CO. KG, Bielefeld (DE)

(72) Inventor: Martin Schleef, Bielefeld (DE)

(73) Assignee: PlasmidFactory GmbH + Co KG, Bielefeld (DE)

( * ) Notice: Subject to any disclaimer, the term of this patent is extended or adjusted under 35 U.S.C. 154(b) by 0 days.

(21) Appl. No.: 14/514,606

(22) Filed: Oct. 15, 2014

(65) Prior Publication Data

US 2015/0218586 A1    Aug. 6, 2015

(30) Foreign Application Priority Data

Oct. 15, 2013  (DE) .......................... 10 2013 220 859

(51) Int. Cl.
  *C12N 15/63*    (2006.01)
  *C12N 15/86*    (2006.01)
(52) U.S. Cl.
  CPC ...... *C12N 15/86* (2013.01); *C12N 2740/10052* (2013.01); *C12N 2750/00043* (2013.01); *C12N 2750/14152* (2013.01); *C12N 2770/00043* (2013.01); *C12N 2800/107* (2013.01); *C12N 2800/30* (2013.01); *C12N 2800/40* (2013.01); *C12N 2800/50* (2013.01)
(58) Field of Classification Search
  None
  See application file for complete search history.

(56) References Cited

FOREIGN PATENT DOCUMENTS

| DE | 10 2011 118 018 A1 | 4/2013 |
|---|---|---|
| EP | 0 350 341 B1 | 1/1990 |
| EP | 1 505 089 B1 | 1/2006 |
| EP | 1 620 559 B1 | 3/2010 |
| WO | 03/016521 A2 | 2/2003 |

OTHER PUBLICATIONS

Ayuso et al., "Production, Purification and Characterization of Adeno-Associated Vectors", Current Gene Therapy 2010; 10(6): 423-436.
Bigger et al., "An araC-controlled Bacterialcre Expression System to Produce DNA Minicircle Vectors for Nuclear and Mitochondrial Gene Therapy", J. Biol Chem 2001, 276: 23018-23027.
Chadeuf et al., "Evidence for encapsidation of prokaryotic sequences during recombinant adenoassociated virus production and their in vivo persistence after vector delivery", Mol. Ther. 2005; 12: 744-53.
Chen et al. "Minicircle DNA Vectors Devoid of Bacterial DNA Result in Persistent and High-Level Transgene Expression in Vivo", Mol. Ther. 2003; 8: 495-500.
A.M. Darquet et al., "A new DNA vehicle for nonviral gene delivery: supercoiled minicircle" Gene Ther. 1997; 4: 1341-1349.
A.M. Darquet et al., "Minicircle: an improved DNA molecule for in vitro and in vivo gene transfer." Gene Ther. 1999; 6: 209-218.
Z. Wang et al., "Rapid and highly efficient transduction by double-stranded adeno-associated virus vectors in vitro and in vivo", Gene Therapy, 2003; 10(26): 2105-2111.
Grimm et al., "Novel Tools for Production and Purification of Recombinant Adenoassociated Virus Vectors", Hum. Gene Therapy 1998; 9: 2745-60.
Haase et al., "pEPito: a significantly improved non-viral episomal expression vector for mammalian cells" BMC Biotechnol., 2010; 10:20.
Heilbronn and Weger, "Viral Vectors for Gene Transfer: Current Status of Gene Therapeutics" Handbook Exp. Pharmacol. 2010; 197: 143-70.
Kern et al., "Identification of a Heparin-Binding Motif on Adeno-Associated Virus Type 2 Capsid" J. Virol. 2003; 77: 11072-81.
Kreiss et al., "Production of a new DNA vehicle for gene transfer using site-specific recombination" Appl Microbiol Biotechnol. 1998; 49: 560-567.
Mayrhofer et al., "Minicircle-DNA production by site specific recombination and protein—DNA interaction chromatography", J. Gene Med., 2008; 10(11): 1253-1269.
DM McCarty et al., "Adeno-associated virus terminal repeat (TR) mutant generates self-complementary vectors to overcome the rate-limiting step to transduction in vivo" Gene Therapy, 2003; 10(26): 2112-2118.
Moullier and Snyder, "International Efforts for Recombinant Adeno-associated Viral Vector Reference Standards", Mol. Ther. 2008; 16: 1185-1188.
JE Rabinowitz et al., "Cross-Packaging of a Single Adeno-Associated Virus (AAV) Type 2 Vector Genome into Multiple AAV Serotypes Enables Transduction with Broad Specificity" J. Virol. 2002; 76:791-801.
DW Russell, PC Hendrie, "Gene Targeting with Viral Vectors", Molecular Therapy, 2005; 12: 9-17.

*Primary Examiner* — Celine Qian
(74) *Attorney, Agent, or Firm* — Stacey J. Farmer; Grund IP Group

(57) ABSTRACT

The invention relates to a minicircle transfer vector for producing viral vectors comprising a transfer sequence and specific packing signals flanking both sides of the transfer sequence for packaging of the transfer sequence into particles of a viral vector. The invention also relates to minicircle packaging vectors carrying support functions for producing viral vectors. The invention further relates to cells bearing the disclosed minicircles. The invention further relates to methods for producing viral vectors using such minicircles and viral vectors obtained thereby, as well as kits useful in performing the described methods.

19 Claims, 9 Drawing Sheets

Sequence of Interest

Sequence of Interest

Sequence of Interest

MINICIRCLES WITH VIRAL EXPRESSION CASSETTES AND THEIR USE IN THE TRANSFORMATION OF CELLS FOR GENERATING RECOMBINANT VIRUS OR VIRAL GENE VECTORS

CROSS-REFERENCE TO RELATED APPLICATIONS

This application claims the benefit of German Patent Application DE 10 2013 220 859.6, filed on Oct. 15, 2013.

TECHNICAL FIELD

The present invention relates to the field of biotechnology. More specifically, the invention relates to providing vectors for the transformation of cells for the production of viral vectors and/or viruses.

BACKGROUND

Conventional methods of gene therapy frequently use plasmid DNA as vectors for introducing desired DNA segments into target cells. In such applications, however, plasmids frequently have certain disadvantages—compared to viral vectors—, of lower transfection efficiency; viral vectors are therefore preferably used.

Until now, about 25% of all gene therapy protocols that have been used in clinical trials are based directly on plasmid DNA vectors (Edelstein et al, *J. Gene Med.* 2007; 9: 833-42). It was initially expected that the market share of plasmid DNA-based vector vaccines would increase to about 60% (Jain, "Vectors for gene therapy: Current status and future prospects", PJB Publications Ltd, London, 1996). This includes plasmid DNA used for the production of viral vectors, e.g. by transient transfection of producer cells for adeno-associated (AAV) vectors, lentiviral (LV) vectors, retroviral (RV) vectors or adenoviral (Ad) vectors. The use of at least one plasmid for the production of viral vectors and viruses, for example, has already been described for AAV (WO 03/016521 A2), but also the distribution in different (at least two, but possibly more) plasmids of the above-mentioned viruses or viral vectors has been described. In such cases, the co-transfection of cells with plasmids is performed.

The AAV packaging/helper system based on two plasmids from the laboratory of Jurgen Kleinschmidt (Grimm et al, *Hum Gene Therapy* 1998; 9: 2745-60) was initially developed for serotypes 1-6. Mutants with e.g. a heparin binding site deficiency (pDG(R484E/r585E), Kern et al, *J. Virol.* 2003; 77: 11072-81) and other, including synthetic, serotypes for co-transfection are available with only the transfer plasmid (containing the ITRs) on the one hand, and with the packaging/helper plasmid (both functions on another plasmid with a size of about 20 kbp), on the other hand. Other versions of such systems have been published (Lock et al., *Hum. Gene Ther.* 21, 1273-1285), and two international reference standards have been applied to ensure adequate clinical preparation of the AAV by using the pDG-plasmid system (Moullier and Snyder, *Mol Ther* 2008, 16: 1185-1188). In such cases, the optimization of transfection is relatively simple, since only the correct ratio of the amounts of both plasmids must be determined when work is resumed using a new batch of the plasmids. This is a far more difficult task when three (or more) plasmids must be triple-transfected and the individual relative amounts of each must therefore be newly optimized when a fresh batch is used. An overview is provided by Ayuso et al. (*Curr Gene Ther* 2010, 10: 423-436).

In wild-type viruses the cotransfection transfer plasmids for AAV production contain the sequences encoding for the replication and envelope proteins (rep and cap) between the ITR sequences. This area including the rep and cap genes was relocated on other plasmids/the other plasmid cotransfection as part of the development of systems for the production of AAV vectors to create on the transfer plasmid a location for the sequences of interest, which are subsequently supposed to find a place in the viral particle. Expression of these sequences will initially be delayed in the conventional viral AAV vectors after their use for infection of a target cell (such as in uses for gene therapy), since the synthesis of the second strand of DNA (the DNA contained in the viral particles is single-stranded) can only be manufactured with the help of the cellular replication system; thus, enabling only the formation of a transcriptionally competent duplex. The development of so-called self-complementary AAV vectors (Heilbron and Weger, *Handb Exp Pharmacol* 2010, 197: 143-70) solves this problem through the use of double-stranded "genomes" in the vectors (ITR-flanked sequences of interest). It has been found that these are available as a double strand in the target cell immediately following vector infection. Such double-stranded viral sequences were obtained by deletion of the "terminal resolution site" in an ITR, and during replication the rep proteins were no longer able to cut this DNA for incorporation into the viral particles. Therefore, the replication proceeded across this modified ITR and resulted—using the newly synthesized strand as a template—in a complementary strand. The resulting DNA strand in the forward portion of the sense strand consisted of the sequence of interest and—not interrupted by the unresolved modified ITR—of the anti-sense strand of the sequence of interest. The generated viral vectors are superior to previous non-self-complementary vectors with respect to their transgene expression (D M McCarty et al, *Gene Ther* 2003, 10 (26): 2112 to 2118; Z. Wang et al, *Gene Ther* 2003, 10 (26): 2105-2111).

After Chadeuf et al. (*Mol Ther* 2005; 12: 744-53) demonstrated that the structural elements of plasmid vectors for the production of AAV particles, namely elements of the transfer plasmid carrying antibiotic resistance genes, were detectable in virus preparations, various regulatory authorities strongly demanded avoiding such sequences in AAV preparations. This recurring problem is also referred to as "retro packaging" and means that individual sequence portions of those plasmids carrying the signal structures for partial packing in viruses or viral vectors (so-called "transfer plasmids", sometimes referred to as "vector plasmids") are incorrectly packed into the viruses or viral vectors. A transfer plasmid contains its regulatory elements (bacterial origin of replication and selection marker) and the sequences of interest to be transferred (e.g. a gene). These sequences of interest are flanked by signal sequences, according to the prior art, e.g. so-called ITRs, or inverted terminal repeats, in AAV; or LTRs, which are long terminal repeats, in LV. However, since an (intact) plasmid is constructed as a circle, the framing of a sequence of interest to the exclusion of origin of replication and/or selection marker means that excluded elements, or at least one thereof (origin of replication and/or selection marker) on the reverse side of the plasmid also are flanked by these signal sequences. Thus, the encoded sequences (also shown for AAV, see Chadeuf et al. 2005) can also be packaged in the viral capsids, albeit at a slower rate, and lead to nonfunctioning or even dangerous viral vectors. These are detectable in preparations of viruses or viral vectors and can also additionally lead to a pharmaceutical threat of a mixture of functional and non-functional viruses or viral vectors—accordingly, with reduced efficiency.

The above situation has led to the development of a minicircle system, as disclosed herein, that avoids the aforementioned problems in the future.

Recently, so-called minicircles (MC), small circular DNA molecules containing a desired expression cassette and a few undesirable prokaryotic sequences, have been used to transfect cells. One method for the production of minicircles is described in WO 96/26270. It was further demonstrated that minicircles offer, apart from improved biosafety due to their small size, improved gene transfer characteristics (A. M. Darquet et al., *Gene Ther.* 1997, 4: 1341-1349; A. M. Darquet et al., *Gene Ther.* 1999, 6: 209-218).

Bigger et al (*J. Biol Chem* 2001, 276: 23018-23027) describe the preparation of minicircles by means of the introduction of plasmids with loxP sites in bacteria, which can express the Cre recombinase. The plasmid further comprises a eukaryotic expression cassette and a marker sequence. After induction of Cre the plasmid is cleaved into miniplasmid and minicircle, wherein the minicircle contains only the expression cassette. In addition, the loxP sites are mutated, so that the reversibility of recombination is reduced.

Other publications also describe the production of minicircles using alternative recombination systems, e.g. Kreiss et al. (*Appl Microbiol Biotechnol* 1998, 49: 560-567) using λ integrase and Chen et al. (*Mol Ther* 2003, 8: 495-500) using ΦC31 integrase. Therefore, minicircles are established as alternative vectors used for transfecting eukaryotic cells.

SUMMARY OF THE INVENTION

The present invention is based on the idea of combining the minicircle technology involving the transfection of cells with the transfection (preferably co-transfection) of cells for producing viruses or viral vectors. In addition to known advantages offered by such transfection with minicircles, the use of minicircle DNA based molecules in place of plasmids leads to significantly safer preparations of viruses or viral vectors than the use of conventional vectors, such as a plasmid. Especially the viral packaging of sequences except the designated transfer sequences can be avoided, since such are not involved in the co-transfection or—in another embodiment—at least the transfer vector contains virtually no other undesired sequences. In a further embodiment, at least one or more of the co-transfection partners may be a minicircle.

Accordingly, the invention relates to a minicircle transfer vector comprising a transfer sequence and specific packaging signals on both sides of the transfer sequence for the packaging of transfer sequences in viral vector particles. Each minicircle can contain a packaging signal above and below the transfer sequence.

In a particular embodiment, a AAV viral vector, or a retrovirus such as a lentivirus, is used.

Further, the transfer sequence may comprise an expression cassette comprising at least one gene, at least one siRNA- or shRNA-encoding sequence, at least one insulator sequence, or a combination thereof. The minicircle may also comprise at least one stuffer sequence within the range between the specific packaging signals, or it may comprise at least one stuffer sequence outside the range of the specific packaging signals.

A further embodiment of the minicircle comprises at least one packaging expression cassette, wherein on the at least one packaging expression cassette all packaging proteins are encoded and can be expressed, which are necessary for the packing of the transfer sequence in particles of a viral vector.

The invention also relates to a minicircle packaging vector comprising at least one packaging expression cassette, wherein on the at least one packaging expression cassette at least one protein is encoded and can be expressed, which is necessary for the packaging of a transfer sequence in particles of a viral vector. On the at least one expression cassette all proteins may be also encoded and expressed, which are necessary for the packaging of a transfer sequence in a viral vector particle. In certain embodiments, the AAV viral vector or a retrovirus such as a lentivirus is used. When the vector is AAV, it can be from serotype 1, 2, 3, 4, 5, 6, or a synthetic serotype.

The invention also relates to cells comprising a minicircle according to one of the aforementioned embodiments.

In another aspect, the invention relates to a method for preparing a viral vector, wherein the process comprises either i) transfecting a eukaryotic cell with at least one packaging vector comprising at least one packaging expression cassette, wherein on the at least one packaging expression cassette all proteins are encoded and can be expressed that are necessary for the packaging of said transfer sequence in particles of said viral vector; and ii) transfecting said eukaryotic cell or one of its progeny with a minicircle transfer vector according to the invention comprising a transfer sequence; or iii) transfecting a eukaryotic cell with a minicircle carrying both the transfer sequence and sequences encoding all proteins necessary for the packaging of said transfer sequence in particles of said viral vector; further, expression of the at least one expression packaging cassette; and isolating the viral vector from the eukaryotic cell or one of its progeny, or from the medium in which they are located.

In a particular embodiment, a single vector is used in step (i), which is preferably a minicircle of the invention.

In another embodiment, the invention relates to a method for preparing a viral vector, the method comprising i) transfecting a eukaryotic cell with at least one minicircle packaging vector according to the invention, wherein on the at the at least one minicircle packaging vector all proteins are encoded and can be expressed that are necessary for the packaging of said transfer sequence in particles of said viral vector; and ii) transfecting said eukaryotic cell or one of its progeny with a transfer vector comprising a transfer sequence and specific packaging signals to both sides of the transfer sequence for packaging of the transfer sequence in particles of a viral vector; further, expression of the at least one packaging expression cassette; and isolating the viral vector from the eukaryotic cell or one of its progeny, or from the medium in which they are located.

The steps (i) and (ii) may be carried out in a co-transfection at the same time; step (i) can also be carried out prior to step (ii), or step (i) carried out after step (ii). In a preferred embodiment, in step (i) a packaging vector is transfected that remains episomally stable in the eukaryotic cell, and step (ii) is carried out with one of the progeny of said eukaryotic cell.

The eukaryotic cell may be a mammalian cell.

Furthermore, the invention also relates to a viral particle obtained by a method according to the invention.

Finally, the invention also provides a kit for the preparation of a viral vector comprising: a minicircle transfer vector according to the invention; and at least one packaging vector comprising at least one packaging expression cassette, wherein on the at least one expression cassette all proteins are encoded, and can be expressed, which are necessary for the packaging of said transfer sequence in particles of said viral vector. The at least one packaging vector may be a single minicircle packaging vector according to the invention. In another embodiment, the invention comprises a kit for the preparation of a viral vector comprising: a transfer vector comprising a transfer sequence and specific packaging signals to both sides of the transfer sequence for packaging the transfer sequence in particles of said viral vector; and at least one minicircle packaging vector according to the invention, wherein on the at least minicircle packaging vector all proteins are encoded and can be expressed, which are necessary for the packaging of said transfer sequence in particles of said viral vector.

The viral vector can be an AAV viral vector or a retrovirus such as a lentivirus. When the vector is AAV, it can be from serotype 1, 2, 3, 4, 5, 6, or a synthetic serotype.

DETAILED DESCRIPTION OF THE INVENTION

Minicircles

Figure 1:
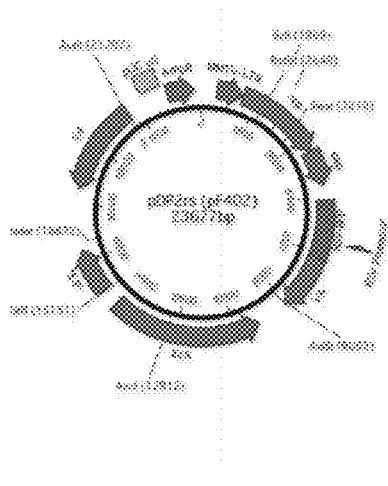
FIG. 1 shows the plasmid map of pDP2rs. All helper and packaging sequences are indicated as cap, rep, VA, E2A, E4 and E3. To identify a successful transfection, the red fluorescent protein (RFP) is used. The RFP gene is located downstream of cap. A few singular restriction sites are included for orientation.

The present invention relates in one aspect to a minicircle comprising at least one transfer sequence and particular packaging sequences on both sides of the transfer sequence for packaging of the transfer sequence in particles of a viral vector ("minicircle transfer vector"), wherein the viral vector can be, for example, an AAV vector, or a lentiviral vector.

"Minicircle" within the meaning of this invention refers to a circular double-stranded DNA containing at least one nucleic acid sequence of interest, and is substantially free of prokaryotic or bacterial nucleic acid sequences, such as those typically found in plasmids, including replication origins, marker genes or resistance genes. The minicircles may, if at all, contain only those promoters which are used for expression of genes in the nucleic acid sequence of interest. In particular, the minicircles of the invention are free of antibiotic resistance genes and bacterial replication origins. Therefore, minicircles are particularly suitable for the introduction of desired nucleic acid sequences in target cells, as the effects of undesired DNA elements can be eliminated or reduced, such as the expression or recombination of resistance genes or the presence of CpG motifs; for example, redundant and non-functional sequences can be avoided.

A "nucleic acid sequence of interest" may be any double stranded DNA sequence which is to be introduced and expressed in a eukaryotic target cell in a target cell or transposed in a nucleic acid of the target cell. The nucleic acid sequence of interest may be an expression cassette for one or more genes.

An "expression cassette" is a DNA sequence containing one or more genes and sequences that control their expression. In particular, an expression cassette comprises promoter sequences, open reading frames encoding polypeptides to be expressed, and 3' untranslated regions, usually containing a polyadenylation sequence for expression in eukaryotes. An expression cassette may also contain more than one gene, for example 2, 3, 4, 5, 6, 7, 8, 9, 10 or more genes.

In one aspect of the invention, the minicircles serve as transfer vectors for the production of viral vectors containing a transfer sequence. Herein, a "transfer sequence" is understood as any nucleic acid sequence to be packaged into a viral vector and subsequently transferred to other target cells. Transfer sequences typically contain expression cassettes on which one or more genes are encoded. In another embodiment, however, a transfer sequence may also be a sequence not encoding a protein, but merely serves to generate space between two DNA segments, or to bind or to release, respectively, DNA-binding factors (for example, nucleic acids or proteins) under certain conditions and thus interfering with the gene regulation of the target cell. Furthermore, the transfer sequence may be an RNA-coding sequence (e.g. for siRNA or shRNA) or other genetic elements that are to be effective in the target cell, e.g. insulator sequences (i.e. sequence motifs which, when integrated into the genome, influences the regulatory effect of a chromosomal segment on its neighboring regions). In addition, a transfer sequence has an intended effect in the form of a stimulation of cellular or immunological reactions (e.g. by CpG motifs, see A. Krieg et al., *Nature* 1995, 374: 546-9). For the preparation of such viral vectors, various strategies may be used. Commonly, such vectors are made in eukaryotic cells, called "producer cells". Suitable producer cell lines are e.g. HEK293, HeLa, or XDC293.

For vector production, a transfer sequence as well as other nucleic acid sequences within the expression cassettes, i.e. so-called "packaging expression cassettes" that mediates their expression, the production of viral proteins, and the packaging of the transfer sequence in viral vectors, need to be introduced in the producer cells. It is possible to introduce the transfer sequence and the packaging expression cassettes into the producer cells on the same vector as well as by using a plurality of different co-transfection vectors. Here, the vector containing the transfer sequence is thus referred to as a "transfer vector". If additional packaging expression cassettes are encoded on other vectors, such are referred to as "packaging vectors".

In one aspect, the invention therefore comprises transfer vectors, which are formed as minicircles ("minicircle transfer vectors"). Here, the transfer sequence forms part of the nucleic acid sequence of interest of the minicircles. Further, the nucleic acid of interest comprises "specific packaging signals" on both sides of the transfer sequence. These are nucleic acid sequences that mediate packaging of the transfer sequence into the viral vector in the producer cell. Typical specific packaging signals are ITR sequences for AAV and Ad vectors as well as LTR sequences for lentiviral and retroviral vectors. Exemplary transfer vectors include pTRUF11 (ATCC MBA 331) or PSUB 201 (Chadeuf et al., *Mol Ther.* 2005; 12: 744-53) for AAV or PSEW (C. Demaison et al., *Hum Gene Ther.* 2005, 12: 900-912) for lentiviral vectors.

In one preferred embodiment, a minicircle transfer vector contains one specific packaging signal, for example an ITR sequence, above and below the transfer sequence.

Figure 22A:
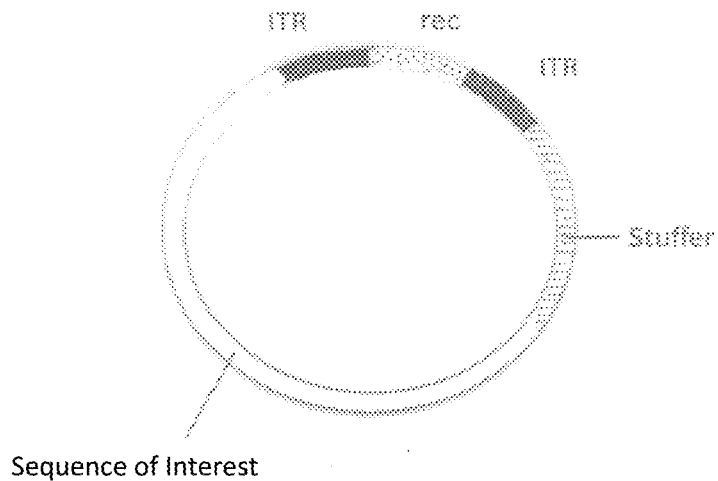
FIG. 22A shows a sketch of a minicircle as a transfer vector for AAV production, in which a transfer sequence (open section) and a stuffer sequence (striped section) are positioned between the ITR sequences (filled portion. proximal region). Beyond the ITR sequences (distal region), there is a "rec" sequence (dotted section) on the minicircle. The ITR sequences may also be LTR sequences or other signal sequences for delimitation of the viral packaging sequence portion.
Figure 22B:
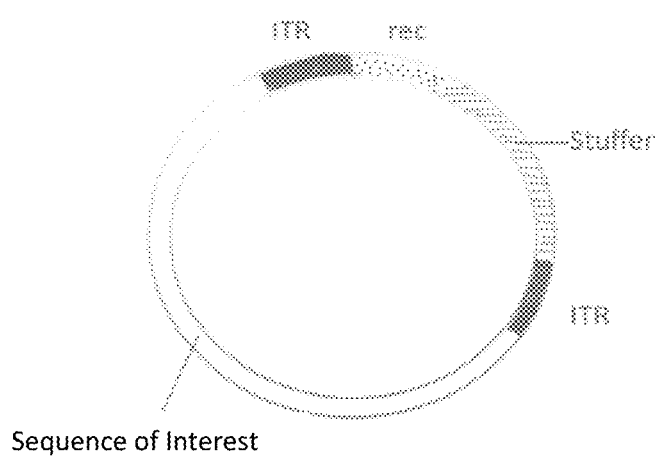
FIG. 22B shows a sketch of a minicircle as a transfer vector for AAV production, in which the transfer sequence (open portion) is positioned between the ITR sequences (solid portion; proximal region). Beyond the ITR sequences (distal area), a "rec" sequence (dotted section) and a stuffer sequence (striped section) are positioned. The ITR sequences may also be LTR sequences or other signal sequences for delimitation of the viral packaging sequence portion.
Figure 22C:
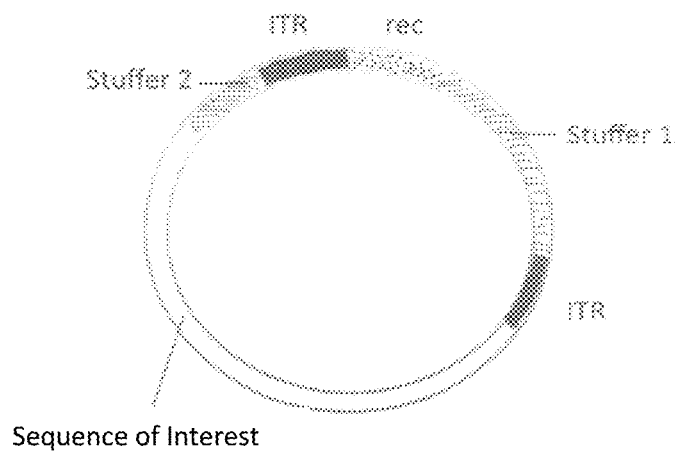
FIG. 22C shows a sketch of a minicircle as a transfer vector for AAV production, in which a transfer sequence (open section) and a stuffer sequence (striped section: Stuffer 2) is positioned between the ITR sequences (solid portion; proximal region). Beyond the ITR sequences (distal area), a "rec" sequence (dotted section) and a stuffer sequence (striped section; Stuffer 1) are positioned. The ITR sequences may also be LTR sequences or other signal sequences for delimitation of the viral packaging sequence portion.

In another preferred embodiment, a minicircle transfer vector may also include a "stuffer sequence" to improve the efficiency of viral packaging. It is an additional piece of nucleic acid sequence that is inserted to increase packing efficiency. The stuffer sequence can in principle have any sequence, however, making sure that this sequence does not contain any elements that are incompatible with a minicircle (particularly bacterial origins of replication and antibiotic resistance genes). The stuffer sequence may also be of any length, for example at least 1, 10, 100, 200, 300, 400, 500, 1000, 2000, 5000, or 10000 bp. In a preferred embodiment, the stuffer sequence is located together with the transfer sequence between the specific packaging signals to extend the transfer sequence such that it reaches the minimum length for viral packaging, as depicted in FIG. 22A. For example, for efficient packaging into an AAV vector, a sequence of 3.5 to 4 kbp between the specific packaging signals (the ITR sequences) is optimal. In another embodiment, however, a stuffer sequence can also be placed outside of the specific packaging signals, as shown in FIG. 22B. In such cases, it serves (i.e. the distance is not measured via the transfer sequence; rather in the other direction on the circular minicircle) to optimize the "outer" distance of the packaging signals for packaging. In a further embodiment of the minicircle transfer vectors of the invention, the stuffer sequences are located both between the specific packaging signals as well as outside thereof (FIG. 22C).

In one embodiment, the viral vector, in which the transfer sequence is to be packed, can be an AAV-vector. In this case, at least one packaging expression cassette is required, which contains the rep and cap genes of AAV and the adenovirus VA genes, E2A and E4. In a so-called mono-transfection, all of these genes may be present in the nucleic acid of interest of a minicircle transfer vector. Therefore, in one embodiment, the invention comprises a minicircle transfer vector containing a transfer sequence, the rep and cap genes of AAV and the adenovirus VA genes, E2A and E4.

In another embodiment, however, a double-transfection can also be used, wherein said genes are contained on a packaging vector, which is different from the minicircle transfer vector. For the production of viral vectors, a co-transfection of the producer cells with the transfer vector and packaging vector is required. The packaging vector may itself be a minicircle. In another embodiment, a triple-transfection method can also be used, in which the genes necessary for packaging are encoded on two different packaging vectors, which can be in each case minicircles again. For example, the genes rep and cap can be on a first packaging vector, and the genes VA, E2A and E4 can be included on a second packaging vector.

In another aspect, the invention therefore also includes packaging vectors that are constructed as minicircles ("minicircle packaging vectors"). In such minicircles, the nucleic acid of interest comprises at least one packaging expression cassette, on which at least one protein is encoded and can be expressed, which is necessary for the packaging of a transfer sequence in a viral vector particle. A minicircle packaging vector may encode all proteins necessary for the packaging of the transfer sequence, or only some of them.

In one particular embodiment, the invention comprises a minicircle packaging vector, which contains the AAV rep and cap genes. In a further particular embodiment, the invention comprises a minicircle packaging vector containing the adenoviral genes VA, E2A and E4. In a particular embodiment, the invention comprises a minicircle packaging vector, which contains the cap and rep genes from AAV and the adenovirus VA genes, E2A and E4.

Minicircle packaging vectors may be used together with minicircle transfer vectors or other transfer vectors, which are not minicircles, to achieve the packaging of a transfer sequence into viral particles.

Monomeric minicircles according to the present invention can have very different sizes, for example between 500 and 30000 bp, such as about 500 bp, 1000 bp, 1500 bp, 2000 bp, 2500 bp, 3000 bp, 4000 bp, 5000 bp, 6000 bp, 8000 bp, 10,000 bp, 12,000 bp, 15,000 bp, 20,000 bp, 25,000 bp and 30,000 bp. For minicircle transfer vectors, sizes between 1000 bp and 6000 bp are preferred. In minicircle packaging vectors, a larger size may be necessary. For example, the minicircle packaging vector MC.DP2rs from Example 4 has a size of 21870 bp.

Figure 23:
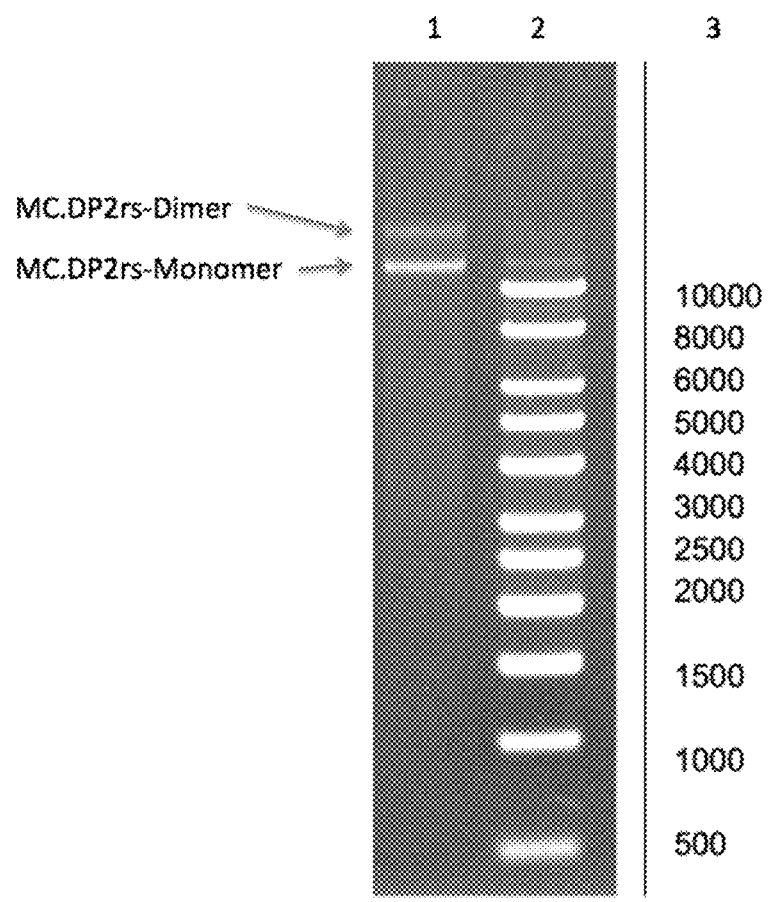
FIG. 23 shows an agarose gel with undigested monomeric and dimeric PP.DP2rs (lane 1) next to a DNA length standard defined from linear DNA fragments length (1 Kb ladder, PlasmidFactory, Bielefeld; rounded to the ladder size specifications of the entire 500 bp as provided on the right of the gel).

In addition, minicircle DNA may also occur in di- or multimeric form, e.g. between 100 and 100000 bp. For example, a dimer of the minicircle MC.DP2rs has a size of 43740 bp (see also FIG. 23).

Preferably, the minicircles of the invention are supercoiled.

In a further embodiment, the minicircles of the invention have the additional property to be able to remain episomally stable in the producer cell and thus—without integration into the cellular chromosome—the acquired property for the production of viruses or viral vectors remains longer compared to what is observed in classical transient transfections. The non-integration in the genome of the cell has the advantage that the chromosomal structure of the producer cell—in contrast to integration (see for example Russell and Hendrie, *Mol. Ther.* 2005, 12: 9-17)—remains intact and even in non-mutagenic insertion the sequences encoded on the minicircle are not downregulated. Episomal transfection can be realized for example by a S/MAR sequence for episomal stabilization (see, e.g., Haase et al., *BMC Biotechnol.,* 2010 10:20). The transfection of a cell by a transfer plasmid, whereby the cell already contains a stabilized episomal helper and/or packaging plasmid, further results in the production of viral vectors, even if a significant amount of time has passed between the two transfections or where several generations of cell division have already occurred.

Production of Minicircles

The minicircles of the invention may be produced by recombination of suitable plasmids, such as those described in WO 96/26270 or EP 1620559. Here, one begins with a plasmid ("parental plasmid") containing the entire sequence of the desired minicircle (minicircle region) and additionally a plasmid backbone (miniplasmid region) (see FIG. 2, FIG. 7, FIG. 10). Flanking each specific recombinase recognition site sequence between the minicircle region and the miniplasmid region is a site that can be recognized by a corresponding recombinase. A recombinase enzyme is any enzyme capable of catalyzing the specific recombination of the parental plasmid into a minicircle and a remainder, the miniplasmid. The two recombinase recognition sequences need to be oriented such that upon recombination the miniplasmid and minicircle completely separate and does not form a single modified plasmid.

The recombinase recognition sequences may be connected directly to the nucleic acid sequence of interest, or the sequences may be separated by a stuffer sequence. Stuffer sequences may be attached to both sides of the nucleic acid sequence of interest, or only on one side. The stuffer sequences preferably have a length of 1 to 1000 bp, e.g. 1, 10, 20, 50, 100, 200, 300, 400, 500, 600, 700, 800, 900 or 1000 bp. When present on both sides of the nucleic acid sequence of interest, stuffer sequences can have identical or different lengths. In particular, such a stuffer sequence may include one or more identification sequences as described below.

Examples of possible recombinases are the integrases of the bacteriophage λ (see A. Landy et al., Science 1977, 197 (4309): 1147-1160), P22 and Φ80 (see J M Leong et al., J. Biol. Chem. 1985, 260(7): 4468-4470), HP1 integrase from Haemophilus influenzae (see M A Hauser et al., J. Biol. Chem. 1992, 267 (10): 6859-6864), Cre integrase from the phage P1, the integrase from plasmid pSAM2 (see EP350341), Flp recombinase from Plasmid 2μ or ΦC31 integrase. Alternatively, recombinases from transposon of the Tn3 family can be used such as the parA resolvase from RP4 (see L. Eberl et al., Mol. Microbiol. 1994, 12 (1): 131-141), the resolvases of transposon Tn3, Tn21 or Tn522 (see W M Stark et al., Trends Genet., 1992, 8 (12): 432-439), or the Gin invertase from bacteriophage μ.

Figure 2:
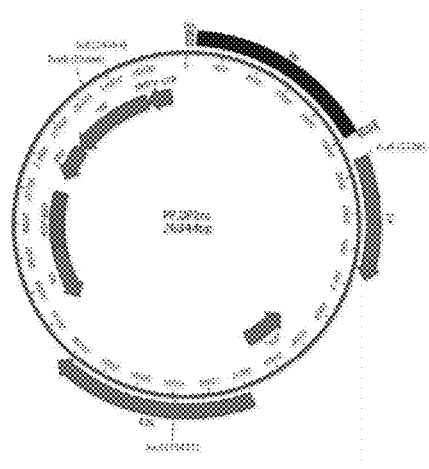
FIG. 2 shows the map of parental plasmid PP.DP2rs. The recombinase recognition sequences are referred to as "rec" and delimits the portion of the parental plasmids, which after recombination becomes the minicircle (minicircle region), from the bacterial plasmid portion ("BB"; miniplasmid region), which after recombination becomes miniplasmid containing the necessary regulatory elements, such as a gene for the recombinase (here, ParA resolvase), but also antibiotic resistance genes (here, kanamycin resistance), and the bacterial origin of replication. Some singular restriction sites are included for guidance.

An exemplary arrangement of the nucleic acid sequence of interest according to the invention on a parental plasmid (PP-DP2rs) is shown in FIG. 2. The "rec" sequences are used here for the preparation of a minicircle vector for packaging AAV particles. The nucleic acid sequence of interest is delimited by rec sequences and contains packaging expression cassettes including the genes rep, cap, VA, E2A, E3, and E4.

The parental plasmids of the invention may be prepared using techniques known through typical microbiological strategies and methods. An exemplary starting point, for example, is the plasmid pDP2rs (PlasmidFactory, Bielefeld, DE, Item No. PF402; see FIG. 1, SEQ ID NO: 1), which contains the necessary packaging genes for AAV production. The relevant sequences are located between the restriction sites for PacI. A DNA fragment may be cut by this enzyme, if there are no further PacI sites within the nucleic acid sequence of interest. Alternatively, such a fragment can be obtained by amplification using PCR based on primers located outside of, but close to the desired sequence fragment.

The resulting restriction fragment, which comprises the nucleic acid sequence of interest, can then be cloned into a precursor plasmid containing the miniplasmid region and the recombinase recognition sequences of the desired parental plasmid. If necessary, the fragment may be initially subcloned into another plasmid to be able to use a restriction enzyme that is compatible with the precursor plasmid. Cloning of a PCR fragment can be carried out either in the same way or via a shuttle vector for cloning of PCR fragments. In all cases, the insertion site needs to be in the region between the recombinase recognition sequences of precursor plasmids. This results in the parental plasmid that is required for the formation of minicircle and miniplasmid. Cloning is carried out by inserting the PacI fragment into a PacI restriction site of the precursor plasmid.

This "insertion" can be carried out using classic ligation of appropriate DNA ends (blunt or "sticky"), or by recombination (described in Hartley et al., Genome Research 2000, 10: 1788-1795), where it should be ensured that the recombination mechanisms used in the latter case do not interfere with those of the cleavage into minicircle and miniplasmid.

It is evident that a suitable parental plasmid can be also constructed on the basis of other plasmids than the abovementioned. Different restriction enzymes may also be employed. The decisive factor is that the structure of the resulting parental plasmid needs to contain one or more nucleic acid sequences of interest between two suitably oriented recombinase-recognition sequences.

Recombination of parental plasmids can be carried out in vitro or in vivo. An advantage of in vivo recombination in host cells is that the parental plasmid does not need to be purified, provided that the expression of the corresponding recombinase can be induced in the host cells. The required gene encoding the recombinase may be present in the host cell on another nucleic acid molecule. Particularly advantageous is the recombinase gene being present within the miniplasmid region on the parental plasmid. Preferably, the expression of the recombinase is inducible, for example, by a temperature change or the addition of a metabolite. After induction of recombinase expression in the host cell, the parental plasmid is cleaved into two supercoiled, circular molecules, namely the minicircle and the miniplasmid, which may then be separated from each other following cell lysis, or implemented in the cell containing information encoded by the nucleic acid sequence of interest.

The host cell can thus also be the producer cell, wherein expression control of the recombinase in eukaryotic cells can be guaranteed.

Alternatively, a minicircle can also be prepared from a plasmid using conventional restriction and ligation techniques. Here, the region of the parent plasmid which is to form the minicircle, is cut from the plasmid, for example, by means of a restriction enzyme, and ligated to a minicircle. The minicircle can be assembled by several distinct sections. It must be noted, however, that a minicircle produced in this way is generally not supercoiled, unless it is subsequently supercoiled in vitro.

In one embodiment of the invention, the minicircle may also contain at least one identification sequence for purifying the minicircle, and also for other purposes. As an identification sequence, each sequence can be used that enables the separation of the minicircles from the miniplasmid. In particular, the identification sequence can be those sequences that bind to a specific ligand thus being able to complex the minicircle with the ligand. The ligand may be a DNA-binding protein or a nucleic acid. The purification can then be performed e.g. by chromatographic methods, in particular, affinity chromatography directed against the identification sequence through the immobilized ligand. Suitable purification systems include, for example, triple helix affinity chromatography (THAC, see P. Wils et al., *Gene Therapy*, 1997, 4(4): 323-330), the lacO/lacI system (see J. Lundeberg et al., *Genet. Anal. Techn. Appl.* 1990, 7:47-52), the repU/dso-system (see A. Müller et al., *Nucleic Acids Research* 1995, 23(11): 1894-1900) or systems of the repressor of bacteriophage λ or bacteriophage 434 with the corresponding promoter, for which the respective repressor is specific.

Particularly preferred are embodiments where the identification sequence is located in the minicircle region of the parental plasmid, or within the sequence of interest. When a spontaneous and accidental recombination of the recombinase recognition sequences occurs in such a minicircle region of a parental plasmid (or its original or precursor plasmid) during the production process, this results in a defective product where the identification sequence is deleted in addition to the nucleic acid sequence of interest. Therefore, only intact minicircles are isolated by affinity purification directed against the identification sequence. Accordingly, the problem of minicircle preparation contamination by defective deletion products is avoided.

A minicircle may also contain more than one identification sequence. Here, the identification sequences can be identical and are present as direct repeats or repeats separated by a spacer. But two or more different identification sequences may also be used for different purposes. For example, a sequence forming a triple helix with an oligonucleotide ligand, may be present outside the nucleic acid sequence of interest for purifying the minicircles before transfection, and at the same time, a lacOS sequence may be contained within the nucleic acid sequence of interest to detect the presence in the cell after transfection or to measure its efficiency.

Illustrated by the parental plasmid PP DP2rs of FIG. 2, the region within the rec-sequences, which also includes the packaging expression cassettes, is suitable for incorporating at the edges of said region, or between the packaging expression cassettes located therein, one or more identification sequences with which a minicircle is to be identified and separated from a miniplasmid generated during minicircle production.

Cells

In another aspect, the invention also relates to a cell containing a minicircle according to the invention. This may be a cell from any species. In particular, prokaryotic and eukaryotic cells that contain the minicircle according to the invention are encompassed by the invention. In some embodiments, the cell is a vertebrate cell, more preferably a human cell. In some embodiments, the cell is a producer cell for viral vectors, such as a HEK 293, or HeLa cell.

Cells containing a minicircle according to the invention may be prepared by conventional transfection methods known in the art. For example, chemical transfection using calcium phosphate can be used (see F L Graham et al., *Virology* 1973, 52(2): 456-467), or using dendrimers (Colander H L Fu et al., *Journal of Control Release* 2007, 124(3):181-188) or using cationic polymers (see EP 1505089). Further methods include lipofection (see Felgner P L et al., *PNAS,* 1987, 84(21): 7413-7417) electroporation (see E. Neumann, et al, *EMBO J.* 1982, 1(7):841-845), optical transfection (see M. Tsukakoshi et al., *Applied Physics B-Photophysics and Laser Chemistry* 1984, 35(3): 135-140), magnetofection (see F. Scherer et al., *Gene Ther.,* 2009, 9(2): 102-109) or impalefection (see T E McKnight et al., *Nano Letters* 2004, 4(7): 1213-1219). Particle-based techniques such as gene gun can be also used (see U.S. Pat. No. 5,219,746). Preferred methods are calcium phosphate transfection, lipofection and electroporation.

Furthermore, a minicircle according to the invention is produced directly in the target cell, as described above. Here, the target cell is first transfected with a parental plasmid containing the minicircle followed by induction of the expression of the corresponding recombinase in the target cell, such that the processing of the parental plasmid is possible by recombination into a miniplasmid and minicircle. For this embodiment, the controlled expression of the recombinase needs to be ensured in the eukaryotic cell and a gene encoding for the recombinase gene needs to be present in the target cell. The recombinase gene can be either integrated into the genomic DNA of the target cell, or be present on a different nucleic acid molecule. Particularly advantageous is when the recombinase gene is present within the miniplasmid region on the parental plasmid.

Method for Producing Viral Vectors

Viral vectors are preferably produced by transient transfection, but also by stable transfection, of eukaryotic producer cells with DNA. The DNA molecules are thus simultaneously or successively brought into the cell, and the information for cellular virus production provided thereon is activated. The DNA molecules provide all components required for producing viral particles in the host cell and assembling them into viral particles.

Typical viral vectors are HSV (herpes simplex virus), Ad (adenovirus), the aforementioned AAV and lentiviruses (LV) as well as retroviruses (RV). The two last-mentioned viruses integrate into the genome of the host cell, while the others remain episomal or at least predominantly episomally in the cell. These vectors have different packaging capacities: RV and LV about 7-8 kbp, Ad about 8 kbp (respectively 30 kbp in the particular variants HC/gutless) and HSV about 150 kbp (amplicon) or 40 kbp (replication-defective).

Production of Adeno-Associated Virus (AAV):

In the following, a preferred method for producing adeno-associated virus is disclosed.

By culturing the producer cells to be transfected, sufficient quantities of these cells are provided. The producer cells are then transfected with the necessary transfer and packaging vectors. For each of these vectors, a minicircle may be used. For example, the chemical transfection using calcium phosphate (see F L Graham et al., *Virology* 1973, 52(2): 456-467), using dendrimers (Colander H L Fu et al., *Journal of Control Release* 2007, 124(3):181-188) or using cationic polymers (see EP 1505089) are all suitable. Further methods include lipofection (see Felgner P L et al., PNAS 1987, 84(21):7413-7417), electroporation (see E. Neumann, et al., *EMBO J.* 1982, 1(7): 841-845), optical transfection (see M. Tsukakoshi et al., *Applied Physics B-Photophysics and Laser Chemistry* 1984, 35(3): 135-140), magnetofection (see F. Scherer et al., *Gene Ther.,* 2009, 9(2):102-109) or impalefection (see T E McKnight et al., *Nano Letters* 2004, 4(7): 1213-1219). Also particle-based techniques such as a gene gun may be used (see U.S. Pat. No. 5,219,746). Preferred methods are calcium phosphate transfection, lipofection and electroporation.

It is important that both the rep and cap genes of AAV and the adenovirus helper sequences VA, E2A and E4 are transfected. Therefore, as already described above, mono (transfer sequence and all packaging sequences on the same vector), double (transfer sequence and packaging sequences on different vectors) or triple transfection systems (packaging sequences on two vectors, which are different from the transfer vector) are typically used. If several vectors are to be transfected, this can be carried out by co-transfection. In this case, care should be taken that all vectors are present in equimolar amounts.

Alternatively, in case of a multiple transfection strategy, the first transfected vector can be episomally stabilized in the producer cells. Typically, this will relate to the packaging vector. In such a case, the second transfection can take place either days, weeks or months after the first transfection, even if the originally transfected cells have already divided several times.

Harvesting the virus particles typically occurs 2-3 days after the last transfection. Therefore, the producer cells are centrifuged, lysed and disrupted by repeated freezing in liquid nitrogen and thawing. Cellular DNA and RNA, as well as any remaining plasmid DNA is removed by a benzonase treatment. The separation of cellular proteins is performed via an iodixanol gradient centrifugation. Subsequently, the virus preparation is separated from iodixanol by affinity chromatography or gel filtration, and further purified.

Production of Lentiviral Vectors (LV):

For the production of lentiviral vectors, additional DNA is co-transfected in addition to the transfer vector. These are plasmids with sequences for the helper and packaging information (for triple transfection, in addition to a transfer plasmid, another one is used including gag and pol as well as one with env). The gag and pol sequences are e.g. positioned on the packaging vectors pCMVdeltaR8.9 (see R. Zufferev et al., *Nature Biotechnol* 1997, 15(9): 871 -875) or pHR' (see H. Miyosh, et al., *PNAS* 1997, 94(19):10319-10323) and encode a gag-pol precursor protein, which contains the structural proteins of the vector particle. The env sequences, for example, on the plasmids pCG-Fcdelta30 or pCG-H alphaCD20 encode a glycoprotein which enables cell binding and cell entry. The production of viral particles is reviewed in detail by S. Funke et al. (*Mol Therapy* 2008,16: 1427-1436) and C J Buchholz, et al. (*Trend Biotechnol.* 2009, 27(5):259-265).

The implementation of a pseudo-typing (exchanging the viral envelope proteins with foreign envelope proteins, e.g. to change the tropism—that is, the target detection when infecting a host cell) is also possible for these viral particles. Therefore, the env-carrying packaging vectors are replaced by those encoding other glycoproteins. For example, the glycoprotein G of the vesicular stomatitis virus (VSV-G) is used, which allows transduction of virtually all cell types. An example for this is the plasmid pMD.G or pMD.2G (Addgene No. 12259) or pHIT123 (Soneoka Y. et al., *Nucleic Acids Res.* 1995, 23:628-633), which encodes the env protein of the Moloney murine leukemia virus (MoMLV).

Kits

In a further aspect, the invention also encompasses kits for the production of viral vectors in a producer cell. A kit includes a transfer vector and at least one packaging vector. At least one of these vectors is a minicircle (minicircle transfer vector and/or minicircle vector packaging) according to the invention. In a particular embodiment, the viral vectors to be produced are AAV vectors or retroviral vectors such as lentiviral vectors.

The transfer vector and the at least one packaging vector can be provided dry, e.g. lyophilized. Alternatively, they may also be dissolved in a buffer, with the solution provided in a liquid or frozen form. Furthermore, the components are available either mixed or separated from each available in different containers. In addition to the transfer and packaging vectors, the kit may also contain other ingredients that are useful for performing a method according to the invention, such as chemicals, reagents, buffers, solvents or media for performing the method of the invention. In particular, the kit may contain reagents that are required for chemical transfection or lipofection. Some or all of the reagents may be provided in measured unit amounts e.g. to minimize pipetting on the part of the user.

In addition, the kit may also contain descriptions of the transfer vector and/or the at least one packaging vector, such as vector maps or sequences. Similarly, instructions for implementation of the corresponding embodiment of the invention may form part of the kit.

EXAMPLES

Example 1

Construction of a Parental Plasmid (PP.DP2rs) for Minicircles Comprising the Helper/Packaging Sequences from pDP2rs The plasmid pDP2rs (23677 bp, Article No. PF402, PlasmidFactory, Bielefeld, DE) containing several expression cassettes for the AAV helper/packaging functions, especially the cap protein of serotype 2 and a gene for red fluorescent protein (RFP) (FIG. 1. SEQ ID NO: 1) is used as starting material for the selective extraction of the region including the above-mentioned genetic characteristics. Thereby, an approx. 21.5 kb DNA fragment and an (unwanted) approx. 2 kb DNA fragment is generated through restriction digestion with PacI (Article No. R0547L, NEB, Frankfurt, Germany). The 21.5 kb fragment is purified by agarose gel electrophoresis, gel extraction and DNA extraction (Macherey-Nagel, Düren, Germany).

The precursor plasmid pP11, which serves for incorporation of the 21.5 kb fragment (see Mayrhofer et al., *J. Gene Med.*, 2008, 10(11): 1253-1269, albeit without MCS, without spacers and with one instead of two identification sequences, as described in DE 10 2011 118 018), includes a PacI restriction site, which is flanked by recombinase recognition sequences of the parA resolvase, and an expression cassette of the parA resolvase outside of the recombinase recognition sequences. This plasmid is cut with the enzyme PacI (Article No. R0547L, NEB, Frankfurt, Germany) and dephosphorylated with alkaline phosphatase (Article No. M0290L, NEB, Frankfurt, Germany). Thereafter, the fragment is ligated with T4 ligase into the linearized vector to obtain PP.DP2rs (FIG. 2).

Example 2

Figure 6:
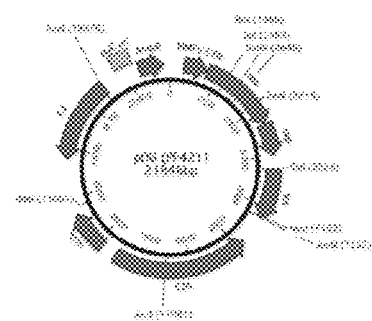
FIG. 6 shows the plasmid map of pDG. All helper and packaging sequences are indicated as cap, rep, VA, E2A, E4 and E3. The plasmid does not contain a gene for RFP. Some singular restriction sites are included for guidance.

Construction of a Parental Plasmid (PP.DG) for Minicircles Comprising the Helper/Packaging Sequences from pDG The plasmid pDG (21849 bp, Article No. PF421, PlasmidFactory, Bielefeld, DE) containing several expression cassettes for the AAV helper/packaging functions, especially the cap protein of serotype 2 but no gene for red fluorescent protein (RFP) (FIG. 6, SEQ ID NO: 2) is used as starting material for the selective extraction of the region including the above-mentioned genetic characteristics. Thereby, an approx. 20 kb DNA fragment and an (unwanted) approx. 2 kb DNA fragment is generated through restriction digestion with PacI (Article No. R0547L, NEB, Frankfurt, Germany. The 20 kb fragment is purified by agarose gel electrophoresis, gel extraction and DNA extraction (Macherey-Nagel, Düren, Germany).

Figure 7:
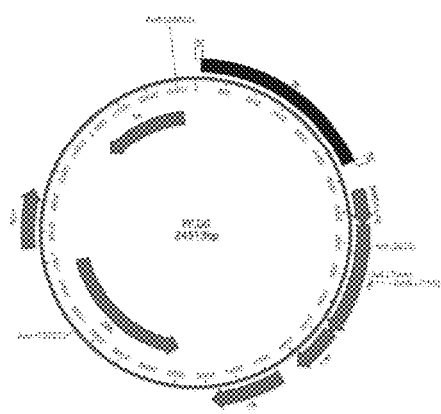
FIG. 7 shows the map of parental plasmid PP.DG. The recombinase recognition sequences are referred to as "rec" and delimit the portion of the parental plasmid, which after recombination becomes the minicircle (minicircle region) from the bacterial plasmid portion ("BB"; miniplasmid region), which after recombination becomes miniplasmid containing the necessary regulatory elements, such as a gene for the recombinase (here, ParA resolvase), but also antibiotic resistance genes (here, kanamycin resistance), and the bacterial origin of replication. Some singular restriction sites are included for guidance.

The precursor plasmid pP11, which serves for incorporation of the 20 kb fragment (see Mayrhofer et al., *J. Gene Med.*, 2008, 10 (11): 1253-1269, albeit without MCS, without spacers and with one instead of two identification sequences, as described in DE 10 2011 118 018), includes a PacI restriction site, which is flanked by recombinase recognition sequences of the parA resolvase and an expression cassette of the parA resolvase outside of the recombinase recognition sequences. This plasmid is cut with the enzyme PacI (Article No. R0547L, NEB, Frankfurt, Germany) and dephosphorylated with alkaline phosphatase (Article No. M0290L, NEB, Frankfurt, Germany). Thereafter, the fragment is ligated with T4 ligase into the linearized vector to obtain PP.DG (FIG. 7).

Example 3

Figure 9:
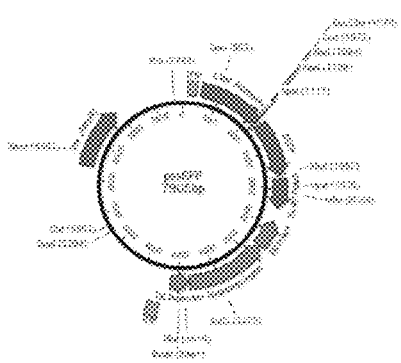
FIG. 9 shows the map of plasmid pssGFP. In the left part of the plasmid, next to the bacterial replication origin (not shown), the antibiotic resistance gene (bla) is located. The right part is limited by ITR sequences and contains two expression units directed on each other: for green fluorescent protein (EGFP) under the control of a CMV promoter and a polyadenylation sequence from SV40 (SV40 polyA), as well as for hygromycin under the control of a TK promoter with a TK-polyadenylation sequence (TK polyA). Some singular restriction sites are included for guidance.

Construction of a Parental Plasmid (PP.ssGFP) for Minicircles Comprising the Transfer Plasmid Sequences from pssGFP The plasmid pssGFP (7905 bp, H. Buening, Univ. Cologne, DE) containing expression cassettes for eGFP under the control of a CMV promoter, and hygromycin under the control of a TK promoter (FIG. 9A, SEQ ID NO: 3) is used as starting material for the selective extraction of the region including the above-mentioned genetic characteristics. The plasmid is subject to restriction digestion with PvuII (Article No. R0151M, NEB, Frankfurt, Germany) to yield an approximately 4.3-kb DNA fragment and an (unwanted) approximately 3.6 kb DNA fragment. The 4.3 kb fragment contains at both of its ends an ITR sequence—the packaging signal for packaging of the flanked sequence in the context of AAV genesis in cells (5'-CGCGCTCGCTCGCTCACTGAGGC-CGCCCGGGCAAAGCCCGGGCGTCGGGCGA CCTTTGGTCGCCCGGCCTCAGTGAGC-GAGCGAGCGCGCAGAGAGGGAGTGGCCA ACTC-CATCACTAGGGGTTCCT-3', SEQ ID NO:7; and 5'-AG-GAACCCCTAGTGAT GGAGTTGGCCACTCCCTCTCT-GCGCGCTCGCTCGCTCACTGAGGCCGGGCGACCA AAGGTCGCCCGACGCCCGGGCTTTGC-CCGGGCGGCCTCAGTGAGCGAGCGAG-3', SEQ ID NO:8)—and is purified using agarose gel electrophoresis, gel extraction and DNA extraction (Macherey-Nagel, Düren, Germany).

Figure 10:
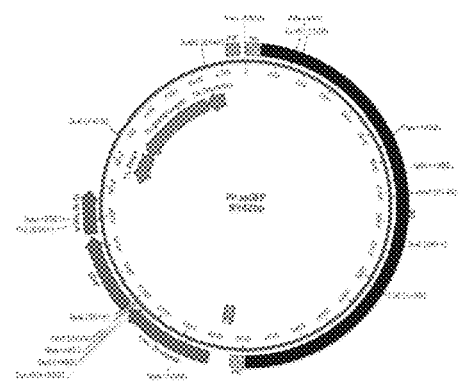
FIG. 10 shows the map of parental plasmid (PP-ssGFP). The recombinase recognition sequences are referred to as "rec" and delimit the portion of the parental plasmid, which after recombination becomes the minicircle (minicircle region) from the bacterial plasmid portion ("BB"; miniplasmid region), which after recombination becomes miniplasmid containing the necessary regulatory elements, such as a gene for the recombinase (here, ParA resolvase), but also antibiotic resistance genes (here, kanamycin resistance), and the bacterial origin of replication. Some singular restriction sites are included for guidance.

The precursor plasmid pP11, which serves for incorporation of the 4.3 kb fragment (see Mayrhofer et al., *J. Gene Med.*, 2008, 10 (11): 1253-1269, albeit without MCS, without spacers and with one instead of two identification sequences, as described in DE 10 2011 118 018), includes a PmeI restriction site, which is flanked by recombinase recognition sequences of the parA resolvase and an expression cassette of the parA resolvase outside of the recombinase recognition sequences. This plasmid is cut with the enzyme PmeI (Article No. R0560L, NEB, Frankfurt, Germany) and dephosphorylated with alkaline phosphatase (Article No. M0290L, NEB, Frankfurt, Germany). Thereafter, the fragment is ligated with T4 ligase into the linearized vector to obtain the plasmid PP.ssGFP (FIG. 10).

Example 4

Figure 12:
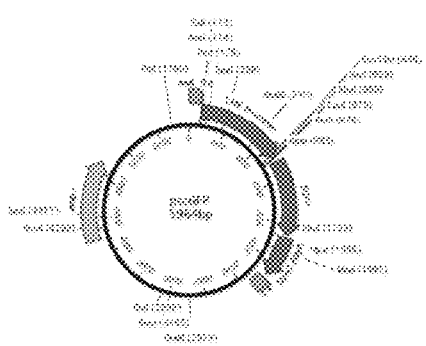
FIG. 12 shows the map of the plasmid pscGFP. Unlike pssGFP (FIG. 9), this plasmid is used to produce self-complementary AAV viruses. Besides the bacterial origin of replication (not shown) the antibiotic resistance gene (amp r) is located in the left part of the plasmid. The right part is delimited by ITR sequences and contains two expression units directed on each other: for green fluorescent protein (EGFP) under the control of a CMV promoter and with a poly-adenylation sequence from SV40 (SV40 polyA). Some singular restriction sites are included for guidance. One of the two ITR sequences (mut. ITR) is mutated.

Construction of a Parental Plasmid (PP.scGFP) for Minicircles Comprising the Transfer Plasmid Sequences from pscGFP for Generating Self-Complementary AAV Vectors The plasmid pscGFP (5964 bp, H. Buening, Cologne Univ. DE), containing expression cassettes for eGFP under the control of the CMV promoter (FIG. 12., SEQ ID NO: 4), is used as starting material for the specific extraction of that region including the above-mentioned genetic characteristics. The plasmid is subject to restriction digestion with PvuII (Article No. R0151M, NEB, Frankfurt, Germany) to yield an approximately 2.3-kb DNA fragment and an (unwanted) approximately 3.6 kb DNA fragment. The 2.3 kb fragment contains at both of its ends an ITR sequence—the packaging signal for packaging of the flanked sequence in the context of AAV genesis in cells (5'-CGCGCTCGCTCGCTCACTGAGGC-CGCCCGGGCAA AGCCCGGGCGTCGGGCGAC-CTTTGGTCGCCCGGCCTCAGTGAGCGAGCGAGCGC GCAGAGAGGGAGTGG-3', SEQ ID NO:9 and 5'-AG-GAACCCCTAGTGATGGAGTTG GCCACTCCCTCTCT-GCGCGCTCGCTCGCTCACTGAGGC-CGGGCGACCAAAGGTCC CGACGCCCGGGCTTTGCCCGGGCGGCCT-CAGTGAGCGAGCGAG-3', SEQ ID NO:8). The sequence of SEQ ID NO: 8 in this case represents a mutant ITR, which allows the production of self-complementary vectors as disclosed above. The fragment is purified using agarose gel electrophoresis, gel extraction and DNA extraction (Macherey-Nagel, Düren, Germany).

Figure 13:
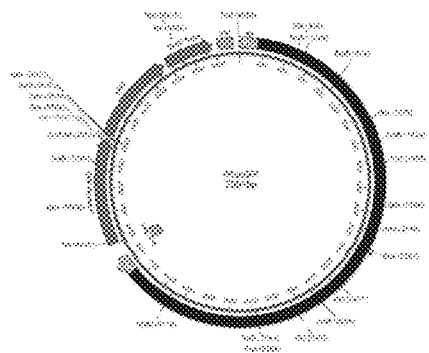
FIG. 13 shows the map of parental plasmid (PP-scGFP). The recombinase recognition sequences are referred to as "rec" and delimit the portion of the parental plasmid, which after recombination becomes the minicircle (minicircle region) from the bacterial plasmid portion ("BB"; miniplasmid region) which after recombination becomes miniplasmid containing the necessary regulatory elements, such as a gene for the recombinase (here, ParA resolvase), but also antibiotic resistance genes (here, kanamycin resistance), and the bacterial origin of replication. Some singular restriction sites are included for guidance.

The precursor plasmid pP11, which serves for incorporation of the 2.3 kb fragment (see Mayrhofer et al., *J. Gene Med.*, 2008, 10 (11): 1253-1269, albeit without MCS, without spacers and with one instead of two identification sequences, as described in DE 10 2011 118 018), includes a PmeI restriction site, which is flanked by recombinase recognition sequences of the parA resolvase and an expression cassette of the parA resolvase outside of the recombinase recognition sequences. This plasmid is cut with the enzyme PmeI (Article No. R0560L, NEB, Frankfurt, Germany) and dephosphorylated with alkaline phosphatase (Article No. M0290L, NEB, Frankfurt, Germany). Thereafter, the fragment is ligated with T4 ligase into the linearized vector to obtain the plasmid PP.scGFP (FIG. 13).

Example 5

Figure 15:
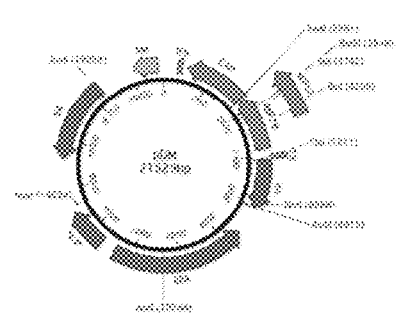
FIG. 15 shows the plasmid map of PDM-1, a plasmid vector for production of AAV particles. All helper and packaging sequences are indicated as cap, rep, VA, E2A, E4 and E3. The rep (Rep52 and Rep78) and cap—(CAP) sequences are flanked as a cluster by AAV ITR sequences. Some singular restriction sites are included for guidance.

Construction of a Parental Plasmid (PP.DM) for Minicircles Comprising the Helper/Packaging Sequences from pDG and an ITR-Flanked Transfer Sequence for the Production of AAV Particles by Transfection with Only One DNA Vector The plasmid pDM (21529 bp, Article No. PF400, Plasmid-Factory, Bielefeld, DE) containing several expression cassettes for the AAV helper/packaging functions, especially the cap- of serotype 2 and two rep-proteins (as a cluster flanked by AAV ITR sequences)(FIG 15. SEQ ID NO: 5) is used as starting material for the selective extraction of the region including the above-mentioned genetic characteristics. The plasmid is subject to restriction digestion with PacI (Article No. R0547L, NEB, Frankfurt, Germany) to yield an approximately 20-kb DNA fragment and an (unwanted) approximately 2 kb DNA fragment. The 20 kb fragment was purified by agarose gel electrophoresis, gel extraction and DNA extraction (Macherey-Nagel, Düren, Germany).

Figure 16:
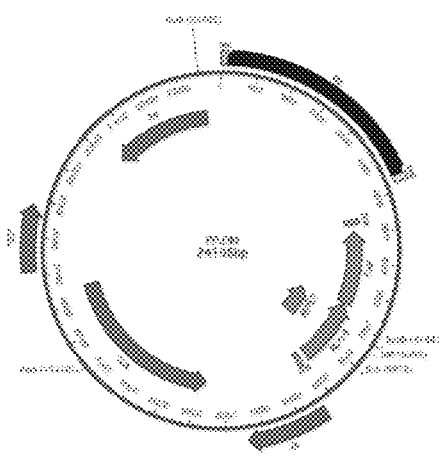
FIG. 16 shows the map of parental plasmid PP.DM. The recombinase recognition sequences are referred to as "rec" and delimit the portion of the parental plasmid, which after recombination becomes the minicircle (minicircle region) from the bacterial plasmid portion ("BB"; miniplasmid region), which after recombination becomes miniplasmid containing the necessary regulatory elements, such as a gene for the recombinase (here, ParA resolvase), but also antibiotic resistance genes (here, kanamycin resistance), and the bacterial origin of replication. Some singular restriction sites are included for guidance.

The precursor plasmid pP11, which serves for incorporation of the 20 kb fragment (see Mayrhofer et al., *J. Gene Med.*, 2008, 10 (11): 1253-1269, albeit without MCS, without spacers and with one instead of two identification sequences, as described in DE 10 2011 118 018), includes a PacI restriction site, which is flanked by recombinase recognition sequences of the parA resolvase and an expression cassette of the parA resolvase outside of the recombinase recognition sequences. This plasmid is cut with the enzyme PacI (Article No. R0547L, NEB, Frankfurt, Germany) and dephosphorylated with alkaline phosphatase (Article No. M0290L, NEB, Frankfurt, Germany). Thereafter, the fragment is ligated with T4 ligase into the linearized vector to obtain PP.DM (FIG. 16).

Example 6

Figure 18:
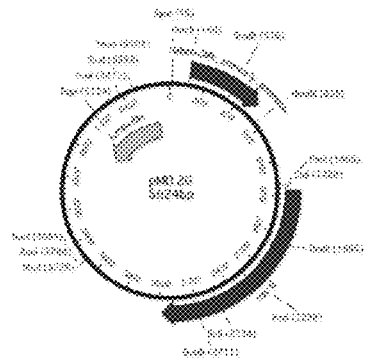
FIG. 18 shows the plasmid map of pMD.2G (Addgene no. 12259), which encodes under the control of the CMV promoter for glycoprotein G of the vesicular stomatitis virus (VSV-G) and is cotransfected for production of LV. Some singular restriction sites are included for guidance.

Construction of a Parental Plasmid (PP.MD2G) for Minicircles Comprising the Glycoprotein G of the Vesicular Stomatitis Virus (VSV-G) for Use in the Production of Lentiviral Particles by Co-Transfection Plasmid pMD.2G (5824 bp) containing an expression cassette for the glycoprotein G of the vesicular stomatitis virus (VSV-G) under the control of a CMV promoter (FIG. 18. SEQ ID NO: 6), as starting material for the selective extraction of the region including the above-mentioned genetic characteristics. The plasmid is subject to restriction digestion with HincII (Article No. R0103L, NEB, Frankfurt, Germany) and MscI (Article No. R0534M, NEB, Frankfurt, Germany) to yield an approximately 3.5-kb DNA fragment and an (unwanted) 2.3 kb DNA fragment. The 3.5 kb fragment was purified by agarose gel electrophoresis, gel extraction and DNA extraction (Macherey-Nagel, Düren, Germany).

Figure 19:
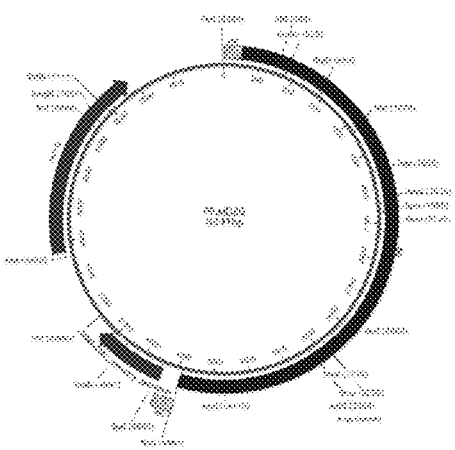
FIG. 19 shows the map of parental plasmid PP.MD2G. The recombinase recognition sequences are referred to as "rec" and delimit the portion of the parental plasmid, which after recombination becomes the minicircle (minicircle region) from the bacterial plasmid portion ("BB"; miniplasmid portion), which after recombination becomes miniplasmid containing the necessary regulatory elements, such as a gene for the recombinase (here, ParA resolvase), but also antibiotic resistance genes (here, kanamycin resistance), and the bacterial origin of replication. Some singular cutting sites are included for guidance.

The precursor plasmid pP11, which serves for incorporation of the 3.5 kb fragment (see Mayrhofer et al., *J. Gene Med.*, 2008, 10(11): 1253-1269, albeit without MCS, without spacers and with one instead of two identification sequences, as described in DE 10 2011 118 018), includes a PacI restriction site, which is flanked by recombinase recognition sequences of the parA resolvase and an expression cassette of the parA resolvase outside the recombinase recognition sequences. This plasmid is cut with the enzyme PacI (Article No. R0547L, NEB, Frankfurt, Germany) and dephosphorylated with alkaline phosphatase (Article No. M0290L, NEB, Frankfurt, Germany). Thereafter, the fragment is ligated with T4 ligase into the linearized vector to obtain PP.MD2G (FIG. 19).

Example 7

Production of Minicircles from the Parental Plasmids PP.ssGFP, PP.DG, PP.PD2rs, PP.scGFP, PP.DM and PP.MD2G The cultivation is carried out at 37° C. in an MBR bioreactor (MBR BIO REACTOR, Switzerland) with a total volume of 7 liters at a filling quantity/volume of 5 liters. The adjustment of the pH to pH 7 is carried out using 2 M sodium hydroxide and 2 M phosphoric acid. The flow rate of air is set to 5 liter/min. The oxygen concentration (60%) is controlled by varying the stirrer speed within the range of 500 to 2000 per minute. LB medium is used without addition of antibiotics. The method is carried out with each of the six parental plasmids.

The bioreactor is inoculated with 50 ml of a preculture of *E. coli* K12 transformed with parental plasmid and cultured for about 15 hours at 28° C. The precultures are grown under selective conditions with the addition of 75 mg/ml kanamycin. The LB medium preculture is enriched with glucose to prevent a premature expression of parA resolvase, which is under the control of the $P_{BAD}$ promoter.

The expression of the parA resolvase will be induced by the addition of L-arabinose to the medium at an $OD_{600}$ of 3.5 to 5.0. After one hour of additional growth, the cells are harvested by centrifugation for 6 minutes at 9039 g, transferred to storage bags, frozen and stored at −20° C. before the recombination products are purified.

During culturing in the bioreactor, samples are removed and stored at 4° C. for further analysis. The $OD_{600}$ is measured and the plasmids are purified (NucleoBond® PC 100, Macherey-Nagel, Düren) to determine the plasmid yield and recombination efficiency.

From the obtained biomass, the recombination products minicircle and miniplasmid are purified using commercially available plasmid isolation kits (NucleoBond® PC 10000, Macherey & Nagel, Düren).

For the isolation of the minicircle from the mixture of miniplasmids and minicircles, we used a specific affinity chromatography. For this purpose, a biotinylated repressor of the lactose operon is coupled to streptavidin-Sepharose High Performance (GE Healthcare) (cf. Mayrhofer, et al., *J. Gene Med.* 2008, 10 (11):1253-1269).

5 ml of this chromatography matrix is used to fill a XK 16 chromatography column and equilibrated with five column volumes 50 mM Tris pH 8, 400 mM NaCl. The recombination product mixture (1 mg/ml in 50 mM Tris pH 8, 400 mM NaCl) is subsequently applied to the column material (GE Healthcare) at a flow rate of 0.5 ml/min over in an ÄKTA-system. The column is washed with 50 mM Tris pH 8, 400 mM NaCl at a flow rate of 1 ml/min until the $UV_{260\,nm}$ signal detected at the device drops to a stable baseline. Now, the minicircle DNA is eluted with 50 mM Tris pH 8, 500 mM NaCl, 5 mM IPTG and afterwards the column is washed with 50 mM Tris pH 8, 1 M NaCl and 50 mM Tris pH 8 and again equilibrated for further use.

The DNA is extracted from the high-salt mixture by precipitation and finally resuspended in water.

Figure 3:
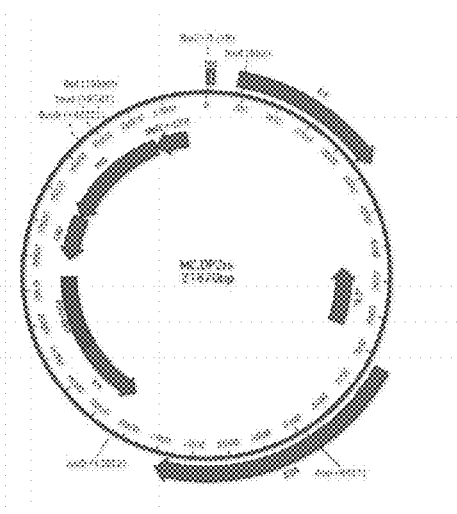
FIG. 3 shows the map of the minicircle MC.DP2rs. "Rec" in this case represents the recombined recombinase recognition sequence that remains in the minicircle following recombination. Some singular interfaces are included for guidance.
Figure 4:
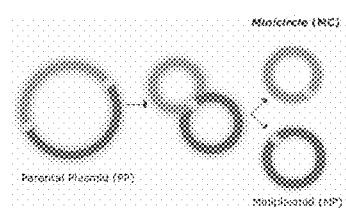
FIG. 4 schematically shows the generation of miniplasmid and minicircle from a parental plasmid.
Figure 5:
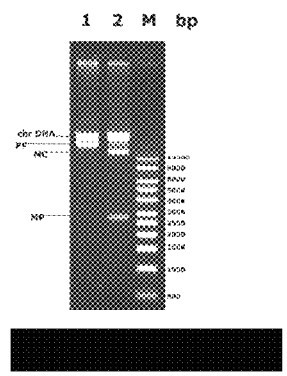
FIG. 5 shows an agarose gel with undigested monomeric PP.DP2rs (PP) (lane 1), undigested monomeric MC.DP2rs (MC) and undigested monomeric mini-plasmid (bottom: MP) (both lane 2) compared to a DNA size standard of linear DNA fragments of defined length (1 Kb ladder, PlasmidFactory, Bielefeld; rounded to the ladder size specifications of the entire 500 by provided on the right of the gel). Chr DNA=bacterial chromosomal DNA from a kit grade DNA extraction.
Figure 8:
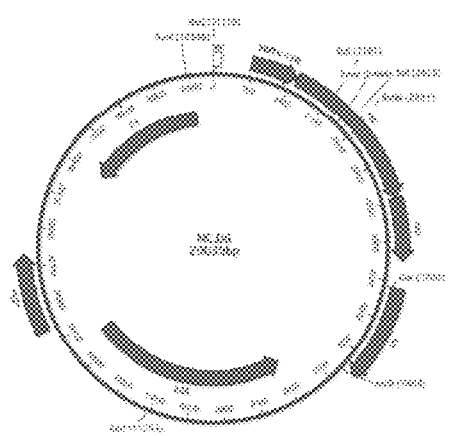
FIG. 8 shows the map of the minicircle MC.DG. "Rec" in this case represents the recombined recombinase recognition sequence that remains in the minicircle following recombination. Some singular restriction sites are included for guidance.
Figure 11:
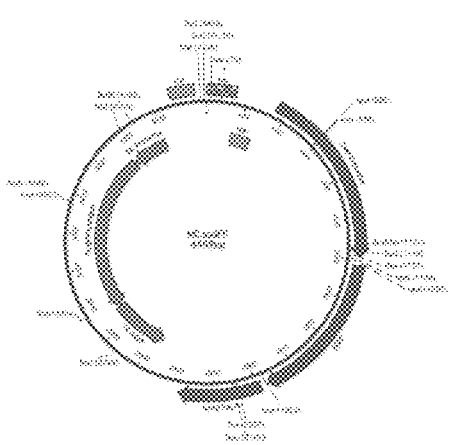
FIG. 11 shows the map of the minicircle MC.ssGFP. "rec" in this case represents the recombined recombinase recognition sequence that remains in the minicircle following recombination. Some singular restriction sites are included for guidance.
Figure 14:
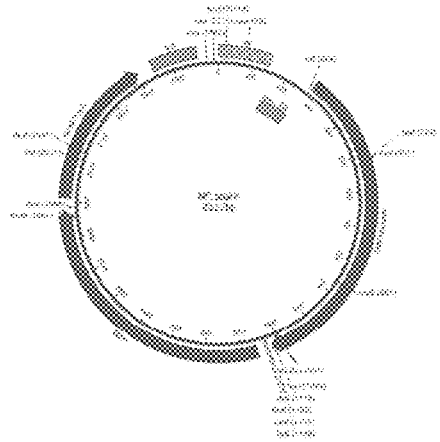
FIG. 14 shows the map of the minicircle MC.scGFP. "Rec" in this case represents the recombined recombinase recognition sequence that remains in the minicircle following recombination. Some singular restriction sites are included for guidance.
Figure 17:
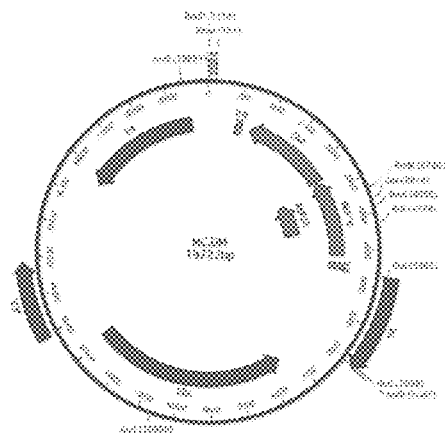
FIG. 17 shows the map of the minicircle MC.DM. "rec" in this case represents the recombined recombinase recognition sequence that remains after recombination in the minicircle. Other elements are described in FIG. 17. Some singular restriction sites are included for guidance.
Figure 20:
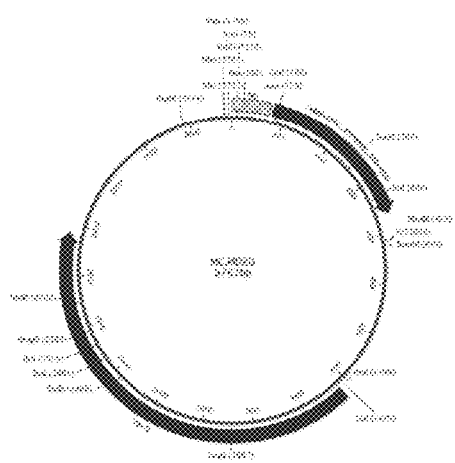
FIG. 20 shows the map of the minicircle MC.MD2G. "rec" in this case represents the recombined recombinase recognition sequence that remains after recombination in the minicircle. The other elements correspond to those in FIG. 18. Some singular restriction sites are included for guidance.
Figure 21:
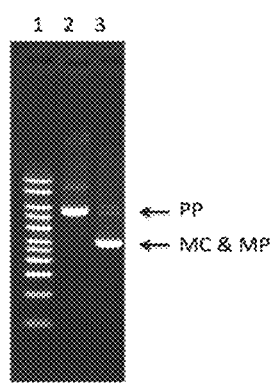
FIG. 21 shows an agarose gel with undigested monomeric PP.ssGFP (PP) (lane 2) and undigested monomeric MC.ssGFP (MC) and undigested monomeric miniplasmid (MP) (lane 3). MP and MC appear as a double band due to the approximate same size. For comparison, a DNA size standard from linear DNA fragments is provided (1 kbp ladder, PlasmidFactory, Bielefeld).

The DNA of the minicircles MC.ssGFP (FIG. 11) MC.DG (FIG. 8) MC.DP2rs (FIG. 3) MC.scGFP (FIG. 14) MC.DM (FIG. 17) and MC .MD2G (FIG. 20) are each adjusted to a concentration of 1 mg/ml.

The generated minicircles are then subjected to quality control. Tests for appearance (clear solution without particles), DNA concentration (using UV absorption at 260 nm), DNA purity (by UV scan from 220 to 320 nm), the correct minicircle identity (using restriction digestion and agarose gel electrophoresis), the absence of RNA and bacterial chromosomal DNA (using visual inspection after gel electrophoresis), DNA-homogeneity (using capillary gel) and the endotoxin concentration (using Limulus amoebocyte lysate test) are conducted.

Example 8

Production of AAV Vectors Using MC.ssGFP and MC.DP2rs $7.5 \times 10^6$ 293-cells were seeded in a 15 cm Petri dish containing 25 ml DMEM with Glutamax plus 10% fetal calf serum (Invitrogen) and 1% penicillin/streptomycin (Invitrogen) and cultured for 24 hours. For the production of larger amounts, several such batches were prepared. At approximately 80% confluence, the medium was changed to 25 ml DMEM with Glutamax plus 10% fetal calf serum and 1% penicillin/streptomycin. After an additional 2 hours, the transfection of the cells was carried out using the calcium phosphate method. Therefore, 31.9 µg DNA (containing 4.3 µg MC.ssGFP and 27.6 µg MC.DP2rs in a 1:1 molar ratio) are added to 1 ml of 250 mM $CaCl_2$ and mixed. Afterwards, 1 ml HBS buffer is added dropwise (pH 7.29, 5.955g HEPES, 8.18 g NaCl, 1.5 ml of $Na_2HPO_4$ in 400 ml final volume) and then briefly mixed. After 2 minutes of incubation, the solution is added to the cells. After continuing the cultivation, 24 hours later, the medium was changed to 20 ml Dulbecco's Modified Eagle Medium (DMEM, Invitrogen) with Glutamax plus 2% fetal calf serum and 1% penicillin/streptomycin. Another 24 hours later the cells were harvested by scraping and centrifuged at 3000×g. The supernatant was discarded and the pellet resuspended in 7.5 ml lysis buffer (150 mM NaCl, 50 mM Tris/HCl, pH 8.5). The cells were disrupted by three rounds of freezing in liquid nitrogen and then thawing at 37° C. in a water bath. Cellular DNA and RNA, as well as any remaining plasmid DNA was removed by a benzonase treatment (50U benzonase per ml suspension, 30 minutes, 37° C.). The suspension was then centrifuged for 20 minutes at 3700×g and the supernatant was transferred to a sterile ultracentrifuge tube. The separation of cellular proteins was performed via an iodixanol gradient centrifugation (Peng et al., *Anal. Biochem.* 2006, 354(1):140-147) followed by gel filtration (also by Peng et al. 2006).

Example 9

Production of AAV Vectors with Help from MC.ssGFP and MC.DG $7.5 \times 10^6$ 293 cells were seeded in a 15 cm Petri dish containing 25 ml DMEM with Glutamax plus 10% fetal calf serum (Invitrogen) and 1% penicillin/streptomycin (Invitrogen) and cultured for 24 hours. For the production of larger amounts, several such batches were prepared. At approximately 80% confluence, the medium was changed to 25 ml DMEM with Glutamax plus 10% fetal calf serum and 1% penicillin/streptomycin. After an additional 2 hours, the transfection of the cells was carried out using the calcium phosphate method. Therefore, 31.9 µg DNA (containing 4.3 µg MC.ssGFP and 27.6 λg MC.DG in a 1:1 molar ratio) are added to 1 ml of 250 mM $CaCl_2$ and mixed. Afterwards, 1 ml HBS buffer is added dropwise (pH 7.29, 5.955 g HEPES, 8.18 g NaCl, 1.5 ml of $Na_2HPO_4$ in 400 ml final volume) and then briefly mixed. After 2 minutes of incubation, the solution is added to the cells. After continuing the cultivation, 24 hours later, the medium was changed to 20 ml Dulbecco's Modified Eagle Medium (DMEM, Invitrogen) with Glutamax plus 2% fetal calf serum and 1% penicillin/streptomycin. Another 24 hours later the cells were harvested by scraping and centrifuged at 3000×g. The supernatant was discarded and the pellet resuspended in 7.5 ml lysis buffer (150 mM NaCl, 50 mM Tris/HCl, pH 8.5). The cells were disrupted by three rounds of freezing in liquid nitrogen and then thawing at 37° C. in a water bath. Cellular DNA and RNA, as well as any remaining plasmid DNA was removed by a benzonase treatment (50U benzonase per ml suspension, 30 minutes, 37° C.). The suspension was then centrifuged for 20 minutes at 3700×g and the supernatant was transferred to a sterile ultracentrifuge tube. The separation of cellular proteins was performed via an iodixanol gradient centrifugation (Peng et al., *Anal. Biochem.* 2006, 354(1):140-147) followed by gel filtration (also by Peng et al. 2006).

This experiment produced the same results observed in Example 5.

Example 10

Production of AAV Vectors with Help from pssGFP and MC.DP2rs $7.5 \times 10^6$ 293 cells were seeded in a 15 cm Petri dish in 25 ml DMEM with Glutamax plus 10% fetal calf serum (Invitrogen) and 1% penicillin/streptomycin (Invitrogen) and cultured for 24 hours. For the production of larger amounts, several such batches were prepared. At approximately 80% confluence, the medium was changed to 25 ml DMEM with Glutamax plus 10% fetal calf serum and 1% penicillin/streptomycin. After an additional 2 hours, the transfection of the cells was carried out using the calcium phosphate method. Therefore 35.1 µg DNA (containing 7.5 µg pssGFP and 27.6 µg MC.DP2rs in a 1:1 molar ratio) are added to 1 ml of 250 mM $CaCl_2$ and mixed. Afterwards, 1 ml HBS buffer is added dropwise (pH 7.29, 5.955 g HEPES, 8.18 g NaCl, 1.5 ml of $Na_2HPO_4$ in 400 ml final volume) and then briefly mixed. After 2 minutes of incubation, the solution is added to the cells. After continuing the cultivation, 24 hours later, the medium was changed to 20 ml Dulbecco's Modified Eagle Medium (DMEM, Invitrogen) with Glutamax plus 2% fetal calf serum and 1% penicillin/streptomycin. Another 24 hours later the cells were harvested by scraping and centrifuged at 3000×g. The supernatant was discarded and the pellet resuspended in 7.5 ml lysis buffer (150 mM NaCl, 50 mM Tris/HCl, pH 8.5). The cells were disrupted by three rounds of freezing in liquid nitrogen and then thawing at 37° C. in a water bath. Cellular DNA and RNA, as well as any remaining plasmid DNA was removed by a benzonase treatment (50 U benzonase per ml suspension, 30 minutes, 37° C.). The suspension was then centrifuged for 20 minutes at 3700 ×g and the supernatant was transferred to a sterile ultracentrifuge tube. The separation of cellular proteins was performed via an iodixanol gradient centrifugation (Peng et al., *Anal. Biochem.* 2006, 354(1):140-147) followed by gel filtration (also by Peng et al. 2006).

This experiment produced the same results observed in Example 5.

Example 11

Production of AAV Vectors Using MC.ssGFP and pDP2rs $7.5 \times 10^6$ 293 cells were inoculated in a 15 cm Petri dish in 25 ml DMEM with Glutamax plus 10% fetal calf serum (Invitrogen) and 1% penicillin/streptomycin (Invitrogen) and cultured for 24 hours. For the production of larger amounts, several such batches were prepared. At approximately 80% confluence, the medium was changed to 25 ml DMEM with Glutamax plus 10% fetal calf serum and 1% penicillin/streptomycin. After an additional 2 hours, the transfection of the cells was carried out using the calcium phosphate method. Therefore, 34.3 µg DNA (containing 4.3 µg MC.ssGFP and 30 µg pDP2rs in a 1:1 molar ratio) are added to 1 ml of 250 mM $CaCl_2$ and mixed. Subsequently, 1 ml HBS buffer is added dropwise (pH 7.29, 5.955 g HEPES, 8.18 g NaCl, 1.5 ml of $Na_2HPO_4$ in 400 ml final volume) and then briefly mixed. After 2 minutes of incubation, the solution is added to the cells. After continuing the cultivation, 24 hours later, the medium was changed to 20 ml Dulbecco's Modified Eagle Medium (DMEM, Invitrogen) with Glutamax plus 2% fetal calf serum and 1% penicillin/streptomycin. Another 24 hours later the cells were harvested by scraping and centrifuged at 3000×g. The supernatant was discarded and the pellet resuspended in 7.5 ml lysis buffer (150 mM NaCl, 50 mM Tris/HCl, pH 8.5). The cells were disrupted by three rounds of freezing in liquid nitrogen and then thawing at 37° C. in a water bath. Cellular DNA and RNA, as well as any remaining plasmid DNA was removed by a benzonase treatment (50 U benzonase per ml suspension, 30 minutes, 37° C.). The suspension was then centrifuged for 20 minutes at 3700 ×g and the supernatant was transferred to a sterile ultracentrifuge tube. The separation of cellular proteins was performed via an iodixanol gradient centrifugation (Peng et al., *Anal. Biochem.* 2006, 354(1):140-147) followed by gel filtration (also by Peng et al. 2006).

This experiment produced the same results observed in Example 5.

Example 12

Production of Lentiviral Vectors with Help from MC.MD2G, MC.CMVdR8.74 and MC.HRsinpptSEW

For the production of lentiviral vectors, a triple-transfection system was used, wherein the packaging sequences are located on two packaging vectors. All three vectors were minicircles. As a first packaging vector, the above-disclosed minicircle MC.MD2G encoding the env protein of vesicular stomatitis virus (VSV) was used. As a second packaging vector, MC.CMVdR8.74 was used. This minicircle has 7472 bp and encodes the proteins gag-pol, rev, and tat of HIV-1. As a transfer vector, minicircle MC.HRsinpptSEW was used, which has 5351 bp and encodes GFP. The minicircles MC.C-MVdR8.74 and MC.HRsinpptSEW are derived from the plasmids pCMVΔR8.74 or pHRsinpptSEW, respectively, as described in Natarajan et al. (*Neurogastroenterology & Motility* 2014 26: 1513-1518). The vector preparation is based on methods described in this article, except that minicircles instead of conventional plasmids were used. 80% confluent 293T cells were transfected for 4 h with 22.15 µg MC.HRsinpptSEW, 6.47 µg MC.MD2G and 18.80 µg MC.C-MVdR8.74. The viral particles were harvested after 36 hours, filtered and stored frozen.

Example 13

Comparison of the Efficiency of Cotransfection Between the Methods According to the State of the Art (Co-Transfection of Only Plasmid-Based DNA) and Solely or Partially Minicircle-Based DNA for AAV Production Using the "Two-Plasmid System".

The production efficiency of viral AAV particles using minicircle packaging vector MC.PG2rs and minicircle transfer vector MC.ssGFP in co-transfection (see Example 5), preferably with the help of minicircle packaging vector MC.PG2rs and plasmid transfer vector pssGFP (see Example 7), results in increased viral titers in an equimolar comparison to conventional production using plasmid-based co-transfection (plasmid transfer vector and packaging plasmid vector). By using equimolar quantities of minicircle DNA, the total amount of DNA used is reduced and a decreased (DNA-based) toxicity is achieved.

Example 14

Comparison of the Efficiency of Cotransfection Between the Methods According to the State of the Art (Co-Transfection of Only Plasmid-Based DNA) and Partially Minicircle-Based DNA for AAV Production Using the "3-Plasmid System".

The production efficiency of AAV virus particles with help from plasmid DNA-based helper-/packaging functions in a triple transfection was tested in a manner similar to that set forth in Examples 5-8. For transfection, 7.5 µg pRC and 22.5 µg pXX6-80 (J. Rabinowitz et al., *J. Virol.* 2002, 76:791-801.) and 4.3 µg of a minicircle transfer vector containing a stuffer sequence as shown in FIG. 22B was used. Compared to conventional production using plasmid-based co-transfection, this method results in comparable virus titers using less quantities of inserted DNA.

Example 15

Comparison of the Production of Recombinant AAV Viral Particles Using the "Two-Plasmid System" and Their Quality Analysis in Terms of Their Productivity and Free From Undesired Bacterial Sequences.

4 different DNA preparations (plasmid pDP2rs, plasmid pssGFP, minicircle MC.DP2rs, minicircle MC.ssGFP) were mixed in 4 possible combinations and in equimolar amounts and used for cotransfection as described above. In addition, transfections were carried out in two control batches, in which no transfer plasmid (pssGFP) or no transfer minicircle (MC-ssGFP) was added. The amounts of DNA used in each case are set forth in Table 1:

TABLE 1

The amount of plasmid applied for transfection in the experiments of Example 15.

| Approach No. | pDP2rs | pssGFP | MC.DP2rs | MC.ssGFP |
|---|---|---|---|---|
| 2720-1 | 120 µg | 30 µg | | |
| 2720-2 | 120 µg | 30 µg | | |
| 2721-1 | 120 µg | | | 17.2 µg |
| 2721-2 | 120 µg | | | 17.2 µg |
| 2722-1 | | 30 µg | 110.4 µg | |
| 2722-2 | | 30 µg | 110.4 µg | |
| 2723-1 | | | 110.4 µg | 17.2 µg |
| 2723-2 | | | 100 µg | 15.6 µg |
| 2724 | | | 110.4 µg | |
| 2725 | 120 µg | | | |

Thus, both the combination exclusively containing plasmid vectors (2720-1 and 2720-2), or of mixtures of plasmid and minicircle (2721-1 and 2721-2 for the packaging vector as plasmid and the transfer vector as minicircle, according to Example 9; 2722-1 and 2722-2 for the packaging vector as minicircle and the transfer vector as plasmid as described in Example 10), as was the exclusive combination of minicircle vectors and (2723-1 and 2723-2, according to Example 8) were tested.

During the production of recombinant AAV particles, the skilled person knows that empty as well as fully infectious and fully non-infectious particles are formed. Moreover, more than one infectious virus particle is always required to successfully infect a cell, preferably the infection is achieved by receptor-mediated endocytosis. Thus, there is a dependency on the cell to be infected. In the present example, HeLa cells were used.

Titers of filled particles (genomic titer) were measured by quantitative PCR and capsid titers were measured using ELISA. From the ratio of genomic titer to capsid titer, one can computationally calculate the packaging efficiency. The transduction titer, which corresponds to the number of infectious particles, is determined by FACS analysis. Results are shown in Table 2.

TABLE 2

Packaging efficiency and transduction titer of the viral vectors from Example 15.

| Approach No. | Genomic titer | Capsid titer | Packaging efficiency | Transduction titer |
|---|---|---|---|---|
| 2720-1 | $3.96 \cdot 10^{11}$ | $8.25 \cdot 10^{11}$ | 0.50 | $2.50 \times 10^9$ |
| 2720-2 | $3.70 \cdot 10^{11}$ | $5.77 \cdot 10^{11}$ | 0.64 | $1.04 \cdot 10^9$ |
| 2721-1 | $9.82 \cdot 10^{11}$ | $1.01 \times 10^{12}$ | 0.97 | $4.53 \cdot 10^9$ |
| 2721-2 | $3.96 \cdot 10^{11}$ | $7.44 \cdot 10^{11}$ | 0.53 | $2.91 \cdot 10^9$ |
| 2722-1 | $3.70 \cdot 10^{11}$ | $8.85 \cdot 10^{11}$ | 0.42 | $7.90 \times 10^8$ |
| 2722-2 | $1.75 \times 10^{11}$ | $8.59 \cdot 10^{11}$ | 0.20 | $6.32 \times 10^8$ |
| 2723-1 | $4.82 \cdot 10^{11}$ | $8.01 \cdot 10^{11}$ | 0.60 | $2.64 \cdot 10^9$ |
| 2723-2 | $5.70 \cdot 10^{11}$ | $9.25 \cdot 10^{11}$ | 0.62 | $1.56 \cdot 10^9$ |

Figure 24:
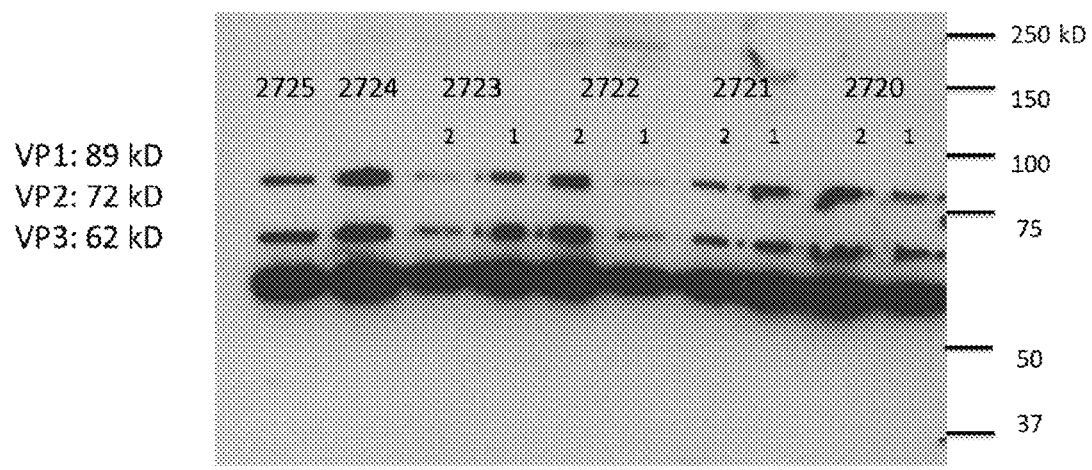
FIG. 24 shows a Western Blot of capsid proteins resulting from the experiment set forth in Example 15.

Using Western blotting, the presence of the 3 leader proteins VP1 (89 kDa) (72 kD) VP2 (72 kDa) and VP3 (62 kD) was detected (see FIG. 24). The size and the ratio of the capsid proteins (VP1:VP2:VP3=1:1:10) was correct in all cases. All of the data indicate that the use of minicircle DNA in the comparisons performed herein, and with HeLa cells, is at least as reliably suitable for the production of recombinant viral AAV particles as plasmid-based systems.

Table 3 shows the essential aspects of the system: We investigated in which AAV preparations bacterial sequences would still occur, and which have passed into viral particles through false packaging thereby representing a risk for the pharmaceutical use of these vectors. Quantitative PCR detection of ampicillin resistance sequences in the preparations was carried out.

TABLE 3

Number of PCR cycles required until detection of ampicillin resistance sequences and calculated number of sequences per micro liter of preparation.

| No Approach No. | Required number of PCR cycles | Particle count per µl |
| --- | --- | --- |
| 2720-1 | 22.04 | $9.74 \times 10^5$ |
| 2720-2 | 21.55 | $1.40 \times 10^6$ |
| 2721-1 | 26.17 | $3.12 \times 10^4$ |
| 2721-2 | 27.26 | $1.14 \times 10^4$ |

TABLE 3-continued

Number of PCR cycles required until detection of ampicillin resistance sequences and calculated number of sequences per micro liter of preparation.

| No Approach No. | Required number of PCR cycles | Particle count per µl |
| --- | --- | --- |
| 2722-1 | 21.23 | $1.78 \times 10^6$ |
| 2722-2 | 22.71 | $5.80 \times 10^5$ |
| 2723-1 | 30.86 | $3.08 \times 10^2$ |
| 2723-2 | 31.14 | $2.28 \times 10^2$ |
| 2724 | 30.92 | $2.90 \times 10^2$ |
| 2725 | 28.92 | $2.26 \times 10^3$ |
| $H_2O$ | 31.64 | |

The negative control using water demonstrates the system background (>30 cycles). All preparations in which plasmid-based DNA components were involved (2720-1 and 2720-2, 2721-1 and 2721-2, 2722-1 and 2722-2) revealed high contamination rates. In the case of combination 2721-1 and 2721-2 (for the packaging vector as plasmid and the transfer vector as minicircle according to Example 9), this effect is significantly reduced, but still too strong to support a safe medical use. Here, the source of the contamination is on the large packaging vector and not on the transfer vector. Only when using no plasmid DNA (both components on a minicircle basis), the ampicillin-resistance sequences no longer exist and are thus not packed—despite this, excellent viral titers are achieved.

The invention claimed is:

1. A minicircle transfer vector comprising:
   a. a transfer sequence; and
   b. specific packaging signals flanking each respective end of the transfer sequence region for mediating the packaging of the transfer sequence into one or more viral vector particles.

2. The minicircle transfer vector according to claim 1, wherein the viral vector particle is AAV or a retrovirus.

3. The minicircle transfer vector according to claim 1, wherein the transfer sequence comprises an expression cassette comprising at least one gene, at least one siRNA- or shRNA-encoding sequence, at least one insulator sequence, or a combination thereof.

4. The minicircle transfer vector according to claim 1, wherein said minicircle transfer vector comprises at least one stuffer sequence within the transfer sequence region flanked by the specific packaging signals, or wherein said minicircle transfer vector comprises at least one stuffer sequence external to said transfer sequence region flanked by the specific packaging signals, or a combination thereof.

5. The minicircle transfer vector according to claim 1, further comprising at least one packaging expression cassette, wherein on the at least one packaging expression cassette all packaging proteins necessary for the packaging of the transfer sequence into the one or more viral vector particles are encoded.

6. A minicircle packaging vector comprising at least one packaging expression cassette,
   wherein on the at least one packaging expression cassette at least one protein necessary for the packaging of a transfer sequence into the one or more viral vector particles is encoded.

7. The minicircle packaging vector according to claim 6, wherein on the at least one packaging expression cassette all proteins necessary for the packaging of the transfer sequence into the one or more viral vector particles are encoded.

8. The minicircle packaging vector according to claim 6, wherein the viral vector particle is AAV or a retrovirus.

9. An isolated cell comprising the minicircle transfer vector according to claim 1.

10. A method for producing a viral vector particle, the method comprising:
   a. transfrecting:
      i. a eukaryotic cell using a minicircle transfer vector of claim 1, and at least one packaging vector comprising at least one packaging expression cassette, wherein on the at least one expression cassette all packaging proteins necessary for the packaging of the transfer sequence into the one or more viral vector particles are encoded for subsequent expression, or a minicircle packaging vector according to claim 6 and one or more sequences encoding the remaining proteins necessary for the packaging of the transfer sequence into the one or more viral vector particles; or
      ii. a eukaryotic using a transfer vector comprising a transfer sequence, and at least one minicircle packaging vector according to claim 6 and one or more sequences encoding the remaining proteins necessary for the packaging of the transfer sequence into the one or more viral vector particles; or
      iii. a cell with a minicircle vector according to claim 5; and
   b. expressing the at least one packaging expression cassette; and
   c. packaging the transfer sequence into the viral vector particle.

11. The method according to claim 10, wherein a single packaging vector is used in step (a)(i) and (a)(ii).

12. The method according to claim 10, wherein in step (a)(i) and (a)(ii), transfecting with the transfer vector and the one or more packaging vectors, respectively:
   a. is performed simultaneously in a co-transfection; or
   b. wherein transfecting with the transfer vector is performed prior to transfecting with one or more packaging vectors, respectively; or
   c. wherein transfecting with the transfer vector is performed after transfecting with one or more packaging vectors, respectively.

13. The method according to claim 10, wherein in step (a)(i) and (a)(ii), respectively, transfecting with one or more packaging vectors is performed first and the packaging vector remains episomally stable in the stable in the eukaryotic cell, and wherein in step (a)(i) and (a)(ii), respectively, transfecting with the transfer vector is performed with said eukaryotic cell.

14. The method according to claim 10, wherein the eukaryotic cell is a mammalian cell.

15. A kit for producing viral vector particles comprising one or more of the following components:
   a. a minicircle transfer vector according to claim 1, and at least one packaging vector comprising one of the following:
      at least one packaging expression cassette, wherein on the at least one expression cassette at least one protein necessary for the packaging of the transfer sequence into the one or more viral vector particles are encoded, or a minicircle packaging vector according to claim 6; or
   b. a transfer vector comprising a transfer sequence and at least one minicircle packaging vector according to claim 6; or
   c. a minicircle vector according to claim 5.

16. The kit of claim 15, wherein the at least one minicircle packaging vector according to steps (a) and (b) is a minicircle vector according to claim 7.

17. The kit of claim 15, wherein the viral vector particle is AAV or a retrovirus.

18. The method according to claim 11, wherein said vector is a minicircle vector according to claim 7.

19. The method according to claim 10, further comprising isolating the produced viral vector particle from the eukaryotic cell, or from the medium in which said viral vector particle is located.

\* \* \* \* \*

SEQUENCE LISTING

```
<160> NUMBER OF SEQ ID NOS: 9

<210> SEQ ID NO 1
<211> LENGTH: 23677
<212> TYPE: DNA
<213> ORGANISM: Artificial Sequence
<220> FEATURE:
<223> OTHER INFORMATION: Synthesized in laboratory

<400> SEQUENCE: 1
ggatccgaat tcttaattaa catcatcaat aatataccctt attttggatt gaagccaata      60
tgataatgag ggggtggagt ttgtgacgtg gcgcggggcg tgggaacggg gcgggtgacg     120
tagtagtgtg gcggaagtgt gatgttgcaa gtgtggcgga acacatgtaa gcgacggatg     180
tggcaaaagt gacgttttg gtgtgcgccg gtgtacacag gaagtgacaa ttttcgcgcg     240
gttttaggcg gatgttgtag taaatttggg cgtaaccgag taagatttgg ccattttcgc     300
gggaaaactg aataagagga agtgaaatct gaataatttt gtgttactca tagcgcgtaa     360
tatttgtcta gggccgcggg gactttgacc gtttacgtgg agactcgccc aggtgttttt     420
ctcaggtgtt ttccgcgttc cgggtcaaag ttggcgtttt attattatag tcaggggat     480 cctctagaac tagtggatcc gtccctcagg cctagaagta aaaaagggaa aaaagagtgt     540
gtttgtcaaa ataggagaca ggtggtggca accaaggact tatagggggac cttacatcta     600 cagaccaaca gatgcccct taccatatac aggaagatat gacttaaatt gggataggtg     660
ggtcacaatc aacggctata aagtgttata cagatccctc ccctccctt tcgtgaaaga     720 ctcgccagag ctagacctcc ttggtgtatg ctaactgaga agagaaagac gacatgaaac     780
aacaggtaca tgattatatt tatctaggaa caggaatgca cttttgggga aaggttttcc     840
ataccaagga aggggcagtg gctggactga tagaacatta ttctgcaaaa acttatggta     900
tgagttatta tgattagcct ttatttgccc aaccttgcgg ttcccagggt ttaaataagt     960
```

```
ttatggttac aaactgttct taaaacgagg atgtgagaca agtggtttcc tgacttggtt    1020
tggtaatcaa atgttctgat ctgagctctt agtgttctat tttcctatgt tcttttggaa    1080
tctatccaag tcttatgtaa atgcttatgt aaaccataat ataaagagt gctgattttt     1140 tgagtaaact tgcaacagtc ctaacattct tctctcgtgt gtttgtgtct gttcgccatc    1200
ccgtctccgc tcgtcactta tccttcactt ttcagagggt ccccccgcag atcccggtca    1260
ccctcaggtc gggacctgca gaagacgccc gagtgagcac gcagggtctc cattttgaag    1320
cgggaggttt gaacgcgcag ccgccatgcc ggggttttac gagattgtga ttaaggtccc    1380
cagcgacctt gacgggcatc tgcccggcat tctgacagc tttgtgaact gggtggccga     1440
gaaggaatgg gagttgccgc cagattctga catggatctg aatctgattg agcaggcacc    1500
cctgaccgtg gccgagaagc tgcagcgcga ctttctgacg gaatggcgcc gtgtgagtaa    1560
ggccccggag gcccttttct ttgtgcaatt tgagaaggga gagagctact tccacatgca    1620
cgtgctcgtg gaaaccaccg gggtgaaatc catggttttg ggacgttttcc tgagtcgat    1680 tcgcgaaaaa ctgattcaga gaatttaccg cgggatcgag ccgactttgc caaactggtt    1740
cgcggtcaca aagaccagaa atggcgccgg aggcgggaac aaggtggtgg atgagtgcta    1800
catccccaat tacttgctcc ccaaaaccca gcctgagctc cagtgggcgt ggactaatat    1860
ggaacagtat ttaagcgcct gtttgaatct cacggagcgt aaacggttgg tggcgcagca    1920
tctgacgcac gtgtcgcaga cgcaggagca gaacaaagag aatcagaatc ccaattctga    1980
tgcgccggtg atcagatcaa aaacttcagc caggtacatg gagctggtcg ggtggctcgt    2040
ggacaagggg attacctcgg agaagcagtg gatccaggag gaccaggcct catacatctc    2100
cttcaatgcg gcctccaact cgcggtccca aatcaaggct gccttggaca atgcgggaaa    2160
gattatgagc ctgactaaaa ccgccccga ctacctggtg ggccagcagc ccgtggagga     2220
catttccagc aatcggattt ataaaatttt ggaactaaac gggtacgatc cccaatatgc    2280
ggcttccgtc tttctgggat gggccacgaa aaagttcggc aagaggaaca ccatctggct    2340
gtttgggcct gcaactaccg ggaagaccaa catcgcggag gccatagccc acactgtgcc    2400
cttctacggg tgcgtaaact ggaccaatga gaactttccc ttcaacgact gtgtcgacaa    2460
gatggtgatc tggtgggagg aggggaagat gaccgccaag gtcgtggagt cggccaaagc    2520
cattctcgga ggaagcaagg tgcgcgtgga ccagaaatgc aagtcctcgg cccagataga    2580
cccgactccc gtgatcgtca cctccaacac caacatgtgc gccgtgattg acgggaactc    2640
aacgaccttc gaacaccagc agccgttgca agaccggatg ttcaaatttg aactcacccg    2700
ccgtctggat catgactttg ggaaggtcac caagcaggaa gtcaaagact ttttccggtg    2760
ggcaaaggat cacgtggttg aggtggcagca tgaattctac gtcaaaaagg gtggagccaa    2820
gaaaagaccc gcccccagtg acgcagatat aagtgagccc aaacgggtgc gcgagtcagt    2880
tgcgcagcca tcgacgtcag acgcggaagc ttcgatcaac tacgcagaca ggtaccaaaa    2940
caaatgttct cgtcacgtgg gcatgaatct gatgctgttt ccctgcagac aatgcgagag    3000
aatgaatcag aattcaaata tctgcttcac tcacggacag aaagactgtt tagagtgctt    3060 tccccgtgtca aatctcaac ccgtttctgt cgtcaaaaag gcgtatcaga aactgtgcta     3120
cattcatcat atcatgggaa aggtgccaga cgcttgcact gcctgcgatc tggtcaatgt    3180
ggatttggat gactgcatct ttgaacaata aatgatttaa atcaggtatg gctgccgatg    3240
gttatcttcc agattggctc gaggacactc tctctgaagg aataagacag tggtggaagc    3300
```

```
tcaaacctgg cccaccacca ccaaagcccg cagagcggca taaggacgac agcagggtc    3360
ttgtgcttcc tgggtacaag tacctcggac ccttcaacgg actcgacaag ggagagccgg   3420
tcaacgaggc agacgccgcg gccctcgagc acgtacaaag cctacgaccg gcagctcgac   3480
agcggagaca cccgtacct caagtacaac acgccgacg cggagtttca ggagcgcctt    3540
aaagaagata cgtcttttgg gggcaacctc ggacgagcag tcttccaggc gaaaaagagg   3600
gttcttgaac ctctgggcct ggttgaggaa cctgttaaga cggctccggg aaaaaagagg   3660
ccggtagagc actctcctgt ggagccagac tcctcctcgg gaaccggaaa ggcgggccag   3720
cagcctgcaa gaaaaagatt gaattttggt cagactggag acgcagactc agtacctgac   3780
ccccagcctc tcggacagcc accagcagcc cctctggtc tgggaactaa tacgatggct    3840
acaggcagtg gcgcaccaat ggcagacaat aacgagggcg ccgacggagt gggtaattcc   3900
tccggaaatt ggcattgcga ttccacatgg atgggcgaca gagtcatcac caccagcacc   3960
cgaacctggg ccctgcccac ctacaacaac cacctctaca aacaaatttc cagccaatca   4020
ggagcctcga acgacaatca ctactttggc tacagcaccc cttgggggta ttttgacttc   4080
aacagattcc actgccactt ttcaccacgt gactggcaaa gactcatcaa caacaactgg   4140
ggattccgac ccaagagact caacttcaag ctctttaaca ttcaagtcaa agaggtcacg   4200
cagaatgacg gtacgacgac gattgccaat aaccttacca gcacggttca ggtgtttact   4260
gactcggagt accagctccc gtacgtcctc ggctcggcgc atcaaggatg cctcccgccg   4320
ttcccagcag acgtcttcat ggtgccacag tatggatacc tcaccctgaa caacgggagt   4380
caggcagtag gacgctcttc attttactgc ctggagtact tccttctca gatgctgcgt    4440
accggaaaca actttacctt cagctacact tttgaggacg ttccttttcca cagcagctac   4500
gctcacagcc agagtctgga ccgtctcatg aatcctctca tcgaccagta cctgtattac   4560
ttgagcagaa caaacactcc aagtggaacc accacgcagt caaggcttca gttttctcag   4620
gccgagcga gtgacattcg ggaccagtct aggaactggc ttcctggacc ctgttaccgc    4680
cagcagcgag tatcaaagac atctgcggat aacaacaaca gtgaatactc gtggactgga   4740
gctaccaagt accacctcaa tggcagagac tctctggtga atccggccat ggcaagccac   4800
aaggacgatg aagaaaagtt ttttcctcag agcggggttc tcatctttgg gaagcaaggc   4860
tcagagaaaa caaatgtgaa cattgaaaag gtcatgatta cagacgaaga ggaaatcgga   4920
acaaccaatc ccgtggctac ggagcagtat ggttctgtat ctaccaacct ccagagaggc   4980
aacagacaag cagctaccgc agatgtcaac acacaaggcg ttcttccagg catggtctgg   5040
caggacagag atgtgtacct tcaggggccc atctgggcaa agattccaca cacggacgga   5100
catttcacc cctctcccct catgggtgga ttcggactta acaccctcc tccacagatt    5160
ctcatcaaga acacccggt acctgcgaat ccttcgacca ccttcagtgc ggcaaagttt   5220
gcttccttca tcacacagta ctccacggga acggtcagc gtggagatcg agtgggagct   5280
gcagaaggaa aacagcaaac gctggaatcc cgaaattcag tacacttcca actacaacaa   5340
gtctgttaat cgtggactta ccgtggatac taatggcgtg tattcagagc ctcgccccat   5400
tggcaccaga tacctgactc gtaatctgta attgcttgtt aatcaataaa ccgtttaatt   5460
cgtttcagtt gaactttggt ctctgcgtat ttctttctta tctagtttcc atggctacat   5520
cagcttatcg atatcagcgc tttaaatttg cgcatgctag ctatagttct agagtcgacc   5580
ggtcatggct gcgccccgac acccgccaac acccgctgac gcgccctgac gggcttgtct   5640
gctcccggca tccgcttaca gacaagctgt gaccgtctcc gggagctgca tgtgtcagag   5700
```

```
gttttcaccg tcatcaccga aacgcgcgag gcagccggat cataatcagc cataccacat   5760
ttgtagaggt tttacttgct ttaaaaaacc tccccacctc cccctgaacc tgaaacataa   5820
aatgaatgca attgttgttg ttaacttgtt tattgcagct tataatggtt acaaataaag   5880
caatagcatc acaaatttca caaataaagc attttttttca ctgcattcta gttgtggttt   5940
gtccaaactc atcaatgtat cttatcatgt ctggatccgg ccttgccggc ctcgagcggc   6000
cgctacagga acaggtggtg gcggccctcg gtgcgctcgt actgctccac gatggtgtag   6060
tcctcgttgt gggaggtgat gtccagcttg gagtccacgt agtagtagcc gggcagctgc   6120
acgggcttct tggccatgta gatggacttg aactccacca ggtagtggcc gccgtccttc   6180
agcttcaggg ccttgtggat ctcgcccttc agcacgccgt cgcggggggta caggcgctcg   6240 gtggaggcct cccagcccat ggtcttcttc tgcattacgg ggccgtcgga ggggaagttc   6300
acgccgatga acttcacctt gtagatgaag cagccgtcct gcaggagga gtcctgggtc   6360 acggtcacca cgccgccgtc ctcgaagttc atcacgcgct cccacttgaa gccctcgggg   6420
aaggacagct tcttgtagtc ggggatgtcg gcggggtgct tcacgtacac cttggagccg   6480
tactggaact gggggggacag gatgtcccag gcgaagggca gggggccgcc cttggtcacc   6540
ttcagcttca cggtgttgtg gccctcgtag gggcggccct cgccctcgcc ctcgatctcg   6600
aactcgtggc cgttcacggt gccctccatg cgcaccttga agcgcatgaa ctccttgatg   6660
acgttcttgg aggagcgcac catggtggcg accggtggat cccgggcccg cggtacccag   6720
cttggaggtg cacaccaatg tggtgaatgg tcaaatggcg tttattgtat cgagctaggc   6780
acttaaatac aatatctctg caatgcggaa ttcagtggtt cgtccaatcc atgtcagacc   6840
cgtctgttgc cttcctaata aggcacgatc gtaccacctt acttccacca atcggcatgc   6900
acggtgcttt ttctctcctt gtaaggcatg ttgctaactc atcgttacca tgttgcaaga   6960
ctacaagagt attgcataag actacatttc cccctcccta tgcaaaagcg aaactactat   7020
atcctgaggg gactcctaac cgcgtacaac cgaagccccg cttttcgcct aaacacaccc   7080
tagtcccctc agatacgcgt atatctggcc cgtacatcgc gaagcagcgc aaaacgccta   7140
accctaagca gattcttcat gcaattgtcg gtcaagcctt gccttgttgt agcttaaatt   7200
ttgctcgcgc actactcagc gacctccaac acacaagcag ggagcagata ctggcttaac   7260
tatgcggcat cagagcagat tgtactgaga gtgcaccata cggatctgcg atgataagct   7320
gtcaaacatg agaattggtc gacctgcagc tggcgccatc gatgcatgtc cttgggtccg   7380
gcctgctgaa tgcgcaggcg gtcggccatg ccccaggctt cgttttgaca tcggcgcagg   7440
tctttgtagt agtcttgcat gagccttcct accggcactt cttcttctcc ttcctcttgt   7500
cctgcatctc ttgcatctat cgctgcgcg gcggcggagt ttggccgtag gtggcgccct   7560
cttcctccca tgcgtgtgac cccgaagccc ctcatcggct gaagcagggc taggtcggcg   7620
acaacgcgct cggctaatat ggcctgctgc acctgcgtga gggtagactg gaagtcatcc   7680
atgtccacaa agcggtggta tgcgcccgtg ttgatggtgt aagtgcagtt ggccataacg   7740
gaccagttaa cggtctggtg acccggctgc gagagctcgg tgtacctgag acgcgagtaa   7800
gccctcgagt caaatacgta gtcgttgcaa gtccgcacca ggtactggta tcccaccaaa   7860
aagtgcggcg gcggctggcg gtagaggggc cagcgtaggg tggccggggc tccggggggcg   7920 agatcttcca acataaggcg atgatatccg tagatgtacc tggacatcca ggtgatgccg   7980
gcggcggtgg tggaggcgcg cggaaagtcg cggacgcggt tccagatgtt gcgcagcggc   8040
```

```
aaaaagtgct ccatggtcgg gacgctctgg ccggtcaggc gcgcgcaatc gttgacgctc    8100
tagaccgtgc aaaaggagag cctgtaagcg ggcactcttc cgtggtctgg tggataaatt    8160
cgcaagggta tcatggcgga cgaccggggt tcgagcccg tatccggccg tccgccgtga     8220
tccatgcggt taccgcccgc gtgtcgaacc caggtgtgcg acgtcagaca acggggagt     8280 gctccttttg gcttccttcc aggcgcggcg gctgctgcgc tagcttttt ggccactggc     8340 cgcgcgcagc gtaagcggtt aggctggaaa gcgaaagcat taagtggctc gctccctgta    8400
gccggagggt tattttccaa gggttgagtc gcgggacccc cggttcgagt ctcggaccgg    8460
ccggactgcg gcgaacgggg gtttgcctcc ccgtcatgca agaccccgct tgcaaattcc    8520
tccggaaaca gggacgagcc ccttttttgc ttttcccaga tgcatccggt gctgcggcag    8580
atgcgccccc ctcctcagca gcggcaagag caagagcagc ggcagacatg cagggcaccc    8640
tcccctcctc ctaccgcgtc aggaggggcg acatccgcgg ttgacgcggc agcagatggt    8700
gattacgaac ccccgcggcg ccgggcccgg cactacctgg acttggagga gggcgagggc    8760
ctggcgcggc taggagcgcc ctctcctgag cggtacccaa gggtgcagct gaagcgtgat    8820
acgcgtgagg cgtacgtgcc gcggcagaac ctgtttcgcg accgcgaggg agaggagccc    8880
gaggagatgc gggatcgaaa gttccacgca gggcgcgagc tgcggcatgg cctgaatcgc    8940
gagcggttgc tgcgcgagga ggactttgag cccgacgcgc gaaccgggat tagtcccgcg    9000
cgcgcacacg tggcggccgc cgacctggta accgcatacg agcagacggt gaaccagggc    9060
gatcgcaccc tttggcgcat cccattctcc agtaacttta tgtccatggg cgcactcaca    9120
gacctgggcc aaaaccttct ctacgccaac tccgcccacg cgctagacat gacttttgag    9180
gtggatccca tggacgagcc caccttctt tatgttttgt ttgaagtctt tgacgtggtc      9240
cgtgtgcacc ggccgcaccg cggcgtcatc gaaaccgtgt acctgcgcac gcccttctcg    9300
gccggcaacg ccacaacata aagaagcaag caacatcaac aacagctgcc gccatgggct    9360
ccagtgagca ggaactgaaa gccattgtca aagatcttgg ttgtgggcca tattttttgg    9420
gcacctatga caagcgcttt ccaggctttg tttctccaca caagctcgcc tgcgccatag    9480
tcaatacggc cggtcgcgag actgggggcg tacactggat ggcctttgcc tggaacccgc    9540
actcaaaaac atgctacctc tttgagccct ttggcttttc tgaccagcga ctcaagcagg    9600
tttaccagtt tgagtacgag tcactcctgc gccgtagcgc cattgcttct tcccccgacc    9660
gctgtataac gctggaaaag tccacccaaa gcgtacaggg gcccaactcg gccgcctgtg    9720
gactattctg ctgcatgttt ctccacgcct ttgccaactg gccccaaact cccatggatc    9780
acaaccccac catgaacctt attaccgggg tacccaactc catgctcaac agtccccagg    9840
tacagcccac cctgcgtcgc aaccaggaac agctctacag cttcctggag cgccactcgc    9900
cctacttccg cagccacagt gcgcagatta ggagcgccac ttcttttgt cacttgaaaa     9960 acatgtaaaa ataatgtact agagacactt tcaataaagg caaatgcttt tatttgtaca   10020
ctctcgggtg attatttacc cccacccttg ccgtctgcgc cgtttaaaaa tcaaggggt    10080 tctgccgcgc atcgctatgc gccactggca gggacacgtt gcgatactgg tgtttagtgc   10140
tccacttaaa ctcaggcaca accatccgcg gcagctcggt gaagttttca ctccacaggc   10200
tgcgcaccat caccaacgcg tttagcaggt cgggcgccga tatcttgaag tcgcagttgg   10260
ggcctccgcc ctgcgcgcgc gagttgcgat acacagggtt gcagcactgg aacactatca   10320
gcgccggtgt gtgcacgctg gccagcacgc tcttgtcgga gatcagatcc gcgtccaggt   10380
cctccgcgtt gctcagggcg aacggagtca actttggtag ctgccttccc aaaaagggcg   10440
```

```
cgtgcccagg ctttgagttg cactcgcacc gtagtggcat caaaaggtga ccgtgcccgg   10500
tctgggcgtt aggatacagc gcctgcataa aagccttgat ctgcttaaaa gccacctgag   10560
cctttgcgcc ttcagagaag aacatgccgc aagacttgcc ggaaaactga ttggccggac   10620
aggccgcgtc gtgcacgcag caccttgcgt cggtgttgga gatctgcacc acatttcggc   10680
cccaccggtt cttcacgatc ttggccttgc tagactgctc cttcagcgcg cgctgcccgt   10740
tttcgctcgt cacatccatt tcaatcacgt gctccttatt tatcataatg cttccgtgta   10800
gacacttaag ctcgccttcg atctcagcgc agcggtgcag ccacaacgcg cagcccgtgg   10860
gctcgtgatg cttgtaggtc acctctgcaa acgactgcag gtacgcctgc aggaatcgcc   10920
ccatcatcgt cacaaaggtc ttgttgctgg tgaaggtcag ctgcaacccg cggtgctcct   10980
cgttcagcca ggtcttgcat acggccgcca gagcttccac ttggtcaggc agtagtttga   11040
agttcgcctt tagatcgtta ccacgtggt acttgtccat cagcgcgcgc gcagcctcca   11100
tgcccttctc ccacgcagac acgatcggca cactcagcgg gttcatcacc gtaatttcac   11160
tttccgcttc gctgggctct tcctcttcct cttgcgtccg cataccacgc gccactgggt   11220
cgtcttcatt cagccgccgc actgtgcgct tacctccttt gccatgcttg attagcaccg   11280
gtgggttgct gaaacccacc atttgtagcg ccacatcttc tctttcttcc tcgctgtcca   11340
cgattacctc tggtgatggc gggcgctcgg gcttgggaga agggcgcttc ttttcttct   11400 tgggcgcaat ggccaaatcc gccgccgagg tcgatggccg cgggctgggt gtgcgcggca   11460
ccagcgcgtc ttgtgatgag tcttcctcgt cctcggactc gatacgccgc ctcatccgct   11520
tttttggggg cgcccgggga ggcggcggcg acggggacgg ggacgacacg tcctccatgg   11580 ttggggacg tcgcgccgca ccgcgtccgc gctcgggggt ggtttcgcgc tgctcctctt   11640
cccgactggc catttccttc tcctataggc agaaaaagat catggagtca gtcgagaaga   11700
aggacagcct aaccgccccc tctgagttcg ccaccaccgc ctccaccgat gccgccaacg   11760
cgcctaccac cttccccgtc gaggcacccc cgcttgagga ggaggaagtg attatcgagc   11820
aggacccagg ttttgtaagc gaagacgacg aggaccgctc agtaccaaca gaggataaaa   11880
agcaagacca ggacaacgca gaggcaaacg aggaacaagt cgggcggggg gacgaaaggc   11940
atggcgacta cctagatgtg ggagacgacg tgctgttgaa gcatctgcag cgccagtgcg   12000
ccattatctg cgacgcgttg caagagcgca gcgatgtgcc cctcgccata gcggatgtca   12060
gccttgccta cgaacgccac ctattctcac cgcgcgtacc ccccaaacgc aagaaaacg   12120 gcacatgcga gcccaacccg cgcctcaact tctaccccgt atttgccgtg ccagaggtgc   12180
ttgccaccta tcacatcttt ttccaaaact gcaagatacc cctatcctgc cgtgccaacc   12240
gcagccgagc ggacaagcag ctggccttgc ggcagggcg tgtcatacct gatatcgcct   12300
cgctcaacga agtgccaaaa atctttgagg gtcttggacg cgacgagaag cgcgcggcaa   12360 acgtctctgca acaggaaaac agcgaaaatg aaagtcactc tggagtgttg gtggaactcg   12420
agggtgacaa cgcgcgccta gccgtactaa aacgcagcat cgaggtcacc cactttgcct   12480
acccggcact taacctaccc cccaaggtca tgagcacagt catgagtgag ctgatcgtgc   12540
gccgtgcgca gcccctggag agggatgcaa atttgcaaga acaaacagag gagggcctac   12600
ccgcagttgg cgacgagcag ctagcgcgct ggcttcaaac gcgcgagcct gccgacttgg   12660
aggagcgacg caaactaatg atggccgcag tgctcgttac cgtggagctt gagtgcatgc   12720
agcggttctt tgctgacccg gagatgcagc gcaagctaga ggaaacattg cactacacct   12780
```

```
ttcgacaggg ctacgtacgc caggcctgca agatctccaa cgtggagctc tgcaacctgg   12840
tctcctacct tggaattttg cacgaaaacc gccttgggca aaacgtgctt cattccacgc   12900
tcaagggcga ggcgcgccgc gactacgtcc gcgactgcgt ttacttattt ctatgctaca   12960
cctggcagac ggccatgggc gtttggcagc agtgcttgga ggagtgcaac ctcaaggagc   13020
tgcagaaact gctaaagcaa aacttgaagg acctatggac ggccttcaac gagcgctccg   13080
tggccgcgca cctggcggac atcattttcc ccgaacgcct gcttaaaacc ctgcaacagg   13140
gtctgccaga cttcaccagt caaagcatgt tgcagaactt taggaacttt atcctagagc   13200
gctcaggaat cttgcccgcc acctgctgtg cacttcctag cgactttgtg cccattaagt   13260
accgcgaatg ccctccgccg ctttggggcc actgctacct tctgcagcta gccaactacc   13320
ttgcctacca ctctgacata atggaagacg tgagcggtga cggtctactg gagtgtcact   13380
gtcgctgcaa cctatgcacc ccgcaccgct ccctggtttg caattcgcag ctgcttaacg   13440
aaagtcaaat tatcggtacc tttgagctgc agggtccctc gcctgacgaa aagtccgcgg   13500
ctccggggtt gaaactcact ccggggctgt ggacgtcggc ttaccttcgc aaatttgtac   13560
ctgaggacta ccacgcccac gagattaggt tctacgaaga ccaatcccgc ccgccaaatg   13620
cggagcttac cgcctgcgtc attacccagg gccacattct tggccaattg caagccatca   13680
acaaagcccg ccaagagttt ctgctacgaa agggacgggg ggtttacttg gacccccagt   13740
ccggcgagga gctcaaccca atcccccgc cgccgcagcc ctatcagcag cagccgcggg   13800
cccttgcttc ccaggatggc acccaaaaag aagctgcagc tgccgccgcc acccacggac   13860
gaggaggaat actgggacag tcaggcagag gaggttttgg acgaggagga ggaggacatg   13920
atggaagact gggagagcct agacgaggaa gcttccgagg tcgaagaggt gtcagacgaa   13980
acaccgtcac cctcggtcgc attccctcg ccggcgcccc agaaatcggc aaccggttcc   14040
agcatggcta caacctccgc tcctcaggcg ccgccggcac tgcccgttcg ccgacccaac   14100
cgtagatggg acaccactgg aaccagggcc ggtaagtcca agcagccgcc gccgttagcc   14160
caagagcaac aacagcgcca aggctaccgc tcatggcgcg ggcacaagaa cgccatagtt   14220
gcttgcttgc aagactgtgg gggcaacatc tccttcgccc gccgctttct tctctaccat   14280
cacggcgtgg ccttcccccg taacatcctg cattactacc gtcatctcta cagcccatac   14340
tgcaccggcg gcagcggcag cggcagcaac agcagcggcc acacagaagc aaaggcgacc   14400
ggatagcaag actctgacaa agcccaagaa atccacagcg gcggcagcag caggaggagg   14460
agcgctgcgt ctggcgccca acgaacccgt atcgacccgc gagcttagaa acaggatttt   14520
tcccactctg tatgctatat ttcaacagag caggggccaa gaacaagagc tgaaaataaa   14580
aaacaggtct ctgcgatccc tcacccgcag ctgcctgtat cacaaaagcg aagatcagct   14640
tcggcgcacg ctggaagacg cggaggctct cttcagtaaa tactgcgcgc tgactcttaa   14700
ggactagttt cgcgccctt ctcaaattta agcgcgaaaa ctacgtcatc tccagcggcc   14760
acacccggcg ccagcacctg tcgtcagcgc cattatgagc aaggaaattc ccacgcccta   14820
catgtggagt taccagccac aaatgggact tgcggctgga gctgcccaag actactcaac   14880
ccgaataaac tacatgagcg cgggacccca catgatatcc cgggtcaacg gaatccgcgc   14940
ccaccgaaac cgaattctct tggaacaggc ggctattacc accacacctc gtaataacct   15000
taatccccgt agttggcccg ctgccctggt gtaccaggaa agtcccgctc ccaccactgt   15060
ggtacttccc agagacgccc aggccgaagt tcagatgact aactcagggg cgcagcttgc   15120
gggcggcttt cgtcacaggg tgcggtcgcc cgggcagggt ataactcacc tgacaatcag   15180
```

```
agggcgaggt attcagctca acgacgagtc ggtgagctcc tcgcttggtc tccgtccgga   15240
cgggacattt cagatcggcg gcgccggccg ctcttcattc acgcctcgtc aggcaatcct   15300
aactctgcag acctcgtcct ctgagccgcg ctctggaggc attggaactc tgcaatttat   15360
tgaggagttt gtgccatcgg tctactttaa ccccttctcg ggacctcccg gccactatcc   15420
ggatcaattt attcctaact ttgacgcggt aaaggactcg gcggatggct acgactgaat   15480
gttaagtgga gaggcagagc aactgcgcct gaaacacctg gtccactgtc gccgccacaa   15540
gtgctttgcc cgcgactccg gtgagttttg ctactttgaa ttgcccgagg atcatatcga   15600
gggcccggcg cacggcgtcc ggcttaccgc ccagggagag cttgcccgta gcctgattcg   15660
ggagtttacc cagcgccccc tgctagttga gcgggacagg ggaccctgtg ttctcactgt   15720
gatttgcaac tgtcctaacc ctggattaca tcaagatctt tgttgccatc tctgtgctga   15780
gtataataaa tacagaaatt aaaatatact ggggctccta tcgccatcct gtaaacgcca   15840
ccgtcttcac ccgcccaagc aaaccaaggc gaaccttacc tggtactttt aacatctctc   15900
cctctgtgat ttacaacagt ttcaacccag acggagtgag tctacgagag aacctctccg   15960
agctcagcta ctccatcaga aaaaacacca ccctccttac ctgccgggaa cgtacgagtg   16020
cgtcaccggc cgctgcacca cacctaccgc ctgaccgtaa accagacttt tccggacag   16080 acctcaataa ctctgtttac cagaacagga ggtgagctta gaaaacccctt agggtattag   16140 gccaaaggcg cagctactgt ggggtttatg aacaattcaa gcaactctac gggctattct   16200
aattcaggtt tctctagaaa tggacggaat tattacagag cagcgcctgc tagaaagacg   16260
cagggcagcg gccgagcaac agcgcatgaa tcaagagctc caagacatgg ttaacttgca   16320
ccagtgcaaa aggggtatct tttgtctggt aaagcaggcc aaagtcacct acgacagtaa   16380
taccaccgga caccgcctta gctacaagtt gccaaccaag cgtcagaaat tggtggtcat   16440
ggtgggagaa aagcccatta ccataactca gcactcggta gaaaccgaag gctgcattca   16500
ctcaccttgt caaggacctg aggatctctg cacccttatt aagaccctgt gcggtctcaa   16560
agatcttatt ccctttaact aataaaaaaa aataataaag catcacttac ttaaaatcag   16620
ttagcaaatt tctgtccagt ttattcagca gcacctcctt gccctcctcc cagctctggt   16680
attgcagctt cctcctggct gcaaactttc tccacaatct aaatggaatg tcagtttcct   16740
cctgttcctg tccatccgca cccactatct tcatgttgtt gcagatgaag cgcgcaagac   16800
cgtctgaaga taccttcaac cccgtgtatc catatgacac ggaaaccggt cctccaactg   16860 tgcctttttct tactcctccc tttgtatccc ccaatgggtt tcaagagagt cccctgggg   16920 tactctcttt gcgcctatcc gaacctctag ttacctccaa tggcatgctt gcgctcaaaa   16980
tgggcaacgg cctctctctg gacgaggcg gcaaccttac ctcccaaaat gtaaccactg   17040
tgagcccacc tctcaaaaaa accaagtcaa acataaacct ggaaatatct gcaccactca   17100
cagttacctc agaagcccta actgtggctg ccgccgcacc tctaatggtc gcgggcaaca   17160
cactcaccat gcaatcacag gccccgctaa ccgtgcacga ctccaaactt agcattgcca   17220
cccaaggacc cctcacagtg tcagaaggaa agctagccct gcaaacatca ggccccctca   17280
ccaccaccga tagcagtacc cttactatca ctgcctcacc cctctaact actgccactg   17340 gtagcttggg cattgacttg aaagagccca tttatacaca aaatggaaaa ctaggactaa   17400 agtacgggc tccttttgcat gtaacagacg acctaaacac tttgaccgta gcaactggtc   17460
caggtgtgac tattaataat acttccttgc aaactaaagt tactggagcc ttgggttttg   17520
```

```
attcacaagg caatatgcaa cttaatgtag caggaggact aaggattgat tctcaaaaca    17580
gacgccttat acttgatgtt agttatccgt ttgatgctca aaaccaacta aatctaagac    17640
taggacaggg ccctcttttt ataaactcag cccacaactt ggatattaac tacaacaaag    17700
gcctttactt gtttacagct tcaaacaatt ccaaaaagct tgaggttaac ctaagcactg    17760
ccaaggggtt gatgtttgac gctacagcca tagccattaa tgcaggagat gggcttgaat    17820
ttggttcacc taatgcacca aacacaaatc ccctcaaaac aaaaattggc catggcctag    17880
aatttgattc aaacaaggct atggttccta aactaggaac tggccttagt tttgacagca    17940
caggtgccat tacagtagga aacaaaaata atgataagct aactttgtgg accacaccag    18000
ctccatctcc taactgtaga ctaaatgcag agaaagatgc taaactcact ttggtcttaa    18060
caaaatgtgg cagtcaaata cttgctacag tttcagtttt ggctgttaaa ggcagtttgg    18120
ctccaatatc tggaacagtt caaagtgctc atcttattat aagatttgac gaaaatggag    18180
tgctactaaa caattccttc ctggacccag aatattggaa ctttagaaat ggagatctta    18240
ctgaaggcac agcctataca aacgctgttg gatttatgcc taacctatca gcttatccaa    18300
aatctcacgg taaaactgcc aaaagtaaca ttgtcagtca agtttactta aacggagaca    18360
aaactaaacc tgtaacacta accattcac taaacggtac acaggaaaca ggagacacaa    18420
ctccaagtgc atactctatg tcattttcat gggactggtc tggccacaac tacattaatg    18480
aaatatttgc cacatcctct tacactttt catacattgc ccaagaataa agaatcgttt    18540
gtgttatgtt tcaacgtgtt tatttttcaa ttgcagaaaa tttcaagtca ttttcattc    18600 agtagtatag ccccaccacc acatagctta tacagatcac cgtaccttaa tcaaactcac    18660
agaaccctag tattcaacct gccacctccc tcccaacaca cagagtacac agtcctttct    18720
ccccggctgg ccttaaaaag catcatatca tgggtaacag acatattctt aggtgttata    18780
ttccacacgg tttcctgtcg agccaaacgc tcatcagtga tattaataaa ctccccgggc    18840
agctcactta agttcatgtc gctgtccagc tgctgagcca caggctgctg tccaacttgc    18900
ggttgcttaa cgggcggcga aggagaagtc cacgcctaca tgggggtaga gtcataatcg    18960
tgcatcagga tagggcggtg gtgctgcagc agcgcgcgaa taaactgctg ccgccgccgc    19020
tccgtcctgc aggaatacaa catggcagtg gtctcctcag cgatgattcg caccgcccgc    19080
agcataaggc gccttgtcct ccgggcacag cagcgcaccc tgatctcact taaatcagca    19140
cagtaactgc agcacagcac cacaatattg ttcaaaatcc cacagtgcaa ggcgctgtat    19200
ccaaagctca tggcggggac cacagaaccc acgtggccat cataccacaa gcgcaggtag    19260
attaagtggc gacccctcat aaacacgctg gacataaaca ttacctcttt tggcatgttg    19320
taattcacca cctcccggta ccatataaac ctctgattaa acatggcgcc atccaccacc    19380
atcctaaacc agctggccaa aacctgcccg ccggctatac actgcaggga accgggactg    19440
gaacaatgac agtggagagc ccaggactcg taaccatgga tcatcatgct cgtcatgata    19500
tcaatgttgg cacaacacag gcacacgtgc atacacttcc tcaggattac aagctcctcc    19560
cgcgttagaa ccatatccca gggaacaacc cattcctgaa tcagcgtaaa tcccacactg    19620
cagggaagac ctcgcacgta actcacgttg tgcattgtca aagtgttaca ttcgggcagc    19680
agcggatgat cctccagtat ggtagcgcgg gtttctgtct caaaaggagg tagacgatcc    19740
ctactgtacg gagtgcgccg agacaaccga gatcgtgttg gtcgtagtgt catgccaaat    19800
ggaacgccag acgtagtcat atttcctgaa gcaaaaccag gtgcgggcgt gacaaacaga    19860
tctgcgtctc cggtctcgcc gcttagatcg ctctgtgtag tagttgtagt atatccactc    19920
```

```
tctcaaagca tccaggcgcc ccctggcttc gggttctatg taaactcctt catgcgccgc   19980
tgccctgata acatccacca ccgcagaata agccacaccc agccaaccta cacattcgtt   20040
ctgcgagtca cacacgggag gagcgggaag agctggaaga accatgtttt ttttttttatt  20100 ccaaaagatt atccaaaacc tcaaaatgaa gatctattaa gtgaacgcgc tccctccgg   20160 tggcgtggtc aaactctaca gccaaagaac agataatggc atttgtaaga tgttgcacaa   20220
tggcttccaa aaggcaaacg gccctcacgt ccaagtggac gtaaaggcta aacccttcag   20280
ggtgaatctc ctctataaac attccagcac cttcaaccat gcccaaataa ttctcatctc   20340
gccaccttct caatatatct ctaagcaaat cccgaatatt aagtccggcc attgtaaaaa   20400
tctgctccag agcgccctcc accttcagcc tcaagcagcg aatcatgatt gcaaaaattc   20460
aggttcctca cagacctgta taagattcaa aagcggaaca ttaacaaaaa taccgcgatc   20520
ccgtaggtcc cttcgcaggg ccagctgaac ataatcgtgc aggtctgcac ggaccagcgc   20580
ggccacttcc ccgccaggaa ccatgacaaa agaacccaca ctgattatga cacgcatact   20640
cggagctatg ctaaccagcg tagccccgat gtaagcttgt tgcatgggcg gcgatataaa   20700
atgcaaggtg ctgctcaaaa aatcaggcaa agcctcgcgc aaaaaagaaa gcacatcgta   20760
gtcatgctca tgcagataaa ggcaggtaag ctccggaacc accacagaaa aagacaccat   20820
ttttctctca aacatgtctg cgggtttctg cataaacaca aaataaaata acaaaaaaac   20880
atttaaacat tagaagcctg tcttacaaca ggaaaaacaa cccttataag cataagacgg   20940
actacggcca tgccggcgtg accgtaaaaa aactggtcac cgtgattaaa aagcaccacc   21000
gacagctcct cggtcatgtc cggagtcata atgtaagact cggtaaacac atcaggttga   21060
ttcacatcgg tcagtgctaa aaagcgaccg aaatagcccg ggggaataca tacccgcagg   21120
cgtagagaca acattacagc ccccatagga ggtataacaa aattaatagg agagaaaaac   21180
acataaacac ctgaaaaacc ctcctgccta ggcaaaatag caccctcccg ctccagaaca   21240
acatacagcg cttccacagc ggcagccata acagtcagcc ttaccagtaa aaaagaaaac   21300
ctattaaaaa aacaccactc gacacggcac cagctcaatc agtcacagtg taaaaaaggg   21360
ccaagtgcag agcgagtata tataggacta aaaaatgacg taacggttaa agtccacaaa   21420
aaacacccag aaaaccgcac gcgaacctac gcccagaaac gaaagccaaa aaacccacaa   21480
cttcctcaaa tcgtcacttc cgttttccca cgttacgtca cttcccattt taagaaaact   21540
acaattccca acacatacaa gttactccgc cctaaaacct acgtcacccg ccccgttccc   21600
acgccccgcg ccacgtcaca aactccaccc cctcattatc atattggctt caatccaaaa   21660
taaggtatat tattgatgat gttaattaag aattcggatc tgcgacgcga ggctggatgg   21720
ccttccccat tatgattctt ctcgcttccg gcggcatcgg gatgcccgcg ttgcaggcca   21780
tgctgtccag gcaggtagat gacgaccatc agggacagct tcacggccag caaaaggcca   21840
ggaaccgtaa aaaggccgcg ttgctggcgt ttttccatag gctccgcccc cctgacgagc   21900
atcacaaaaa tcgacgctca gtcagaggt ggcgaaaccc gacaggacta taaagatacc   21960
aggcgtttcc ccctggaagc tccctcgtgc gctctcctgt tccgaccctg ccgcttaccg   22020
gatacctgtc cgcctttctc ccttcgggaa gcgtggcgct ttctcatagc tcacgctgta   22080
ggtatctcag ttcggtgtag gtcgttcgct ccaagctggg ctgtgtgcac gaaccccccg   22140
ttcagcccga ccgctgcgcc ttatccggta actatcgtct tgagtccaac ccggtaagac   22200
acgacttatc gccactggca gcagccactg gtaacaggat tagcagagcg aggtatgtag   22260
```

```
gcggtgctac agagttcttg aagtggtggc ctaactacgg ctacactaga agaacagtat    22320
ttggtatctg cgctctgctg aagccagtta ccttcggaaa aagagttggt agctcttgat    22380
ccggcaaaca aaccaccgct ggtagcggtg gttttttttgt ttgcaagcag cagattacgc    22440
gcagaaaaaa aggatctcaa gaagatcctt tgatcttttc tacggggtct gacgctcagt    22500
ggaacgaaaa ctcacgttaa gggattttgg tcatgagatt atcaaaaagg atcttcacct    22560 agatccttt aaatcaatct aaagtatata tgagtaaact tggtctgaca gttaccaatg    22620
cttaatcagt gaggcaccta tctcagcgat ctgtctattt cgttcatcca tagttgcctg    22680
actccccgtc gtgtagataa ctacgatacg ggagggctta ccatctggcc ccagtgctgc    22740
aatgataccg cgagacccac gctcaccggc tccagattta tcagcaataa accagccagc    22800
cggaagggcc gagcgcagaa gtggtcctgc aactttatcc gcctccatcc agtctattaa    22860
ttgttgccgg gaagctagag taagtagttc gccagttaat agtttgcgca acgttgttgc    22920
cattgctgca ggcatcgtgg tgtcacgctc gtcgtttggt atggcttcat tcagctccgg    22980
ttcccaacga tcaaggcgag ttacatgatc ccccatgttg tgcaaaaaag cggttagctc    23040
cttcggtcct ccgatcgttg tcagaagtaa gttggcagca gtgttatcac tcatggttat    23100
ggcagcactg cataattctc ttactgtcat gccatccgta agatgctttt ctgtgactgg    23160
tgagtactca accaagtcat tctgagaata gtgtatgcgg cgaccgagtt gctcttgccc    23220
ggcgtcaaca cgggataata ccgcaccaca tagcagaact ttaaaagtgc tcatcattgg    23280
aaaacgttct cggggcgaa aactctcaag gatcttaccg ctgttgagat ccagttcgat    23340
gtaacccact cgtgcaccca actgatcttc agcatctttt actttcacca gcgtttctgg    23400
gtgagcaaaa acaggaaggc aaaatgccgc aaaaaaggga ataagggcga cacgaaaatg    23460
ttgaatactc atactcttcc tttttcaata ttattgaagc atttatcagg gttattgtct    23520
catgagcgga tacatatttg aatgtattta gaaaaataaa caaatagggg ttccgcgcac    23580
atttccccga aaagtgccac ctgacgtcta agaaaccatt attatcatga cattaaccta    23640
taaaaatagg cgtatcacga ggccctttcg tcttcaa                             23677
```

<210> SEQ ID NO 2
<211> LENGTH: 21846
<212> TYPE: DNA
<213> ORGANISM: Artificial Sequence
<220> FEATURE:
<223> OTHER INFORMATION: Synthesized in laboratory

<400> SEQUENCE: 2

```
ggatccgaat tcttaattaa catcatcaat aatataccttatttttggatt gaagccaata     60 tgataatgag ggggtggagt ttgtgacgtg cgcggggcg tgggaacggg gcgggtgacg    120
tagtagtgtg gcggaagtgt gatgttgcaa gtgtggcgga acacatgtaa gcgacggatg    180
tggcaaaagt gacgttttg gtgtgcgccg gtgtacacag gaagtgacaa ttttcgcgcg    240
gttttaggcg gatgttgtag taaatttggg cgtaaccgag taagatttgg ccattttcgc    300
gggaaaactg aataagagga agtgaaatct gaataatttt gtgttactca tagcgcgtaa    360
tatttgtcta gggccgcggg gactttgacc gtttacgtgg agactcgccc aggtgttttt    420
ctcaggtgtt ttccgcgttc cgggtcaaag ttggcgtttt attattatag tcaggggat    480 cctctagaac tagtggatcc gtccctcagg cctagaagta aaaagggaa aaagagtgt    540 gtttgtcaaa ataggagaca ggtggtgca accaaggact tataggggac cttacatcta    600
cagaccaaca gatgccccct taccatatac aggaagatat gacttaaatt gggataggtg    660
```

```
ggtcacaatc aacggctata aagtgttata cagatccctc ccctcccctt tcgtgaaaga    720
ctcgccagag ctagacctcc ttggtgtatg ctaactgaga agagaaagac gacatgaaac    780
aacaggtaca tgattatatt tatctaggaa caggaatgca cttttgggga aaggttttcc    840
ataccaagga aggggcagtg gctggactga tagaacatta ttctgcaaaa acttatggta    900
tgagttatta tgattagcct ttatttgccc aaccttgcgg ttcccagggt ttaaataagt    960
ttatggttac aaactgttct taaaacgagg atgtgagaca agtggtttcc tgacttggtt   1020
tggtaatcaa atgttctgat ctgagctctt agtgttctat tttcctatgt tcttttggaa   1080
tctatccaag tcttatgtaa atgcttatgt aaaccataat ataaaagagt gctgattttt   1140
tgagtaaact tgcaacagtc ctaacattct tctctcgtgt gtttgtgtct gttcgccatc   1200
ccgtctccgc tcgtcactta tccttcactt ttcagagggt cccccgcag atccggtca     1260
ccctcaggtc gggacctgca gaagacgccc gagtgagcac gcagggtctc cattttgaag   1320
cgggaggttt gaacgcgcag ccgccatgcc ggggttttac gagattgtga ttaaggtccc   1380
cagcgacctt gacgggcatc tgcccggcat ttctgacagc tttgtgaact gggtggccga   1440
gaaggaatgg gagttgccgc cagattctga catggatctg aatctgattg agcaggcacc   1500
cctgaccgtg gccgagaagc tgcagcgcga ctttctgacg aatggcgcc gtgtgagtaa    1560
ggccccggag gcccttttct ttgtgcaatt tgagaaggga gagagctact tccacatgca   1620
cgtgctcgtg gaaaccaccg gggtgaaatc catggttttg gacgttttcc tgagtcagat   1680
tcgcgaaaaa ctgattcaga gaatttaccg cgggatcgag ccgactttgc caaactggtt   1740
cgcggtcaca aagaccagaa atggcgccgg aggcgggaac aaggtggtgg atgagtgcta   1800
catccccaat tacttgctcc ccaaaaccca gcctgagctc cagtgggcgt ggactaatat   1860
ggaacagtat ttaagcgcct gtttgaatct cacggagcgt aaacggttgg tggcgcagca   1920
tctgacgcac gtgtcgcaga cgcaggagca gaacaaagag aatcagaatc ccaattctga   1980
tgcgccggtg atcagatcaa aaacttcagc caggtacatg gagctggtcg ggtggctcgt   2040
ggacaagggg attaccctcg gagaagcagtg gatccaggag gaccaggcct catacatctc   2100
cttcaatgcg gcctccaact cgcggtccca aatcaaggct gccttggaca atgcgggaaa   2160
gattatgagc ctgactaaaa ccgcccccga ctacctggtg ggccagcagc ccgtggagga   2220
catttccagc aatcggattt ataaaatttt ggaactaaac gggtacgatc cccaatatgc   2280
ggcttccgtc tttctgggat gggccacgaa aaagttcggc aagaggaaca ccatctggct   2340
gtttgggcct gcaactaccg ggaagaccaa catcgcggag gccatagccc acactgtgcc   2400
cttctacggg tgcgtaaact ggaccaatga gaactttccc ttcaacgact gtgtcgacaa   2460
gatggtgatc tggtgggagg aggggaagat gaccgcaag gtcgtggagt cggccaaagc    2520
cattctcgga ggaagcaagg tgcgcgtgga ccagaaatgc aagtcctcgg cccagataga   2580
cccgactccc gtgatcgtca cctccaacac caacatgtgc gccgtgattg acgggaactc   2640
aacgaccttc gaacaccagc agccgttgca agaccggatg ttcaaatttg aactcacccg   2700
ccgtctggat catgactttg gaaggtcac caagcaggaa gtcaaagact ttttccggtg    2760
ggcaaaggat cacgtggttg aggtggagca tgaattctac gtcaaaaagg gtggagccaa   2820
gaaaagaccc gccccagtg acgcagatat aagtgagccc aaacgggtgc gcgagtcagt    2880
tgcgcagcca tcgacgtcag acgcggaagc ttcgatcaac tacgcagaca ggtaccaaaa   2940
caaatgttct cgtcacgtgg gcatgaatct gatgctgttt ccctgcagac aatgcgagag   3000
```

```
aatgaatcag aattcaaata tctgcttcac tcacggacag aaagactgtt tagagtgctt    3060
tcccgtgtca gaatctcaac ccgtttctgt cgtcaaaaag gcgtatcaga aactgtgcta    3120
cattcatcat atcatgggaa aggtgccaga cgcttgcact gcctgcgatc tggtcaatgt    3180
ggatttggat gactgcatct ttgaacaata aatgatttaa atcaggtatg gctgccgatg    3240
gttatcttcc agattggctc gaggacactc tctctgaagg aataagacag tggtggaagc    3300
tcaaacctgg cccaccacca ccaaagcccg cagagcggca taaggacgac agcaggggtc    3360
ttgtgcttcc tgggtacaag tacctcggac ccttcaacgg actcgacaag ggagagccgg    3420
tcaacgaggc agacgccgcg gccctcgagc acgtacaaag cctacgaccg gcagctcgac    3480
agcggagaca acccgtacct caagtacaac cacgccgacg cggagtttca ggagcgcctt    3540
aaagaagata cgtcttttgg gggcaacctc ggacgagcag tcttccaggc gaaaaagagg    3600
gttcttgaac ctctgggcct ggttgaggaa cctgttaaga cggctccggg aaaaaagagg    3660
ccggtagagc actctcctgt ggagccagac tcctcctcgg gaaccggaaa ggcgggccag    3720
cagcctgcaa gaaaaagatt gaattttggt cagactggag acgcagactc agtacctgac    3780
ccccagcctc tcggacagcc accagcagcc ccctctggtc tgggaactaa tacgatggct    3840
acaggcagtg gcgcaccaat ggcagacaat aacgagggcg ccgacggagt gggtaattcc    3900
tccggaaatt ggcattgcga ttccacatgg atgggcgaca gagtcatcac caccagcacc    3960
cgaacctggg ccctgcccac ctacaacaac cacctctaca aacaaatttc cagccaatca    4020
ggagcctcga acgacaatca ctactttggc tacagcaccc cttgggggta ttttgacttc    4080
aacagattcc actgccactt ttcaccacgt gactggcaaa gactcatcaa caacaactgg    4140
ggattccgac ccaagagact caacttcaag ctctttaaca ttcaagtcaa agaggtcacg    4200
cagaatgacg gtacgacgac gattgccaat aaccttacca gcacggttca ggtgtttact    4260
gactcggagt accagctccc gtacgtcctc ggctcggcgc atcaaggatg cctcccgccg    4320
ttcccagcag acgtcttcat ggtgccacag tatggatacc tcaccctgaa caacgggagt    4380
caggcagtag gacgctcttc attttactgc ctggagtact ttccttctca gatgctgcgt    4440
accgaaaaca actttacctt cagctacact tttgaggacg ttccttttcca cagcagctac    4500 gctcacagcc agagtctgga ccgtctcatg aatcctctca tcgaccagta cctgtattac    4560
ttgagcagaa caaacactcc aagtggaacc accacgcagt caaggcttca gttttctcag    4620
gccggagcga gtgacattcg ggaccagtct aggaactggc ttcctggacc ctgttaccgc    4680
cagcagcgag tatcaaagac atctgcggat aacaacaaca gtgaatactc gtggactgga    4740
gctaccaagt accacctcaa tggcagagac tctctggtga atccggccat ggcaagccac    4800
aaggacgatg aagaaaagtt ttttcctcag agcggggttc tcatctttgg gaagcaaggc    4860
tcagagaaaa caaatgtgaa cattgaaaag gtcatgatta cagacgaaga ggaaatcgga    4920
acaaccaatc ccgtggctac ggagcagtat ggttctgtat ctaccaacct ccagagaggc    4980
aacagacaag cagctaccgc agatgtcaac acacaaggcg ttcttccagg catggtctgg    5040
caggacagag atgtgtacct tcaggggccc atctgggcaa agattccaca cacggacgga    5100
cattttcacc cctctcccct catggtggga ttcggactta acacctcc tccacagatt    5160 ctcatcaaga acacccggt acctgcgaat ccttcgacca ccttcagtgc ggcaaagttt    5220
gcttccttca tcacacagta ctccacggga cacggtcagc gtggagatcg agtgggagct    5280
gcagaaggaa aacagcaaac gctggaatcc cgaaattcag tacacttcca actacaacaa    5340
gtctgttaat cgtggactta ccgtggatac taatggcgtg tattcagagc ctcgccccat    5400
```

```
tggcaccaga tacctgactc gtaatctgta attgcttgtt aatcaataaa ccgtttaatt   5460
cgtttcagtt gaactttggt ctctgcgtat ttctttctta tctagtttcc atggctacat   5520
cagcttatcg atgcatgtcc ttgggtccgg cctgctgaat gcgcaggcgg tcggccatgc   5580
cccaggcttc gttttgacat cggcgcaggt cttgtagta gtcttgcatg agcctttcta   5640
ccggcacttc ttcttctcct tcctcttgtc ctgcatctct tgcatctatc gctgcggcgg   5700
cggcggagtt tggccgtagg tggcgccctc ttcctcccat gcgtgtgacc ccgaagcccc   5760
tcatcggctg aagcagggct aggtcggcga caacgcgctc ggctaatatg gcctgctgca   5820
cctgcgtgag ggtagactgg aagtcatcca tgtccacaaa gcggtggtat gcgcccgtgt   5880
tgatggtgta agtgcagttg gccataacgg accagttaac ggtctggtga cccggctgcg   5940
agagctcggt gtacctgaga cgcgagtaag ccctcgagtc aaatacgtag tcgttgcaag   6000
tccgcaccag gtactggtat cccaccaaaa agtgcggcgg cggctggcgg tagaggggcc   6060
agcgtagggt ggccggggct ccgggggcga gatcttccaa cataaggcga tgatatccgt   6120
agatgtacct ggacatccag gtgatgccgg cggcggtggt ggaggcgcgc ggaaagtcgc   6180
ggacgcggtt ccagatgttg cgcagcggca aaagtgctc catggtcggg acgctctggc   6240
cggtcaggcg cgcgcaatcg ttgacgctct agaccgtgca aaaggagagc ctgtaagcgg   6300
gcactcttcc gtggtctggt ggataaattc gcaagggtat catggcggac gaccggggtt   6360
cgagccccgt atccggccgt ccgccgtgat ccatgcggtt accgcccgcg tgtcgaaccc   6420
aggtgtgcga cgtcagacaa cgggggagtg ctccttttgg cttccttcca ggcgcggcgg   6480
ctgctgcgct agcttttttg gccactggcc gcgcgcagcg taagcggtta ggctggaaag   6540
cgaaagcatt aagtggctcg ctccctgtag ccggagggtt attttccaag ggttgagtcg   6600
cgggaccccc ggttcgagtc tcggaccggc cggactgcgg cgaacggggg tttgcctccc   6660
cgtcatgcaa gaccccgctt gcaaattcct ccggaaacag ggacgagccc cttttttgct   6720
tttcccagat gcatccggtg ctgcggcaga tgcgcccccc tcctcagcag cggcaagagc   6780
aagagcagcg gcagacatgc agggcaccct ccctcctcc taccgcgtca ggaggggcga   6840
catccgcggt tgacgcggca gcagatggtg attacgaacc cccgcggcgc cgggcccggc   6900
actacctgga cttggaggag ggcgagggcc tggcgcggct aggagcgccc tctcctgagc   6960
ggtacccaag ggtgcagctg aagcgtgata cgcgtgaggc gtacgtgccg cggcagaacc   7020
tgtttcgcga ccgcgaggga gaggagcccg aggagatgcg ggatcgaaag ttccacgcag   7080
ggcgcgagct gcggcatggc ctgaatcgcg agcggttgct gcgcgaggag gactttgagc   7140
ccgacgcgcg aaccgggatt agtcccgcgc gcgcacacgt ggcggccgcc gacctggtaa   7200
ccgcatacga gcagacggtg aaccaggcg atcgcaccct ttgcgcatc ccattctcca   7260 gtaactttat gtccatgggc gcactcacag acctgggcca aaaccttctc tacgccaact   7320
ccgcccacgc gctagacatg acttttgagg tggatcccat ggacgagccc acccttcttt   7380
atgttttgtt tgaagtcttt gacgtggtcc gtgtgcaccg gccgcaccgc ggcgtcatcg   7440
aaaccgtgta cctgcgcacg cccttctcgg ccggcaacgc cacaacataa agaagcaagc   7500
aacatcaaca acagctgccg ccatgggctc cagtgagcag gaactgaaag ccattgtcaa   7560
agatcttggt tgtgggccat attttttggg cacctatgac aagcgctttc caggctttgt   7620
ttctccacac aagctcgcct gcgccatagt caatacggcc ggtcgcgaga ctgggggcgt   7680
acactggatg gcctttgcct ggaacccgca ctcaaaaaca tgctacctct ttgagcccct   7740
```

-continued

```
tggcttttct gaccagcgac tcaagcaggt ttaccagttt gagtacgagt cactcctgcg   7800
ccgtagcgcc attgcttctt cccccgaccg ctgtataacg ctggaaaagt ccacccaaag   7860
cgtacagggg cccaactcgg ccgcctgtgg actattctgc tgcatgtttc tccacgcctt   7920
tgccaactgg ccccaaactc ccatggatca aaccccacc atgaaccta ttaccggggt    7980
acccaactcc atgctcaaca gtccccaggt acagcccacc ctgcgtcgca accaggaaca   8040
gctctacagg ttcctggagc gccactcgcc ctacttccgc agccacagtg cgcagattag   8100
gagcgccact tcttttttgtc acttgaaaaa catgtaaaaa taatgtacta gagacacttt   8160
caataaaggc aaatgctttt atttgtacac tctcgggtga ttatttaccc ccacccttgc   8220
cgtctgcgcc gtttaaaaat caaaggggtt ctgccgcgca tcgctatgcg ccactggcag   8280
ggacacgttg cgatactggt gtttagtgct ccacttaaac tcaggcacaa ccatccgcgg   8340
cagctcggtg aagttttcac tccacaggct gcgcaccatc accaacgcgt ttagcaggtc   8400
gggcgccgat atcttgaagt cgcagttggg gcctccgccc tgcgcgcgcg agttgcgata   8460
cacagggttg cagcactgga acactatcag cgccgggtgg tgcacgctgg ccagcacgct   8520
cttgtcggag atcagatccg cgtccaggtc ctccgcgttg ctcagggcga acggagtcaa   8580
ctttggtagc tgccttccca aaagggcgc gtgcccaggc tttgagttgc actcgcaccg    8640
tagtggcatc aaaaggtgac cgtgcccggt ctgggcgtta ggatacagcg cctgcataaa   8700
agccttgatc tgcttaaaag ccacctgagc cttttgcgcct tcagagaaga acatgccgca   8760
agacttgccg gaaaactgat tggccggaca ggccgcgtcg tgcacgcagc accttgcgtc   8820
ggtgttggag atctgcacca catttcggcc ccaccggttc ttcacgatct tggcccttgct  8880
agactgctcc ttcagcgcgc gctgcccgtt ttcgctcgtc acatccattt caatcacgtg   8940
ctccttattt atcataatgc ttccgtgtag acacttaagc tcgccttcga tctcagcgca   9000
gcggtgcagc cacaacgcgc agcccgtggg ctcgtgatgc ttgtaggtca cctctgcaaa   9060
cgactgcagg tacgcctgca ggaatcgccc catcatcgtc acaaaggtct tgttgctggt   9120
gaaggtcagc tgcaacccgc ggtgctcctc gttcagccag gtcttgcata cggccgccag   9180
agcttccact tggtcaggca gtagtttgaa gttcgccttt agatcgttat ccacgtggta   9240
cttgtccatc agcgcgcgcg cagcctccat gcccttctcc cacgcagaca cgatcggcac   9300
actcagcggt tcatcaccg taatttcact ttccgcttcg ctgggctctt cctcttcctc    9360
ttgcgtccgc ataccacgcg ccactgggtc gtcttcattc agccgccgca ctgtgcgctt   9420
acctcctttg ccatgcttga ttagcaccgg tgggttgctg aaacccacca tttgtagcgc   9480
cacatcttct ctttcttcct cgctgtccac gattacctct ggtgatggcg ggcgctcggg   9540
cttgggagaa gggcgcttct ttttcttctt gggcgcaatg gccaaatccg ccgccgaggt   9600
cgatggccgc gggctgggtg tgcgcggcac cagcgcgtct tgtgatgagt cttcctcgtc   9660
ctcggactcg atacgccgcc tcatccgctt ttttggggc gcccggggag gcggcggcga   9720
cggggacggg gacgacacgt cctccatggt tgggggacgt cgccgcgcac cgcgtccgcg   9780
ctcgggggtg gtttcgcgct gctcctcttc ccgactggcc atttccttct cctataggca   9840
gaaaaagatc atggagtcag tcgagaagaa ggacagccta accgccccct ctgagttcgc   9900
caccaccgcc tccaccgatg ccgccaacgc gcctaccacc ttccccgtcg aggcaccccc   9960
gcttgaggag gaggaagtga ttatcgagca ggacccaggt tttgtaagcg aagacgacga  10020
ggaccgctca gtaccaacag aggataaaaa gcaagaccag gacaacgcag aggcaaacga  10080
ggaacaagtc gggcggggg acgaaaggca tggcgactac ctagatgtgg gagacgacgt  10140
```

-continued

```
gctgttgaag catctgcagc gccagtgcgc cattatctgc gacgcgttgc aagagcgcag    10200
cgatgtgccc ctcgccatag cggatgtcag ccttgcctac gaacgccacc tattctcacc    10260
gcgcgtaccc cccaaacgcc aagaaaacgg cacatgcgag cccaacccgc gcctcaactt    10320
ctaccccgta tttgccgtgc cagaggtgct tgccacctat cacatctttt tccaaaactg    10380
caagataccc ctatcctgcc gtgccaaccg cagccgagcg gacaagcagc tggccttgcg    10440
gcagggcgct gtcatacctg atatcgcctc gctcaacgaa gtgccaaaaa tctttgaggg    10500
tcttggacgc gacgagaagc gcgcggcaaa cgctctgcaa caggaaaaca gcgaaaatga    10560
aagtcactct ggagtgttgg tggaactcga gggtgacaac gcgcgcctag ccgtactaaa    10620
acgcagcatc gaggtcaccc actttgccta cccggcactt aacctacccc ccaaggtcat    10680
gagcacagtc atgagtgagc tgatcgtgcg ccgtgcgcag cccctggaga gggatgcaaa    10740
tttgcaagaa caaacagagg agggcctacc cgcagttggc gacgagcagc tagcgcgctg    10800
gcttcaaacg cgcgagcctg ccgacttgga ggagcgacgc aaactaatga tggccgcagt    10860
gctcgttacc gtggagcttg agtgcatgca gcggttcttt gctgacccgg agatgcagcg    10920
caagctagag gaaacattgc actacacctt tcgacagggc tacgtacgcc aggcctgcaa    10980
gatctccaac gtggagctct gcaacctggt ctcctacctt ggaattttgc acgaaaaccg    11040
ccttgggcaa aacgtgcttc attccacgct caagggcgag gcgcgccgcg actacgtccg    11100
cgactgcgtt tacttatttc tatgctacac ctggcagacg gccatgggcg tttggcagca    11160
gtgcttggag gagtgcaacc tcaaggagct gcagaaactg ctaaagcaaa acttgaagga    11220
cctatggacg gccttcaacg agcgctccgt ggccgcgcac ctggcggaca tcattttccc    11280
cgaacgcctg cttaaaaccc tgcaacaggg tctgccagac ttcaccagtc aaagcatgtt    11340
gcagaacttt aggaacttta tcctagagcg ctcaggaatc ttgcccgcca cctgctgtgc    11400
acttcctagc gactttgtgc ccattaagta ccgcgaatgc ctccgccgc tttgggcca    11460 ctgctacctt ctgcagctag ccaactacct tgcctaccac tctgacataa tggaagacgt    11520
gagcggtgac ggtctactgg agtgtcactg tcgctgcaac ctatgcaccc cgcaccgctc    11580
cctggtttgc aattcgcagc tgcttaacga aagtcaaatt atcggtacct ttgagctgca    11640
gggtccctcg cctgacgaaa agtccgcggc tccggggttg aaactcactc cggggctgtg    11700
gacgtcggct taccttcgca aatttgtacc tgaggactac cacgcccacg agattaggtt    11760
ctacgaagac caatcccgcc cgccaaatgc ggagcttacc gcctgcgtca ttacccaggg    11820
ccacattctt ggccaattgc aagccatcaa caaagcccgc caagagtttc tgctacgaaa    11880
gggacggggg gtttacttgg accccagtc cggcgaggag ctcaacccaa tcccccgcc    11940 gccgcagccc tatcagcagc agccgcgggc ccttgcttcc caggatggca cccaaaaaga    12000
agctgcagct gccgccgcca cccacggacg aggaggaata ctgggacagt caggcagagg    12060
aggttttgga cgaggaggag gaggacatga tggaagactg ggagagccta gacgaggaag    12120
cttccgaggt cgaagaggtg tcagacgaaa caccgtcacc ctcggtcgca ttcccctcgc    12180
cggcgcccca gaaatcggca accggttcca gcatggctac aacctccgct cctcaggcgc    12240
cgccggcact gccgttcgc cgacccaacc gtagatggga caccactgga accagggccg    12300
gtaagtccaa gcagccgccg ccgttagccc aagagcaaca acagcgccaa ggctaccgct    12360
catggcgcgg gcacaagaac gccatagttg cttgcttgca agactgtggg ggcaacatct    12420
ccttcgcccg ccgctttctt ctctaccatc acggcgtggc cttccccgt aacatcctgc    12480
```

```
attactaccg tcatctctac agcccatact gcaccggcgg cagcggcagc ggcagcaaca   12540
gcagcggcca cacagaagca aaggcgaccg gatagcaaga ctctgacaaa gcccaagaaa   12600
tccacagcgg cggcagcagc aggaggagga gcgctgcgtc tggcgcccaa cgaacccgta   12660
tcgacccgcg agcttagaaa caggattttt cccactctgt atgctatatt tcaacagagc   12720
aggggccaag aacaagagct gaaaataaaa aacaggtctc tgcgatccct cacccgcagc   12780
tgcctgtatc acaaaagcga agatcagctt cggcgcacgc tggaagacgc ggaggctctc   12840
ttcagtaaat actgcgcgct gactcttaag gactagtttc gcgcccttc tcaaatttaa    12900 gcgcgaaaac tacgtcatct ccagcggcca caccggcgc cagcacctgt cgtcagcgcc     12960
attatgagca aggaaattcc cacgccctac atgtggagtt accagccaca aatgggactt   13020
gcggctggag ctgcccaaga ctactcaacc cgaataaact acatgagcgc gggaccccac   13080
atgatatccc gggtcaacgg aatccgcgcc caccgaaacc gaattctctt ggaacaggcg   13140
gctattacca ccacacctcg taataaactt aatccccgta gttggcccgc tgccctggtg   13200
taccaggaaa gtcccgctcc caccactgtg gtacttccca gagacgccca ggccgaagtt   13260
cagatgacta actcaggggc gcagcttgcg ggcggctttc gtcacagggt gcggtcgccc   13320
gggcagggta taactcacct gacaatcaga gggcgaggta ttcagctcaa cgacgagtcg   13380
gtgagctcct cgcttggtct ccgtccggac gggacattc agatcggcgg cgccggccgc    13440
tcttcattca cgcctcgtca ggcaatccta actctgcaga cctcgtcctc tgagccgcgc   13500
tctggaggca ttggaactct gcaatttatt gaggagtttg tgccatcggt ctactttaac   13560
cccttctcgg gacctcccgg ccactatccg gatcaattta ttcctaactt tgacgcgta    13620 aaggactcgg cggatggcta cgactgaatg ttaagtggag aggcagagca actgcgcctg   13680
aaacacctgg tccactgtcg ccgccacaag tgctttgccc gcgactccgg tgagttttgc   13740
tactttgaat tgcccgagga tcatatcgag ggcccggcgc acggcgtccg gcttaccgcc   13800
cagggagagc ttgcccgtag cctgattcgg gagtttaccc agcgcccct gctagttgag    13860 cgggacaggg gaccctgtgt tctcactgtg atttgcaact gtcctaaccc tggattacat   13920
caagatcttt gttgccatct ctgtgctgag tataataaat acagaaatta aaatatactg   13980
gggctcctat cgccatcctg taaacgccac cgtcttcacc cgcccaagca aaccaaggcg   14040
aaccttacct ggtacttta acatctctcc ctctgtgatt tacaacagtt tcaacccaga    14100
cggagtgagt ctacgagaga acctctccga gctcagctac tccatcagaa aaaacaccac   14160
cctccttacc tgccgggaac gtacgagtgc gtcaccggcc gctgcaccac acctaccgcc   14220
tgaccgtaaa ccagactttt tccggacaga cctcaataac tctgtttacc agaacaggag   14280
gtgagcttag aaaaccctta gggtattagg ccaaaggcgc agctactgtg gggtttatga   14340
acaattcaag caactctacg ggctattcta attcaggttt ctctagaaat ggacggaatt   14400
attacagagc agcgcctgct agaaagacgc agggcagcgg ccgagcaaca gcgcatgaat   14460
caagagctcc aagacatggt taacttgcac cagtgcaaaa ggggtatctt ttgtctggta   14520
aagcaggcca aagtcaccta cgacagtaat accaccggac accgccttag ctacaagttg   14580
ccaaccaagc gtcagaaatt ggtggtcatg gtgggagaaa agcccattac cataactcag   14640
cactcggtag aaaccgaagg ctgcattcac tcaccttgtc aaggacctga ggatctctgc   14700
acccttatta agaccctgtg cggtctcaaa gatcttattc cctttaacta ataaaaaaaa   14760
ataataaagc atcacttact taaaatcagt tagcaaattc ctgtccagtt tattcagcag   14820
cacctccttg ccctcctccc agctctggta ttgcagcttc ctcctggctg caaactttct   14880
```

```
ccacaatcta aatggaatgt cagtttcctc ctgttcctgt ccatccgcac ccactatctt    14940
catgttgttg cagatgaagc gcgcaagacc gtctgaagat accttcaacc ccgtgtatcc    15000
atatgacacg gaaaccggtc ctccaactgt gccttttctt actcctccct ttgtatcccc    15060
caatgggttt caagagagtc cccctggggt actctctttg cgcctatccg aacctctagt    15120
tacctccaat ggcatgcttg cgctcaaaat gggcaacggc ctctctctgg acgaggccgg    15180
caaccttacc tcccaaaatg taaccactgt gagcccacct ctcaaaaaaa ccaagtcaaa    15240
cataaacctg gaaatatctg caccccctcac agttacctca gaagccctaa ctgtggctgc    15300
cgccgcacct ctaatggtcg cgggcaacac actcaccatg caatcacagg ccccgctaac    15360
cgtgcacgac tccaaactta gcattgccac ccaaggaccc ctcacagtgt cagaaggaaa    15420
gctagccctg caaacatcag gcccctcac caccaccgat agcagtaccc ttactatcac    15480
tgcctcaccc cctctaacta ctgccactgg tagcttgggc attgacttga agagcccat    15540 ttatacacaa aatggaaaac taggactaaa gtacggggct cctttgcatg taacagacga    15600
cctaaacact ttgaccgtag caactggtcc aggtgtgact attaataata cttccttgca    15660
aactaaagtt actggagcct tgggttttga ttcacaaggc aatatgcaac ttaatgtagc    15720
aggaggacta aggattgatt ctcaaaacag acgccttata cttgatgtta gttatccgtt    15780
tgatgctcaa aaccaactaa atctaagact aggacagggc cctcttttta taaactcagc    15840
ccacaacttg gatattaact acaacaaagg cctttacttg tttacagctt caaacaattc    15900
caaaaagctt gaggttaacc taagcactgc caagggggttg atgtttgacg ctacagccat    15960
agccattaat gcaggagatg ggcttgaatt tggttcacct aatgcaccaa acacaaatcc    16020
cctcaaaaca aaaattggcc atggcctaga atttgattca aacaaggcta tggttcctaa    16080
actaggaact ggccttagtt ttgacagcac aggtgccatt acagtaggaa acaaaaataa    16140
tgataagcta actttgtgga ccacaccagc tccatctcct aactgtagac taaatgcaga    16200
gaaagatgct aaactcactt tggtcttaac aaaatgtggc agtcaaatac ttgctacagt    16260
ttcagttttg gctgttaaag gcagtttggc tccaatatct ggaacagttc aaagtgctca    16320
tcttattata agatttgacg aaaatggagt gctactaaac aattccttcc tggacccaga    16380
atattggaac tttagaaatg gagatcttac tgaaggcaca gcctatacaa acgctgttgg    16440
atttatgcct aacctatcag cttatccaaa atctcacggt aaaactgcca aaagtaacat    16500
tgtcagtcaa gtttacttaa acggagacaa aactaaacct gtaacactaa ccattacact    16560
aaacggtaca caggaaacag gagacacaac tccaagtgca tactctatgt cattttcatg    16620
ggactggtct ggccacaact acattaatga aatatttgcc acatcctctt acacttttc    16680 atacattgcc caagaataaa gaatcgtttg tgttatgttt caacgtgttt atttttcaat    16740
tgcagaaaat ttcaagtcat ttttcattca gtagtatagc cccaccacca catagcttat    16800
acagatcacc gtaccttaat caaactcaca gaacccctagt attcaacctg ccacctccct    16860
cccaacacac agagtacaca gtcctttctc cccggctggc cttaaaaagc atcatatcat    16920
gggtaacaga catattctta ggtgttatat tccacgggtt ttcctgtcga gccaaacgct    16980
catcagtgat attaataaac tccccgggca gctcacttaa gttcatgtcg ctgtccagct    17040
gctgagccac aggctgctgt ccaacttgcg gttgcttaac gggcggcgaa ggagaagtcc    17100
acgcctacat gggggtagag tcataatcgt gcatcaggat agggcggtgg tgctgcagca    17160
gcgcgcgaat aaactgctgc cgccgccgct ccgtcctgca ggaatacaac atggcagtgg    17220
```

```
tctcctcagc gatgattcgc accgcccgca gcataaggcg ccttgtcctc cgggcacagc  17280
agcgcaccct gatctcactt aaatcagcac agtaactgca gcacagcacc acaatattgt  17340
tcaaaatccc acagtgcaag gcgctgtatc caaagctcat ggcggggacc acagaaccca  17400
cgtggccatc ataccacaag cgcaggtaga ttaagtggcg acccctcata acacgctgg   17460 acataaacat tacctctttt ggcatgttgt aattcaccac ctcccggtac catataaacc  17520
tctgattaaa catggcgcca tccaccacca tcctaaacca gctggccaaa acctgccgc   17580 cggctataca ctgcagggaa ccgggactgg aacaatgaca gtggagagcc caggactcgt  17640
aaccatggat catcatgctc gtcatgatat caatgttggc acaacacagg cacacgtgca  17700
tacacttcct caggattaca agctcctccc gcgttagaac catatcccag ggaacaaccc  17760
attcctgaat cagcgtaaat cccacactgc agggaagacc tcgcacgtaa ctcacgttgt  17820
gcattgtcaa agtgttacat tcgggcagca gcggatgatc ctccagtatg gtagcgcggg  17880
tttctgtctc aaaaggaggt agacgatccc tactgtacgg agtgcgccga gacaaccgag  17940
atcgtgttgg tcgtagtgtc atgccaaatg gaacgccgga cgtagtcata tttcctgaag  18000
caaaaccagg tgcgggcgtg acaaacagat ctgcgtctcc ggtctcgccg cttagatcgc  18060
tctgtgtagt agttgtagta tatccactct ctcaaagcat ccaggcgccc cctggcttcg  18120
ggttctatgt aaactccttc atgcgccgct gccctgataa catccaccac cgcagaataa  18180
gccacaccca gccaacctac acattcgttc tgcgagtcac acgggagg agcgggaaga   18240 gctggaagaa ccatgttttt ttttttattc caaagagatta tccaaaacct caaaatgaag  18300
atctattaag tgaacgcgct cccctccggt ggcgtggtca aactctacag ccaaagaaca  18360
gataatggca tttgtaagat gttgcacaat ggcttccaaa aggcaaacgg ccctcacgtc  18420
caagtggacg taaaggctaa acccttcagg gtgaatctcc tctataaaca ttccagcacc  18480
ttcaaccatg cccaaataat tctcatctcg ccaccttctc aatatatctc taagcaaatc  18540
ccgaatatta agtccggcca ttgtaaaaat ctgctccaga gcgccctcca ccttcagcct  18600
caagcagcga atcatgattg caaaaattca ggttcctcac agacctgtat aagattcaaa  18660
agcggaacat taacaaaaat accgcgatcc cgtaggtccc ttcgcagggc cagctgaaca  18720
taatcgtgca ggtctgcacg gaccagcgcg gccacttccc cgccaggaac catgacaaaa  18780
gaacccacac tgattatgac acgcatactc ggagctatgc taaccagcgt agccccgatg  18840
taagcttgtt gcatgggcgg cgatataaaa tgcaaggtgc tgctcaaaaa atcaggcaaa  18900
gcctcgcgca aaaagaaag cacatcgtag tcatgctcat gcagataaag gcaggtaagc   18960
tccggaacca ccacagaaaa agacaccatt tttctctcaa acatgtctgc gggtttctgc  19020
ataaacacaa aataaaataa caaaaaaaca tttaaacatt agaagcctgt cttacaacag  19080 gaaaacaac ccttataagc ataagacgga ctacggccat gccggcgtga ccgtaaaaaa   19140
actggtcacc gtgattaaaa agcaccaccg acagctcctc ggtcatgtcc ggagtcataa  19200
tgtaagactc ggtaaacaca tcaggttgat tcacatcggg cagtgctaaa aagcgaccga  19260
aatagcccgg gggaatacat acccgcaggc gtagagacaa cattacagcc cccataggag  19320
gtataacaaa attaatagga gagaaaaaca cataaacacc tgaaaaaccc tcctgcctag  19380
gcaaaatagc accctcccgc tccagaacaa catacagcgc ttccacagcg gcagccataa  19440
cagtcagcct taccagtaaa aagaaaaccc tattaaaaaa acaccactcg acacggcacc  19500
agctcaatca gtcacagtgt aaaaaagggc caagtgcaga gcgagtatat ataggactaa  19560
aaaatgacgt aacggttaaa gtccacaaaa aacacccaga aaaccgcacg cgaacctacg  19620
```

```
cccagaaacg aaagccaaaa aacccacaac ttcctcaaat cgtcacttcc gttttcccac   19680
gttacgtcac ttcccatttt aagaaaacta caattcccaa cacatacaag ttactccgcc   19740
ctaaaaccta cgtcacccgc cccgttccca cgcccgcgc cacgtcacaa actccacccc    19800
ctcattatca tattggcttc aatccaaaat aaggtatatt attgatgatg ttaattaaga   19860
attcggatct gcgacgcgag gctggatggc cttccccatt atgattcttc tcgcttccgg   19920
cggcatcggg atgcccgcgt tgcaggccat gctgtccagg caggtagatg acgaccatca   19980
gggacagctt cacggccagc aaaaggccag gaaccgtaaa aaggccgcgt tgctggcgtt   20040
tttccatagg ctccgccccc ctgacgagca tcacaaaaat cgacgctcaa gtcagaggtg   20100
gcgaaacccg acaggactat aaagatacca ggcgtttccc cctggaagct ccctcgtgcg   20160
ctctcctgtt ccgaccctgc cgcttaccgg atacctgtcc gcctttctcc cttcgggaag   20220
cgtggcgctt tctcatagct cacgctgtag gtatctcagt tcggtgtagg tcgttcgctc   20280
caagctgggt tgtgtgcacg aaccccccgt tcagcccgac cgctgcgcct tatccggtaa   20340
ctatcgtctt gagtccaacc cggtaagaca cgacttatcg ccactggcag cagccactgg   20400
taacaggatt agcagagcga ggtatgtagg cggtgctaca gagttcttga agtggtggcc   20460
taactacggc tacactagaa gaacagtatt tggtatctgc gctctgctga agccagttac   20520
cttcggaaaa agagttggta gctcttgatc cggcaaacaa accaccgctg gtagcggtgg   20580
tttttttgtt tgcaagcagc agattacgcg cagaaaaaaa ggatctcaag aagatccttt   20640
gatcttttct acggggtctg acgctcagtg gaacgaaaac tcacgttaag ggattttggt   20700
catgagatta tcaaaaagga tcttcaccta gatccttttta aatcaatcta agtatatat   20760 gagtaaactt ggtctgacag ttaccaatgc ttaatcagtg aggcacctat ctcagcgatc   20820
tgtctatttc gttcatccat agttgcctga ctccccgtcg tgtagataac tacgatacgg   20880
gagggcttac catctggccc cagtgctgca atgataccgc gagacccacg ctcaccggct   20940
ccagatttat cagcaataaa ccagccagcc ggaagggccg agcgcagaag tggtcctgca   21000
actttatccg cctccatcca gtctattaat tgttgccggg aagctagagt aagtagttcg   21060
ccagttaata gtttgcgcaa cgttgttgcc attgctgcag gcatcgtggt gtcacgctcg   21120
tcgtttggta tggcttcatt cagctccggt tcccaacgat caaggcgagt tacatgatcc   21180
cccatgttgt gcaaaaaagc ggttagctcc ttcggtcctc cgatcgttgt cagaagtaag   21240
ttggcagcag tgttatcact catggttatg gcagcactgc ataattctct tactgtcatg   21300
ccatccgtaa gatgcttttc tgtgactggt gagtactcaa ccaagtcatt ctgagaatag   21360
tgtatgcggc gaccgagttg ctcttgcccg gcgtcaacac gggataatac cgcaccacat   21420
agcagaactt taaaagtgct catcattgga aaacgttctt cggggcgaaa actctcaagg   21480
atcttaccgc tgttgagatc cagttcgatg taacccactc gtgcacccaa ctgatcttca   21540
gcatctttta ctttcaccag cgtttctggg tgagcaaaaa caggaaggca aaatgccgca   21600
aaaaagggaa taagggcgac acgaaaatgt tgaatactca tactcttcct ttttcaatat   21660
tattgaagca tttatcaggg ttattgtctc atgagcggat acatatttga atgtatttag   21720
aaaaataaac aaatagdgggt tccgcgcaca tttccccgaa aagtgccacc tgacgtctaa   21780
gaaaccatta ttatcatgac attaacctat aaaaataggc gtatcacgag gccctttcgt   21840
cttcaa                                                              21846
```

<210> SEQ ID NO 3

```
<211> LENGTH: 7905
<212> TYPE: DNA
<213> ORGANISM: Artificial Sequence
<220> FEATURE:
<223> OTHER INFORMATION: Synthesized in laboratory
<220> FEATURE:
<221> NAME/KEY: misc_feature
<222> LOCATION: (4404)..(4404)
<223> OTHER INFORMATION: n is a, c, g, or t
<220> FEATURE:
<221> NAME/KEY: misc_feature
<222> LOCATION: (5675)..(5675)
<223> OTHER INFORMATION: n is a, c, g, or t

<400> SEQUENCE: 3
```

| | | | | | |
|---|---|---|---|---|---|
| aagcggaaga | gcgcccaata | cgcaaaccgc | tctctcccgc | gcgttggccg | attcattaat | 60 |
| gcagctggcg | cgctcgctcg | ctcactgagg | ccgcccgggc | aaagcccggg | cgtcgggcga | 120 |
| cctttggtcg | cccggcctca | gtgagcgagc | gagcgcgcag | agagggagtg | gccaactcca | 180 |
| tcactagggg | ttccttgtag | ttaatgatta | acccgccatg | ctacttatct | acgtagccat | 240 |
| gctctagtcg | accaattctc | atgtttgaca | gcttatcatc | gcagatccgg | caacgttgt | 300 |
| tgcattgctg | caggcgcaga | actggtaggt | atggaagatc | tatacattga | atcaatattg | 360 |
| gcaattagcc | atattagtca | ttggttatat | agcataaatc | aatattggct | attggccatt | 420 |
| gcatacgttg | tatctatatc | ataatatgta | catttatatt | ggctcatgtc | aatatgacc | 480 |
| gccatgttga | cattgattat | tgactagtta | ttaatagtaa | tcaattacgg | ggtcattagt | 540 |
| tcatagccca | tatatggagt | tccgcgttac | ataacttacg | gtaaatggcc | cgcctggctg | 600 |
| accgcccaac | gacccccgcc | cattgacgtc | aataatgacg | tatgttccca | tagtaacgcc | 660 |
| aatagggact | ttccattgac | gtcaatgggt | ggagtattta | cggtaaactg | cccacttggc | 720 |
| agtacatcaa | gtgtatcata | tgccaagtcc | gccccctatt | gacgtcaatg | acggtaaatg | 780 |
| gcccgcctgg | cattatgccc | agtacatgac | cttacgggac | tttcctactt | ggcagtacat | 840 |
| ctacgtatta | gtcatcgcta | ttaccatggt | gatgcggttt | tggcagtaca | ccaatgggcg | 900 |
| tggatagcgg | tttgactcac | ggggatttcc | aagtctccac | cccattgacg | tcaatgggag | 960 |
| tttgttttgg | caccaaaatc | aacgggactt | tccaaaatgt | cgtaataacc | ccgccccgtt | 1020 |
| gacgcaaatg | ggcggtaggc | gtgtacggtg | ggaggtctat | ataagcagag | ctcgtttagt | 1080 |
| gaaccgtcag | atctctagaa | gctgggtacc | gcgggcccgg | gatccaccgg | tcgccaccat | 1140 |
| ggtgagcaag | ggcgaggagc | tgttcaccgg | ggtggtgccc | atcctggtcg | agctggacgg | 1200 |
| cgacgtaaac | ggccacaagt | tcagcgtgtc | cggcgagggc | gagggcgatg | ccacctacgg | 1260 |
| caagctgacc | ctgaagttca | tctgcaccac | cggcaagctg | cccgtgccct | ggcccaccct | 1320 |
| cgtgaccacc | ctgacctacg | gcgtgcagtg | cttcagccgc | taccccgacc | acatgaagca | 1380 |
| gcacgacttc | ttcaagtccg | ccatgcccga | aggctacgtc | caggagcgca | ccatcttctt | 1440 |
| caaggacgac | ggcaactaca | agacccgcgc | cgaggtgaag | ttcgagggcg | acaccctggt | 1500 |
| gaaccgcatc | gagctgaagg | gcatcgactt | caaggaggac | ggcaacatcc | tggggcacaa | 1560 |
| gctggagtac | aactacaaca | gccacaacgt | ctatatcatg | gccgacaagc | agaagaacgg | 1620 |
| catcaaggtg | aacttcaaga | tccgccacaa | catcgaggac | ggcagcgtgc | agctcgccga | 1680 |
| ccactaccag | cagaacaccc | ccatcggcga | cggccccgtg | ctgctgcccg | acaaccacta | 1740 |
| cctgagcacc | cagtccgccc | tgagcaaaga | ccccaacgag | aagcgcgatc | acatggtcct | 1800 |
| gctggagttc | gtgaccgccg | ccgggatcac | tctcggcatg | gacgagctgt | acaagtaaag | 1860 |
| cggccgctcg | aggccggcaa | ggccggatcc | agacatgata | agatacattg | atgagtttgg | 1920 |

```
acaaaccaca actagaatgc agtgaaaaaa atgctttatt tgtgaaattt gtgatgctat    1980
tgctttattt gtaaccatta taagctgcaa taaacaagtt aacaacaaca attgcattca    2040
ttttatgttt caggttcagg gggaggtggg gaggtttttt aaagcaagta aaacctctac    2100
aaatgtggta tggctgatta tgatccggct gcctcgcgcg tttcggtgat gacggtgaaa    2160
acctctgaca catgcagctc ccggagacgg tcacagcttg tctgtaagcg gatgccggga    2220
gcagacaagc ccgtcaggc gcgtcagcgg gtgttggcgg gtgtcgggc gcagccatga      2280 ccggtcgact agcttggcac gccagaaatc cgcgcggtgg ttttgggg tcggggtgt       2340 ttggcagcca cagacgcccg tgttcgtgt gcgccagta catgcggtcc atgcccaggc      2400
catccaaaaa ccatgggtct gtctgctcag tccagtcgtg gaccagaccc cacgcaacgc    2460
ccaaaataat aaccccacg aaccataaac cattccccat gggggacccc gtccctaacc     2520
cacggggcca gtggctatgg cagggcctgc cgccccgacg ttggctgcga gccctgggcc    2580
ttcacccgaa cttgggggt ggggtgggga aaggaagaa acgcgggcgt attggcccca     2640 atgggtctc ggtgggtat cgacagagtg ccagccctgg gaccgaaccc cgcgtttatg    2700
aacaaacgac ccaacacccg tgcgttttat tctgtctttt tattgccgtc atagcgcggg    2760
ttccttccgg tattgtctcc ttccgtgttt cagttagcct cccccatctc ccctattcct    2820
ttgccctcgg acgagtgctg gggcgtcggt ttccactatc ggcgagtact tctacacagc    2880
catcggtcca gacggccgcg cttctgcggg cgatttgtgt acgcccgaca gtcccggctc    2940
cggatcggac gattgcgtcg catcgaccct gcgcccaagc tgcatcatcg aaattgccgt    3000
caaccaagct ctgatagagt tggtcaagac caatgcggag catatacgcc cggagccgcg    3060
gcgatcctgc aagctccgga tgcctccgct cgaagtagcg cgtctgctgc tccatacaag    3120
ccaaccacgg cctccagaag aagatgttgg cgacctcgta ttgggaatcc ccgaacatcg    3180
cctcgctcca gtcaatgacc gctgttatgc ggccattgtc cgtcaggaca ttgttggagc    3240
cgaaatccgc gtgcacgagg tgccggactt cggggcagtc ctcggcccaa agcatcagct    3300
catcgagagc ctgcgcgacg gacgcactga cggtgtcgtc catcacagtt tgccagtgat    3360
acacatgggg atcagcaatc gcgcatatga aatcacgcca tgtagtgtat tgaccgattc    3420
cttgcggtcc gaatgggccg aaccccgctcg tctggctaag atcggccgca gcgatcgcat    3480
ccatggcctc cgcgaccggc tgcagaacag cgggcagttc ggtttcaggc aggtcttgca    3540
acgtgacacc ctgtgcacgg cgggagatgc aataggtcag gctctcgctg aattccccaa    3600
tgtcaagcac ttccggaatc gggagcgcgg ccgatgcaaa gtgccgataa acataacgat    3660
ctttgtagaa accatcggcg cagctattta cccgcaggac atatccacgc cctcctacat    3720
cgaagctgaa agcacgagat tcttcgccct ccgagagctg catcaggtcg gagacgctgt    3780 cgaactttc gatcagaaac ttctcgacag acgtcgcggt gagttcaggc ttttcatat     3840 ctcattgccc gggatctgcg gcacgctgtt gacgctgtta gcgggtcgc tgcagggtcg     3900 ctcggtgttc gaggccacac gcgtcacctt aatatgcgaa gtggacctgg gaccgcgccg    3960
ccccgactgc atctgcgtgt tcgaattcgc caatgacaag acgctgggcg gggtttgtgt    4020
catcatagaa ctaaagacat gcaaatatat ttcttccggg gacaccgcca gcaaacgcga    4080
gcaacgggcc acggggatga agcagggcat ggcggccgac gcgctgggct acgtcttgct    4140
ggcgttcgct agagcatggc tacgtagata agtagcatgg cgggttaatc attaactaca    4200
aggaacccct agtgatggag ttggccactc cctctctgcg cgctcgctcg ctcactgagg    4260
```

```
ccgggcgacc aaaggtcgcc cgacgcccgg gctttgcccg ggcggcctca gtgagcgagc    4320
gagcgcgcca gctggcgtaa tagcgaagag gcccgcaccg atcgcccttc ccaacagttg    4380
cgcagcctga atggcgaatg gaanttccag acgattgagc gtcaaaatgt aggtatttcc    4440
atgagcgttt ttcctgttgc aatggctggc ggtaatattg ttctggatat taccagcaag    4500
gccgatagtt tgagttcttc tactcaggca agtgatgtta ttactaatca agaagtatt    4560 gcgacaacgg ttaatttgcg tgatggacag actcttttac tcggtggcct cactgattat    4620
aaaaacactt ctcaggattc tggcgtaccg ttcctgtcta aaatcccttt aatcggcctc    4680
ctgtttagct cccgctctga ttctaacgag gaaagcacgt tatacgtgct cgtcaaagca    4740
accatagtac gcgccctgta gcggcgcatt aagcgcggcg ggtgtggtgg ttacgcgcag    4800
cgtgaccgct acacttgcca gcgccctagc gcccgctcct ttcgctttct tcccttcctt    4860
tctcgccacg ttcgccggct ttccccgtca gctctaaat cggggctcc ctttagggtt    4920 ccgatttagt gctttacggc acctcgaccc caaaaaactt gattagggtg atggttcacg    4980
tagtgggcca tcgccctgat agacggtttt tcgcccttg acgttggagt ccacgttctt    5040
taatagtgga ctcttgttcc aaactggaac aacactcaac cctatctcgg tctattcttt    5100
tgatttataa gggattttgc cgatttcggc ctattggtta aaaaatgagc tgatttaaca    5160
aaaatttaac gcgaatttta acaaaatatt aacgtttaca atttaaatat ttgcttatac    5220
aatcttcctg ttttttgggggc ttttctgatt atcaaccggg gtacatatga ttgacatgct    5280
agttttacga ttaccgttca tcgattctct tgtttgctcc agactctcag gcaatgacct    5340
gatagccttt gtagagacct ctcaaaaata gctaccctct ccggcatgaa tttatcagct    5400
agaacggttg aatatcatat tgatggtgat ttgactgtct ccggccttc tcacccgttt    5460 gaatctttac ctacacatta ctcaggcatt gcatttaaaa tatatgaggg ttctaaaaat    5520
ttttatcctt gcgttgaaat aaaggcttct cccgcaaaag tattacaggg tcataatgtt    5580
tttggtacaa ccgatttagc tttatgctct gaggctttat tgcttaattt tgctaattct    5640
ttgccttgcc tgtatgattt attggatgtt ggaanttcct gatgcggtat tttctcctta    5700
cgcatctgtg cggtatttca caccgcatat ggtgcactct cagtacaatc tgctctgatg    5760
ccgcatagtt aagccagccc cgacacccgc caacacccgc tgacgcgccc tgacgggctt    5820
gtctgctccc ggcatccgct tacagacaag ctgtgaccgt ctccgggagc tgcatgtgtc    5880
agaggttttc accgtcatca ccgaaacgcg cgagacgaaa gggcctcgtg atacgcctat    5940
ttttataggt taatgtcatg ataataatgg tttcttagac gtcaggtggc acttttcggg    6000
gaaatgtgcg cggaacccct atttgtttat ttttctaaat acattcaaat atgtatccgc    6060
tcatgagaca ataaccctga taatgcttc aataatattg aaaaggaag agtatgagta    6120 ttcaacattt ccgtgtcgcc cttattccct ttttgcggc attttgcctt cctgtttttg    6180
ctcacccaga aacgctggtg aaagtaaaag atgctgaaga tcagttgggt gcacgagtgg    6240
gttacatcga actggatctc aacagcggta agatccttga gttttcgc cccgaagaac    6300 gttttccaat gatgagcact tttaaagttc tgctatgtgg cgcggtatta tcccgtattg    6360
acgccgggca agagcaactc ggtcgccgca tacactattc tcagaatgac ttggttgagt    6420
actcaccagt cacagaaaag catcttacgg atggcatgac agtaagagaa ttatgcagtg    6480
ctgccataac catgagtgat aacactgcgg ccaacttact tctgacaacg atcggaggac    6540
cgaaggagct aaccgctttt ttgcacaaca tgggggatca tgtaactcgc cttgatcgtt    6600
gggaaccgga gctgaatgaa gccataccaa acgacgagcg tgacaccacg atgcctgtag    6660
```

```
caatggcaac aacgttgcgc aaactattaa ctggcgaact acttactcta gcttcccggc   6720
aacaattaat agactggatg gaggcggata agttgcagg accacttctg cgctcggccc    6780
ttccggctgg ctggtttatt gctgataaat ctggagccgg tgagcgtggg tctcgcggta   6840
tcattgcagc actggggcca gatggtaagc cctcccgtat cgtagttatc tacacgacgg   6900
ggagtcaggc aactatggat gaacgaaata gacagatcgc tgagataggt gcctcactga   6960
ttaagcattg gtaactgtca gaccaagttt actcatatat actttagatt gatttaaaac   7020
ttcattttta atttaaaagg atctaggtga agatccttttt tgataatctc atgaccaaaa   7080
tcccttaacg tgagttttcg ttccactgag cgtcagaccc cgtagaaaag atcaaaggat   7140
cttcttgaga tccttttttt ctgcgcgtaa tctgctgctt gcaaacaaaa aaaccaccgc   7200
taccagcggt ggtttgtttg ccggatcaag agctaccaac tctttttccg aaggtaactg   7260
gcttcagcag agcgcagata ccaaatactg tccttctagt gtagccgtag ttaggccacc   7320
acttcaagaa ctctgtagca ccgcctacat acctcgctct gctaatcctg ttaccagtgg   7380
ctgctgccag tggcgataag tcgtgtctta ccgggttgga ctcaagacga tagttaccgg   7440
ataaggcgca gcggtcgggc tgaacggggg gttcgtgcac acagcccagc ttggagcgaa   7500
cgacctacac cgaactgaga tacctacagc gtgagctatg agaaagcgcc acgcttcccg   7560
aagggagaaa ggcggacagg tatccggtaa gcggcagggt cggaacagga gagcgcacga   7620
gggagcttcc agggggaaac gcctggtatc tttatagtcc tgtcgggttt cgccacctct   7680
gacttgagcg tcgatttttg tgatgctcgt caggggggcg gagcctatgg aaaaacgcca   7740
gcaacgcggc cttttacgg ttcctggcct tttgctggcc ttttgctcac atgttctttc     7800
ctgcgttatc ccctgattct gtggataacc gtattaccgc ctttgagtga gctgataccg   7860
ctcgccgcag ccgaacgacc gagcgcagcg agtcagtgag cgagg                   7905

<210> SEQ ID NO 4
<211> LENGTH: 5964
<212> TYPE: DNA
<213> ORGANISM: Artificial Sequence
<220> FEATURE:
<223> OTHER INFORMATION: Synthesized in laboratory
<220> FEATURE:
<221> NAME/KEY: misc_feature
<222> LOCATION: (2395)..(2395)
<223> OTHER INFORMATION: n is a, c, g, or t
<220> FEATURE:
<221> NAME/KEY: misc_feature
<222> LOCATION: (3666)..(3666)
<223> OTHER INFORMATION: n is a, c, g, or t

<400> SEQUENCE: 4
cgcgctcgct cgtcactga ggccgcccgg gcaaagcccg ggcgtcgggc gacctttggt      60
cgcccggcct cagtgagcga gcgagcgcgc agagagggag tgggtcgttc tagtcgacca   120
attctcatgt ttgacagctt atcatcgcag atccgggcaa cgttgttgca ttgctgcagg   180
cgcagaactg gtaggtatgg aagatctata cattgaatca atattggcaa ttagccatat   240
tagtcattgg ttatatagca taaatcaata ttggctattg ccattgcat acgttgtatc    300 tatatcataa tatgtacatt tatattggct catgtccaat atgaccgcca tgttgacatt   360
gattattgac tagttattaa tagtaatcaa ttacgggtc attagttcat agcccatata    420
tggagttccg cgttacataa cttacggtaa atggcccgcc tggctgaccg cccaacgacc   480
cccgcccatt gacgtcaata atgacgtatg ttcccatagt aacgccaata gggactttcc   540
```

```
attgacgtca atgggtggag tatttacggt aaactgccca cttggcagta catcaagtgt      600
atcatatgcc aagtccgccc cctattgacg tcaatgacgg taaatggccc gcctggcatt      660
atgcccagta catgacctta cgggactttc ctacttggca gtacatctac gtattagtca      720
tcgctattac catggtgatg cggttttggc agtacaccaa tgggcgtgga tagcggtttg      780
actcacgggg atttccaagt ctccaccccaa ttgacgtcaa tgggagtttg ttttggcacc      840
aaaatcaacg ggactttcca aaatgtcgta taaccccgc cccgttgacg caaatgggcg      900
gtaggcgtgt acggtgggag gtctatataa gcagagctcg tttagtgaac cgtcagatct      960
ctagaagctg gtaccgcggg cccgggatc accggtcgc caccatggtg agcaagggcg     1020
aggagctgtt caccggggtg gtgcccatcc tggtcgagct ggacggcgac gtaaacggcc     1080
acaagttcag cgtgtccggc gagggcgagg gcgatgccac ctacggcaag ctgaccctga     1140
agttcatctg caccaccggc aagctgcccg tgccctggcc caccctcgtg accaccctga     1200
cctacggcgt gcagtgcttc agccgctacc ccgaccacat gaagcagcac gacttcttca     1260
agtccgccat gcccgaaggc tacgtccagg agcgcaccat cttcttcaag gacgacggca     1320
actacaagac ccgcgccgag gtgaagttcg agggcgacac cctggtgaac cgcatcgagc     1380
tgaagggcat cgacttcaag gaggacggca acatcctggg gcacaagctg gagtacaact     1440
acaacagcca caacgtctat atcatggccg acaagcagaa gaacggcatc aaggtgaact     1500
tcaagatccg ccacaacatc gaggacggca gcgtgcagct cgccgaccac taccagcaga     1560
acacccccat cggcgacggc cccgtgctgc tgcccgacaa ccactacctg agcacccagt     1620
ccgccctgag caaagacccc aacgagaagc gcgatcacat ggtcctgctg gagttcgtga     1680
ccgccgccgg gatcactctc ggcatggacg agctgtacaa gtaaagcggc cgctcgaggc     1740
cggcaaggcc ggatccagac atgataagat acattgatga gtttggacaa accacaacta     1800
gaatgcagtg aaaaaaatgc tttatttgtg aaatttgtga tgctattgct ttatttgtaa     1860
ccattataag ctgcaataaa caagttaaca acaacaattg cattcatttt atgtttcagg     1920
ttcaggggga ggtggggagg ttttttaaag caagtaaaac ctctacaaat gtggtatggc     1980
tgattatgat ccggctgcct cgcgcgtttc ggtgatgacg gtgaaaacct ctgacacatg     2040
cagctcccgg agacggtcac agcttgtctg taagcggatg ccgggagcag acaagcccgt     2100
cagggcgcgt cagcgggtgt tggcgggtgt cggggcgcag ccatgaccgg tcgagtagat     2160
aagtagcatg gcgggttaat cattaactac aaggaacccc tagtgatgga gttggccact     2220
ccctctctgc gcgctcgctc gctcactgag gccgggcgac caaaggtcgc ccgacgcccg     2280
ggctttgccc gggcggcctc agtgagcgag cgagcgcgcc agctggcgta atagcgaaga     2340
ggcccgcacc gatcgccctt cccaacagtt gcgcagcctg aatggcgaat ggaattccca     2400
gacgattgag cgtcaaaatg taggtatttc catgagcgtt tttcctgttg caatggctgg     2460
cggtaatatt gttctggata ttaccagcaa ggccgatagt ttgagttctt ctactcaggc     2520
aagtgatgtt attactaatc aaagaagtat tgcgacaacg gttaatttgc gtgatggaca     2580
gactctttta ctcggtggcc tcactgatta aaaaacact tctcaggatt ctggcgtacc     2640
gttcctgtct aaaatccctt taatcggcct cctgtttagc tcccgctctg attctaacga     2700
ggaaagcacg ttatacgtgc tcgtcaaagc aaccatagta cgcgccctgt agcggcgcat     2760
taagcgcggc gggtgtggtg gttacgcgca gcgtgaccgc tacacttgcc agcgccctag     2820
cgcccgctcc tttcgctttc ttcccttcct ttctcgccac gttcgccggc tttccccgtc     2880
aagctctaaa tcggggggctc cctttagggt tccgatttag tgctttacgg cacctcgacc     2940
```

```
ccaaaaaact tgattagggt gatggttcac gtagtgggcc atcgccctga tagacggttt    3000
ttcgcccttt gacgttggag tccacgttct ttaatagtgg actcttgttc caaactggaa    3060
caacactcaa ccctatctcg gtctattctt ttgatttata agggattttg ccgatttcgg    3120
cctattggtt aaaaaatgag ctgatttaac aaaaatttaa cgcgaatttt aacaaaatat    3180
taacgtttac aatttaaata tttgcttata caatcttcct gttttggggc ttttctgat     3240 tatcaaccgg ggtacatatg attgacatgc tagttttacg attaccgttc atcgattctc    3300
ttgtttgctc cagactctca ggcaatgacc tgatagcctt tgtagagacc tctcaaaaat    3360
agctaccctc tccggcatga atttatcagc tagaacggtt gaatatcata ttgatggtga    3420
tttgactgtc tccggccttt ctcacccgtt tgaatcttta cctacacatt actcaggcat    3480
tgcatttaaa atatatgagg gttctaaaaa ttttatcct tgcgttgaaa taaaggcttc     3540
tcccgcaaaa gtattacagg gtcataatgt ttttggtaca accgatttag ctttatgctc    3600
tgaggcttta ttgcttaatt ttgctaattc tttgccttgc ctgtatgatt tattggatgt    3660
tggaanttcc tgatgcggta ttttctcctt acgcatctgt gcggtatttc acaccgcata    3720
tggtgcactc tcagtacaat ctgctctgat gccgcatagt taagccagcc ccgacacccg    3780
ccaacacccg ctgacgcgcc ctgacgggct tgtctgctcc cggcatccgc ttacagacaa    3840
gctgtgaccg tctccgggag ctgcatgtgt cagaggtttt caccgtcatc accgaaacgc    3900
gcgagacgaa agggcctcgt gatacgccta tttttatagg ttaatgtcat gataataatg    3960
gtttcttaga cgtcaggtgg cacttttcgg ggaaatgtgc gcggaacccc tatttgttta    4020 ttttctaaa tacattcaaa tatgtatccg ctcatgagac aataaccctg ataaatgctt     4080
caataatatt gaaaaggaa gagtatgagt attcaacatt tccgtgtcgc ccttattccc     4140 tttttgcgg cattttgcct tcctgttttt gctcacccag aaacgctggt gaaagtaaaa     4200
gatgctgaag atcagttggg tgcacgagtg ggttacatcg aactggatct caacagcggt    4260
aagatccttg agagttttcg ccccgaagaa cgttttccaa tgatgagcac ttttaaagtt    4320
ctgctatgtg gcgcggtatt atcccgtatt gacgccgggc aagagcaact cggtcgccgc    4380
atacactatt ctcagaatga cttggttgag tactcaccag tcacagaaaa gcatcttacg    4440
gatggcatga cagtaagaga attatgcagt gctgccataa ccatgagtga taacactgcg    4500
gccaacttac ttctgacaac gatcggagga ccgaaggagc taaccgcttt tttgcacaac    4560 atggggatc atgtaactcg ccttgatcgt tgggaaccgg agctgaatga agccatacca    4620
aacgacgagc gtgacaccac gatgcctgta gcaatggcaa caacgttgcg caaactatta    4680
actggcgaac tacttactct agcttcccgg caacaattaa tagactggat ggaggcggat    4740
aaagttgcag gaccacttct gcgctcggcc cttccggctg gctggtttat tgctgataaa    4800
tctggagccg gtgagcgtgg gtctcgcggt atcattgcag cactggggcc agatggtaag    4860
ccctcccgta tcgtagttat ctacacgacg gggagtcagg caactatgga tgaacgaaat    4920
agacagatcg ctgagatagg tgcctcactg attaagcatt ggtaactgtc agaccaagtt    4980
tactcatata tactttagat tgatttaaaa cttcattttt aatttaaaag gatctaggtg    5040
aagatccttt ttgataatct catgaccaaa atcccttaac gtgagttttc gttccactga    5100
gcgtcagacc ccgtagaaaa gatcaaagga tcttcttgag atcctttttt tctgcgcgta    5160
atctgctgct tgcaaacaaa aaaaccaccg ctaccagcgg tggtttgttt gccggatcaa    5220
gagctaccaa ctctttttcc gaaggtaact ggcttcagca gagcgcagat accaaatact    5280
```

-continued

| | |
|---|---|
| gtccttctag tgtagccgta gttaggccac cacttcaaga actctgtagc accgcctaca | 5340 |
| tacctcgctc tgctaatcct gttaccagtg gctgctgcca gtggcgataa gtcgtgtctt | 5400 |
| accgggttgg actcaagacg atagttaccg gataaggcgc agcggtcggg ctgaacgggg | 5460 |
| ggttcgtgca cacagcccag cttggagcga acgacctaca ccgaactgag atacctacag | 5520 |
| cgtgagctat gagaaagcgc cacgcttccc gaagggagaa aggcggacag gtatccggta | 5580 |
| agcggcaggg tcgaacagg agagcgcacg agggagcttc caggggaaa cgcctggtat | 5640 |
| ctttatagtc ctgtcgggtt tcgccacctc tgacttgagc gtcgattttt gtgatgctcg | 5700 |
| tcaggggggc ggagcctatg gaaaaacgcc agcaacgcgg ccttttacg gttcctggcc | 5760 |
| ttttgctggc cttttgctca catgttcttt cctgcgttat cccctgattc tgtggataac | 5820 |
| cgtattaccg cctttgagtg agctgatacc gctcgccgca gccgaacgac cgagcgcagc | 5880 |
| gagtcagtga gcgaggaagc ggaagagcgc ccaatacgca aaccgcctct ccccgcgcgt | 5940 |
| tggccgattc attaatgcag ctgg | 5964 |

<210> SEQ ID NO 5
<211> LENGTH: 21529
<212> TYPE: DNA
<213> ORGANISM: Artificial Sequence
<220> FEATURE:
<223> OTHER INFORMATION: Synthesized in laboratory
<220> FEATURE:
<221> NAME/KEY: misc_feature
<222> LOCATION: (20778)..(20778)
<223> OTHER INFORMATION: n is a, c, g, or t

<400> SEQUENCE: 5

| | |
|---|---|
| ggatccgaat tcttaattaa catcatcaat aatatacctt attttggatt gaagccaata | 60 |
| tgataatgag ggggtggagt ttgtgacgtg gcgcggggcg tgggaacggg gcgggtgacg | 120 |
| tagtagtgtg gcggaagtgt gatgttgcaa gtgtggcgga acacatgtaa gcgacggatg | 180 |
| tggcaaaagt gacgttttg gtgtgcgccg gtgtacacag gaagtgacaa ttttcgcgcg | 240 |
| gttttaggcg gatgttgtag taaatttggg cgtaaccgag taagatttgg ccattttcgc | 300 |
| gggaaaactg aataagagga agtgaaatct gaataatttt gtgttactca tagcgcgtaa | 360 |
| tatttgtcta gggccgcggg gactttgacc gtttacgtgg agactcgccc aggtgttttt | 420 |
| ctcaggtgtt ttccgcgttc cgggtcaaag ttggcgtttt attattatag tcaggggat | 480 |
| cctctagaac tagtggatct tggccactcc ctctctgcgc gctcgctcgc tcactgaggc | 540 |
| cgcccgggca aagcccgggc gtcgggcgac ctttggtcgc ccggcctcag tgagcgagcg | 600 |
| agcgcgcaga gagggagtgg ccaactccat cactaggggt tccttgtagt taatgattaa | 660 |
| cccgccatgc tacttatcta cgtagccatg gaaactagat aagaaagaaa tacgcagaga | 720 |
| ccaaagttca actgaaacga attaaacggt ttattgatta acaagcaatt acagattacg | 780 |
| agtcaggtat ctggtgccaa tggggcgagg ctctgaatac acgccattag tatccacggt | 840 |
| aagtccacga ttaacagact tgttgtagtt ggaagtgtac tgaatttcgg gattccagcg | 900 |
| tttgctgttt tccttctgca gctcccactc gatctccacg ctgaccgtgt cccgtggagt | 960 |
| actgtgtgat gaaggaagca aactttgccg cactgaaggt ggtcgaagga ttcgcaggta | 1020 |
| ccggggtgtt cttgatgaga atctgtggag gagggtgttt aagtccgaat ccacccatga | 1080 |
| ggggagaggg gtgaaaatgt ccgtccgtgt gtggaatctt tgcccagatg ggcccctgaa | 1140 |
| ggtacacatc tctgtcctgc cagaccatgc ctggaagaac gccttgtgtg ttgacatctg | 1200 |
| cggtagctgc ttgtctgttg cctctctgga ggttggtaga tacagaacca tactgctccg | 1260 |

```
tagccacggg attggttgtt ccgatttcct cttcgtctgt aatcatgacc ttttcaatgt   1320
tcacatttgt tttctctgag ccttgcttcc caaagatgag aacccccgctc tgaggaaaaa   1380 acttttcttc atcgtccttg tggcttgcca tggccggatt caccagagag tctctgccat   1440
tgaggtggta cttggtagct ccagtccacg agtattcact gttgttgtta ccgcagatg    1500 tctttgatac tcgctgctgg cggtaacagg gtccaggaag ccagttccta gactggtccc   1560
gaatgtcact cgctccggcc tgagaaaact gaagccttga ctgcgtggtg gttccacttg   1620
gagtgtttgt tctgctcaag taatacaggt actggtcgat gagaggattc atgagacggt   1680
ccagactctg gctgtgagcg tagctgctgt ggaaaggaac gtcctcaaaa gtgtagctga   1740
aggtaaagtt gtttccggta cgcagcatct gagaaggaaa gtactccagg cagtaaaatg   1800
aagagcgtcc tactgcctga ctcccgttgt tcagggtgag gtatccatac tgtggcacca   1860
tgaagacgtc tgctgggaac ggcgggaggc atccttgatg cgccgagccg aggacgtacg   1920
ggagctggta ctccgagtca gtaaacacct gaaccgtgct ggtaaggtta ttggcaatcg   1980
tcgtcgtacc gtcattctgc gtgacctctt tgacttgaat gttaaagagc ttgaagttga   2040
gtctcttggg tcggaatccc cagttgttgt tgatgagtct ttgccagtca cgtggtgaaa   2100
agtggcagtg gaatctgttg aagtcaaaat accccccaagg ggtgctgtag ccaaagtagt   2160
gattgtcgtt cgaggctcct gattggctgg aaatttgttt gtagaggtgg ttgttgtagg   2220
tgggcagggc ccaggttcgg gtgctggtgg tgatgactct gtcgcccatc catgtggaat   2280
cgcaatgcca atttccggag gaattaccca ctccgtcggc ccctcgtta ttgtctgcca    2340 ttggtgcgcc actgcctgta gccatcgtat tagttcccag accagagggg gctgctggtg   2400
gctgtccgag aggctggggg tcaggtactg agtctgcgtc tccagtctga ccaaaattca   2460 atcttttttct tgcaggctgc tggcccgcct ttccggttcc cgaggaggag tctggctcca   2520
caggagagtg ctctaccggc ctctttttc ccggagccgt cttaacaggt tcctcaacca    2580
ggcccagagg ttcaagaacc ctcttttttcg cctggaagac tgctcgtccg aggttgcccc   2640
caaaagacgt atcttcttta aggcgctcct gaaactccgc gtcggcgtgg ttgtacttga   2700
ggtacgggtt gtctccgctg tcgagctgcc ggtcgtaggc tttgtacgtg ctcgagggcc   2760
gcggcgtctg cctcgttgac cggctctccc ttgtcgagtc cgttgaaggg tccgaggtac   2820
ttgtacccag gaagcacaag acccctgctg tcgtccttat gccgctctgc gggctttggt   2880
ggtggtgggc caggtttgag cttccaccac tgtcttattc cttcagagag agtgtcctcg   2940
agccaatctg gaagataacc atcggcagcc atacctgatt taaatcattt attgttcaaa   3000
gatgcagtca tccaaatcca cattgaccag atcgcaggca gtgcaagcgt ctggcacctt   3060
tcccatgata tgatgaatgt agcacagttt ctgatacgcc tttttgacga cagaaacggg   3120
ttgagattct gacacgggaa agcactctaa acagtctttc tgtccgtgag tgaagcagat   3180
atttgaattc tgattcattc tctcgcattg tctgcaggga acagcatca gattcatgcc     3240 cacgtgacga gaacatttgt tttggtacct gtctgcgtag ttgatcgaag cttccgcgtc   3300
tgacgtcgat ggctgcgcaa ctgactcgcg cacccgtttg ggctcactta tatctgcgtc   3360 actggggggcg ggtcttttct tggctccacc ctttttgacg tagaattcat gctccacctc   3420
aaccacgtga tcctttgccc accggaaaaa gtctttgact tcctgcttgg tgaccttccc   3480
aaagtcatga tccagacggc gggtgagttc aaatttgaac atccggtctt gcaacggctg   3540
ctggtgttcg aaggtcgttg agttcccgtc aatcacggcg cacatgttgg tgttggaggt   3600
```

```
gacgatcacg ggagtcgggt ctatctgggc cgaggacttg catttctggt ccacgcgcac    3660
cttgcttcct ccgagaatgg cttttggccga ctccacgacc ttggcggtca tcttcccctc    3720
ctcccaccag atcaccatct tgtcgacaca gtcgttgaag ggaaagttct cattggtcca    3780
gtttacgcac ccgtagaagg gcacagtgtg ggctatggcc tccgcgatgt tggtcttccc    3840
ggtagttgca ggcccaaaca gccagatggt gttcctcttg ccgaactttt tcgtggccca    3900
tcccagaaag acggaagccg catattgggg atcgtacccg tttagttcca aaattttata    3960
aatccgattg ctggaaatgt cctccacggg ctgctggccc accaggtagt cgggggcggt    4020
tttagtcagg ctcataatct ttcccgcatt gtccaaggca gccttgattt gggaccgcga    4080
gttggaggcc gcattgaagg agatgtatga ggcctggtcc tcctggatcc actgcttctc    4140
cgaggtaatc cccttgtcca cgagccaccc gaccagctcc atgtacctgg ctgaagtttt    4200
tgatctgatc accggcgcat cagaattggg attctgattc tctttgttct gctcctgcgt    4260
ctgcgcacg tgcgtcagat gctgcgccac caaccgttta cgctccgtga gattcaaaca    4320
ggcgcttaaa tactgttcca tattagtcca cgcccactgg agctcaggct gggttttggg    4380
gagcaagtaa ttggggatgt agcactcatc caccaccttg ttcccgcctc cggcgccatt    4440
tctggtcttt gtgaccgcga accagtttgg caaagtcggc tcgatcccgc ggtaaattct    4500
ctgaatcagt ttttcgcgaa tctgactcag gaaacgtccc aaaaccatgg atttcacccc    4560
ggtggtttcc acgagcacgt gcatgtggaa gtagctctct cccttctcaa attgcacaaa    4620
gaaaagggcc tccggggcct tactcacacg gcgccattcc gtcagaaagt cgcgctgcag    4680
cttctcggcc acgtcaggg gtgcctgctc aatcagattc agatccatgt cagaatctgg    4740
cggcaactcc cattccttct cggccaccca gttcacaaag ctgtcagaaa tgccgggcag    4800
atgcccgtca aggtcgctgg ggaccttaat cacaatctcg taaaacccg gcatggcggc    4860
tgcgcgttca aacctcccgc ttcaaaatgg agaccctgcg tgctcactcg ggcttaaata    4920
cccagcgtga ccacatggtg tcgcaaaatg tcgcaaaaca ctcacgtgac ctctaataca    4980
ggacctccct aaccctatga cgtaattcac gtcacgactc caccctcca ggaaccccta    5040
gtgatggagt tggccactcc ctctctgcgc gctcgctcgc tcactgaggc cgcccgggca    5100
aagcccgggc gtcgggcgac ctttggtcgc ccggcctcag tgagcgagcg agcgcgcaga    5160
gagggagtgg ccaagatccc ccgggctgca ggaattcgat atcaagctta tcgatgcatg    5220
tccttgggtc cggcctgctg aatgcgcagg cggtcggcca tgcccaggc ttcgttttga    5280
catcggcgca ggtctttgta gtagtcttgc atgagccttt ctaccggcac ttcttcttct    5340
ccttcctctt gtcctgcatc tcttgcatct atcgctgcgg cggcggcgga gtttggccgt    5400
aggtggcgcc ctcttcctcc catgcgtgtg accccgaagc ccctcatcgg ctgaagcagg    5460
gctaggtcgg cgacaacgcg ctcggctaat atggcctgct gcacctgcgt gagggtagac    5520
tggaagtcat ccatgtccac aaagcggtgg tatgcgcccg tgttgatggt gtaagtgcag    5580
ttggccataa cggaccagtt aacggtctgg tgacccggct gcgagagctc ggtgtacctg    5640
agacgcgagt aagccctcga gtcaaatacg tagtcgttgc aagtccgcac caggtactgg    5700
tatcccacca aaagtgcgg cggcggctgg cggtagaggg gccagcgtag ggtggccggg    5760
gctccggggg cgagatcttc caacataagg cgatgatatc cgtagatgta cctggacatc    5820
caggtgatgc cggcggcggt ggtggaggcg cgcggaaagt cgcggacgcg gttccagatg    5880
ttgcgcagcg gcaaaagtg ctccatggtc gggacgctct ggccggtcag gcgcgcgcaa    5940
tcgttgacgc tctagaccgt gcaaaaggag agcctgtaag cgggcactct tccgtggtct    6000
```

```
ggtggataaa ttcgcaaggg tatcatggcg gacgaccggg gttcgagccc cgtatccggc    6060
cgtccgccgt gatccatgcg gttaccgccc gcgtgtcgaa cccaggtgtg cgacgtcaga    6120
caacggggga gtgctccttt tggcttcctt ccaggcgcgg cggctgctgc gctagctttt    6180
ttggccactg gccgcgcgca gcgtaagcgg ttaggctgga aagcgaaagc attaagtggc    6240
tcgctccctg tagccggagg gttatttttcc aagggttgag tcgcgggacc cccggttcga    6300
gtctcggacc ggccggactg cggcgaacgg gggtttgcct ccccgtcatg caagaccccg    6360
cttgcaaatt cctccggaaa cagggacgag ccccttttttt gcttttccca gatgcatccg    6420
gtgctgcggc agatgcgccc ccctcctcag cagcggcaag agcaagagca gcggcagaca    6480
tgcagggcac cctcccctcc tcctaccgcg tcaggagggg cgacatccgc ggttgacgcg    6540
gcagcagatg tgattacga acccccgcgg cgccgggccc ggcactacct ggacttggag    6600
gagggcgagg gcctggcgcg gctaggagcg ccctctcctg agcggtaccc aagggtgcag    6660
ctgaagcgtg atacgcgtga ggcgtacgtg ccgcggcaga acctgtttcg cgaccgcgag    6720
ggagaggagc ccgaggagat gcgggatcga aagttccacg cagggcgcga gctgcggcat    6780
ggcctgaatc gcgagcggtt gctgcgcgag gaggactttg agcccgacgc gcgaaccggg    6840
attagtcccg cgcgcgcaca cgtggcggcc gccgacctgg taaccgcata cgagcagacg    6900
gtgaaccagg gcgatcgcac cctttggcgc atcccattct ccagtaactt tatgtccatg    6960
ggcgcactca cagacctggg ccaaaaacctt ctctacgcca actccgccca cgcgctagac    7020
atgacttttg aggtggatcc catggacgag cccacccttc tttatgtttt gtttgaagtc    7080
tttgacgtgg tccgtgtgca ccggccgcac cgcggcgtca tcgaaaccgt gtacctgcgc    7140
acgcccttct cggccggcaa cgccacaaca taaagaagca agcaacatca acaacagctg    7200
ccgccatggg ctccagtgag caggaactga agccattgt caaagatctt ggttgtgggc    7260
catatttttt gggcacctat gacaagcgct ttccaggctt tgtttctcca cacaagctcg    7320
cctgcgccat agtcaatacg gccggtcgcg agactggggg cgtacactgg atggcctttg    7380
cctggaaccc gcactcaaaa acatgctacc tctttgagcc ctttggcttt tctgaccagc    7440
gactcaagca ggtttaccag tttgagtacg agtcactcct gcgccgtagc gccattgctt    7500
cttcccccga ccgctgtata acgctggaaa agtccaccca aagcgtacag gggcccaact    7560
cggccgcctg tggactattc tgctgcatgt ttctccacgc ctttgccaac tggccccaaa    7620
ctcccatgga tcacaacccc accatgaacc ttattaccgg ggtacccaac tccatgctca    7680
acagtcccca ggtacagccc accctgcgtc gcaaccagga acagtctcta gcttcctgg    7740 agcgccactc gccctacttc cgcagccaca gtgcgcagat taggagcgcc acttctttttt    7800 gtcacttgaa aaacatgtaa aaataatgta ctagagacac tttcaataaa ggcaaatgct    7860
tttatttgta cactctcggg tgattattta ccccccaccct tgccgtctgc gccgtttaaa    7920
aatcaaaggg gttctgccgc gcatcgctat gcgccactgg cagggacacg ttgcgatact    7980
ggtgtttagt gctccactta aactcaggca caaccatccg cggcagctcg gtgaagtttt    8040
cactccacag gctgcgcacc atcaccaacg cgtttagcag gtcgggcgcc gatatcttga    8100
agtcgcagtt ggggcctccg ccctgcgcgc gcgagttgcg atacacaggg ttgcagcact    8160
ggaacactat cagcgccggg tggtgcacgc tggccagcac gctcttgtcg gagatcagat    8220
ccgcgtccag gtcctccgcg ttgctcaggg cgaacggagt caactttggt agctgccttc    8280
ccaaaaaggg cgcgtgccca ggctttgagt tgcactcgca ccgtagtggc atcaaaaggt    8340
```

```
gaccgtgccc ggtctgggcg ttaggataca gcgcctgcat aaaagccttg atctgcttaa    8400
aagccacctg agccttttgcg ccttcagaga agaacatgcc gcaagacttg ccggaaaact    8460
gattggccgg acaggccgcg tcgtgcacgc agcaccttgc gtcggtgttg gagatctgca    8520
ccacatttcg gccccaccgg ttcttcacga tcttggcctt gctagactgc tccttcagcg    8580
cgcgctgccc gttttcgctc gtcacatcca tttcaatcac gtgctcctta tttatcataa    8640
tgcttccgtg tagacactta agctcgcctt cgatctcagc gcagcggtgc agccacaacg    8700
cgcagcccgt gggctcgtga tgcttgtagg tcacctctgc aaacgactgc aggtacgcct    8760
gcaggaatcg ccccatcatc gtcacaaagg tcttgttgct ggtgaaggtc agctgcaacc    8820
cgcggtgctc ctcgttcagc caggtcttgc atacggccgc cagagcttcc acttggtcag    8880
gcagtagttt gaagttcgcc tttagatcgt tatccacgtg gtacttgtcc atcagcgcgc    8940
gcgcagcctc catgcccttc tcccacgcag acacgatcgg cacactcagc gggttcatca    9000
ccgtaatttc actttccgct tcgctgggct cttcctcttc ctcttgcgtc cgcataccac    9060
gcgccactgg gtcgtcttca ttcagccgcc gcactgtgcg cttacctcct ttgccatgct    9120
tgattagcac cggtgggttg ctgaaaccca ccatttgtag cgccacatct tctctttctt    9180
cctcgctgtc cacgattacc tctggtgatg gcgggcgctc gggcttggga aagggcgct    9240
tcttttctt cttgggcgca atggccaaat ccgccgccga ggtcgatggc cgcgggctgg    9300
gtgtgcgcgg caccagcgcg tcttgtgatg agtcttcctc gtcctcggac tcgatacgcc    9360
gcctcatccg ctttttggg ggcgcccggg gaggcggcgg cgacggggac ggggacgaca    9420
cgtcctccat ggttggggga cgtcgcgccg caccgcgtcc gcgctcgggg gtggtttcgc    9480
gctgctcctc ttcccgactg gccatttcct tctcctatag gcagaaaaag atcatggagt    9540
cagtcgagaa gaaggacagc ctaaccgccc cctctgagtt cgccaccacc gcctccaccg    9600
atgccgccaa cgcgcctacc accttccccg tcgaggcacc cccgcttgag gaggaggaag    9660
tgattatcga gcaggaccca ggttttgtaa gcgaagacga cgaggaccgc tcagtaccaa    9720
cagaggataa aaagcaagac caggacaacg cagaggcaaa cgaggaacaa gtcgggcggg    9780
gggacgaaag gcatggcgac tacctagatg tgggagacga cgtgctgttg aagcatctgc    9840
agcgccagtg cgccattatc tgcgacgcgt tgcaagagcg cagcgatgtg cccctcgcca    9900
tagcggatgt cagccttgcc tacgaacgcc acctattctc accgcgcgta ccccccaaac    9960
gccaagaaaa cggcacatgc gagcccaacc cgcgcctcaa cttctacccc gtatttgccg    10020
tgccagaggt gcttgccacc tatcacatct ttttccaaaa ctgcaagata cccctatcct    10080
gccgtgccaa ccgcagccga gcggacaagc agctggcctt gcggcagggc gctgtcatac    10140
ctgatatcgc ctcgctcaac gaagtgccaa aaatctttga gggtcttgga cgcgacgaga    10200
agcgcgcggc aaacgctctg caacaggaaa acagcgaaaa tgaaagtcac tctggagtgt    10260
tggtggaact cgagggtgac aacgcgcgcc tagccgtact aaaacgcagc atcgaggtca    10320
cccactttgc ctacccggca cttaacctac ccccaaggt catgagcaca gtcatgagtg    10380
agctgatcgt gcgccgtgcg cagcccctgg agagggatgc aaatttgcaa gaacaaacag    10440
aggagggcct acccgcagtt ggcgacgagc agctagcgcg ctggcttcaa acgcgcgagc    10500
ctgccgactt ggaggagcga cgcaaactaa tgatggccgc agtgctcgtt accgtggagc    10560
ttgagtgcat gcagcggttc tttgctgacc cggagatgca gcgcaagcta gaggaaacat    10620
tgcactacac ctttcgacag ggctacgtac gccaggcctg caagatctcc aacgtggagc    10680
tctgcaacct ggtctcctac cttggaattt tgcacgaaaa ccgccttggg caaaacgtgc    10740
```

```
ttcattccac gctcaagggc gaggcgcgcc gcgactacgt ccgcgactgc gtttacttat   10800
ttctatgcta cacctggcag acggccatgg gcgtttggca gcagtgcttg gaggagtgca   10860
acctcaagga gctgcagaaa ctgctaaagc aaaacttgaa ggacctatgg acggccttca   10920
acgagcgctc cgtggccgcg cacctggcgg acatcatttt ccccgaacgc ctgcttaaaa   10980
ccctgcaaca gggtctgcca gacttcacca gtcaaagcat gttgcagaac tttaggaact   11040
ttatcctaga gcgctcagga atcttgcccg ccacctgctg tgcacttcct agcgactttg   11100
tgcccattaa gtaccgcgaa tgccctccgc cgctttgggg ccactgctac cttctgcagc   11160
tagccaacta ccttgcctac cactctgaca taatggaaga cgtgagcggt gacggtctac   11220
tggagtgtca ctgtcgctgc aacctatgca ccccgcaccg ctccctggtt tgcaattcgc   11280
agctgcttaa cgaaagtcaa attatcggta ccttttgagct gcagggtccc tcgcctgacg   11340
aaaagtccgc ggctccgggg ttgaaactca ctccggggct gtggacgtcg gcttaccttc   11400
gcaaatttgt acctgaggac taccacgccc acgagattag gttctacgaa gaccaatccc   11460
gcccgccaaa tgcggagctt accgcctgcg tcattaccca gggccacatt cttggccaat   11520
tgcaagccat caacaaagcc cgccaagagt ttctgctacg aaagggacgg ggggtttact   11580
tggaccccca gtccggcgag gagctcaacc caatcccccc gccgccgcag ccctatcagc   11640
agcagccgcg ggcccttgct tcccaggatg gcacccaaaa agaagctgca gctgccgccg   11700
ccacccacgg acgaggagga atactgggac agtcaggcag aggaggtttt ggacgaggag   11760
gaggaggaca tgatggaaga ctgggagagc ctagacgagg aagcttccga ggtcgaagag   11820
gtgtcagacg aaacaccgtc accctcggtc gcattcccct cgccggcgcc ccagaaatcg   11880
gcaaccggtt ccagcatggc tacaacctcc gctcctcagg cgccgccggc actgcccgtt   11940
cgccgaccca accgtagatg ggacaccact ggaaccaggg ccggtaagtc caagcagccg   12000
ccgccgttag cccaagagca acaacagcgc caaggctacc gctcatggcg cgggcacaag   12060
aacgccatag ttgcttgctt gcaagactgt gggggcaaca tctccttcgc ccgccgcttt   12120
cttctctacc atcacggcgt ggccttcccc cgtaacatcc tgcattacta ccgtcatctc   12180
tacagcccat actgcaccgg cggcagcggc agcggcagca acagcagcgg ccacacagaa   12240
gcaaaggcga ccggatagca agactctgac aaagcccaag aaatccacag cggcggcagc   12300
agcaggagga ggagcgctgc gtctggcgcc caacgaaccc gtatcgaccc gcgagcttag   12360
aaacaggatt tttcccactc tgtatgctat atttcaacag agcaggggcc aagaacaaga   12420
gctgaaaata aaaaacaggt ctctgcgatc cctcacccgc agctgcctgt atcacaaaag   12480
cgaagatcag cttcggcgca cgctggaaga gcgcggaggct ctcttcagta aatactgcgc   12540
gctgactctt aaggactagt ttcgcgccct ttctcaaatt taagcgcgaa aactacgtca   12600
tctccagcgg ccacacccgg cgccagcacc tgtcgtcagc gccattatga gcaaggaaat   12660
tcccacgccc tacatgtgga gttaccagcc acaaatggga cttgcggctg gagctgccca   12720
agactactca acccgaataa actacatgag cgcgggaccc cacatgatat cccgggtcaa   12780
cggaatccgc gcccaccgaa accgaattct cttggaacag gcggctatta ccaccacacc   12840
tcgtaataac cttaatcccc gtagttggcc cgctgccctg gtgtaccagg aaagtcccgc   12900
tcccaccact gtggtacttc ccagagacgc ccaggccgaa gttcagatga ctaactcagg   12960
ggcgcagctt gcgggcggct ttcgtcacag ggtgcggtcg cccgggcagg gtataactca   13020
cctgacaatc agagggcgag gtattcagct caacgacgag tcggtgagct cctcgcttgg   13080
```

```
tctccgtccg gacgggacat ttcagatcgg cggcgccggc cgctcttcat tcacgcctcg   13140
tcaggcaatc ctaactctgc agacctcgtc ctctgagccg cgctctggag gcattggaac   13200
tctgcaattt attgaggagt ttgtgccatc ggtctacttt aaccccttct cgggacctcc   13260
cggccactat ccggatcaat ttattcctaa ctttgacgcg gtaaaggact cggcggatgg   13320
ctacgactga atgttaagtg gagaggcaga gcaactgcgc ctgaaacacc tggtccactg   13380
tcgccgccac aagtgctttg cccgcgactc cggtgagttt tgctactttg aattgcccga   13440
ggatcatatc gagggcccgg cgcacggcgt ccggcttacc gcccagggag agcttgcccg   13500
tagcctgatt cgggagttta cccagcgccc cctgctagtt gagcgggaca ggggaccctg   13560
tgttctcact gtgatttgca actgtcctaa ccctggatta catcaagatc tttgttgcca   13620
tctctgtgct gagtataata aatacagaaa ttaaaatata ctggggctcc tatcgccatc   13680
ctgtaaacgc caccgtcttc acccgcccaa gcaaaccaag gcgaacctta cctggtactt   13740
ttaacatctc tccctctgtg atttacaaca gtttcaaccc agacggagtg agtctacgag   13800
agaacctctc cgagctcagc tactccatca gaaaaaacac caccctcctt acctgccggg   13860
aacgtacgag tgcgtcaccg gccgctgcac cacacctacc gcctgaccgt aaaccagact   13920
ttttccggac agacctcaat aactctgttt accagaacag gaggtgagct tagaaaaccc   13980
ttagggtatt aggccaaagg cgcagctact gtggggttta tgaacaattc aagcaactct   14040
acgggctatt ctaattcagg tttctctaga aatggacgga attattacag agcagcgcct   14100
gctagaaaga cgcagggcag cggccgagca acagcgcatg aatcaagagc tccaagacat   14160
ggttaacttg caccagtgca aaaggggtat cttttgtctg gtaaagcagg ccaaagtcac   14220
ctacgacagt aataccaccg gacaccgcct tagctacaag ttgccaacca agcgtcagaa   14280
attggtggtc atggtgggag aaaagcccat taccataact cagcactcgg tagaaaccga   14340
aggctgcatt cactcacctt gtcaaggacc tgaggatctc tgcacccttc ttaagaccct   14400
gtgcggtctc aaagatctta ttccctttaa ctaataaaaa aaaataataa agcatcactt   14460
acttaaaatc agttagcaaa tttctgtcca gtttattcag cagcacctcc ttgccctcct   14520
cccagctctg gtattgcagc ttcctcctgg ctgcaaactt tctccacaat ctaaatggaa   14580
tgtcagtttc ctcctgttcc tgtccatccg cacccactat cttcatgttg ttgcagatga   14640
agcgcgcaag accgtctgaa gatacctcca acccgtgta tccatatgac acggaaaccg   14700
gtcctccaac tgtgcctttt cttactcctc cctttgtatc ccccaatggg tttcaagaga   14760 gtcccctgg ggtactctct ttgcgcctat ccgaacctct agttacctcc aatggcatgc   14820
ttgcgctcaa aatgggcaac ggcctctctc tggacgaggc cggcaacctt acctcccaaa   14880
atgtaaccac tgtgagccca cctctcaaaa aaaccaagtc aaacataaac ctggaaatat   14940
ctgcacccct cacagttacc tcagaagccc taactgtggc tgccgccgca cctctaatgg   15000
tcgcgggcaa cacactcacc atgcaatcac aggcccgct aaccgtgcac gactccaaac   15060
ttagcattgc cacccaagga cccctcacag tgtcagaagg aaagctagcc ctgcaaacat   15120
caggccccct caccaccacc gatagcagta cccttactat cactgcctca cccctctaa   15180 ctactgccac tggtagcttg ggcattgact tgaaagagcc catttataca caaatggaa   15240 aactaggact aaagtacggg gctcctttgc atgtaacaga cgacctaaac actttgaccg   15300
tagcaactgg tccaggtgtg actattaata atacttcctt gcaaactaaa gttactggag   15360
ccttgggttt tgattcacaa ggcaatatgc aacttaatgt agcaggagga ctaaggattg   15420
attctcaaaa cagacgcctt atacttgatg ttagttatcc gtttgatgct caaaaccaac   15480
```

```
taaatctaag actaggacag ggccctcttt ttataaactc agcccacaac ttggatatta   15540
actacaacaa aggcctttac ttgtttacag cttcaaacaa ttccaaaaag cttgaggtta   15600
acctaagcac tgccaagggg ttgatgtttg acgctacagc catagccatt aatgcaggag   15660
atgggcttga atttggttca cctaatgcac caaacacaaa tccccctcaaa acaaaaattg  15720
gccatggcct agaatttgat tcaaacaagg ctatggttcc taaactagga actggcctta   15780
gttttgacag cacaggtgcc attacagtag gaaacaaaaa taatgataag ctaactttgt   15840
ggaccacacc agctccatct cctaactgta gactaaatgc agagaaagat gctaaactca   15900
cttggtctt aacaaaatgt ggcagtcaaa tacttgctac agtttcagtt ttggctgtta    15960
aaggcagttt ggctccaata tctggaacag ttcaaagtgc tcatcttatt ataagatttg   16020
acgaaaatgg agtgctacta aacaattcct tcctggaccc agaatattgg aactttagaa   16080
atggagatct tactgaaggc acagcctata caaacgctgt tggatttatg cctaacctat   16140
cagcttatcc aaaatctcac ggtaaaactg ccaaaagtaa cattgtcagt caagtttact   16200
taaacggaga caaaactaaa cctgtaacac taaccattac actaaacggt acacaggaaa   16260
caggagacac aactccaagt gcatactcta tgtcattttc atgggactgg tctggccaca   16320
actacattaa tgaaatattt gccacatcct cttacacttt ttcatacatt gcccaagaat   16380
aaagaatcgt tgtgttatg tttcaacgtg tttattttc aattgcagaa aatttcaagt     16440
cattttcat tcagtagtat agccccacca ccacatagct tatacagatc accgtacctt    16500
aatcaaactc acagaaccct agtattcaac ctgccacctc cctcccaaca cacagagtac   16560
acagtccttt ctccccggct ggccttaaaa agcatcatat catgggtaac agacatattc   16620
ttaggtgtta tattccacac ggtttcctgt cgagccaaac gctcatcagt gatattaata   16680
aactccccgg gcagctcact taagttcatg tcgctgtcca gctgctgagc cacaggctgc   16740
tgtccaactt gcggttgctt aacgggcggc gaaggagaag tccacgccta catgggggta   16800
gagtcataat cgtgcatcag gatagggcgg tggtgctgca gcagcgcgcg aataaactgc   16860
tgccgccgcc gctccgtcct gcaggaatac aacatggcag tggtctcctc agcgatgatt   16920
cgcaccgccc gcagcataag gcgccttgtc ctccgggcac agcagcgcac cctgatctca   16980
cttaaatcag cacagtaact gcagcacagc accacaatat tgttcaaaat cccacagtgc   17040
aaggcgctgt atccaaagct catggcgggg accacagaac ccacgtggcc atcataccac   17100
aagcgcaggt agattaagtg gcgacccctc ataaacacgc tggacataaa cattacctct   17160
tttggcatgt tgtaattcac cacctcccgg taccatataa acctctgatt aaacatggcg   17220
ccatccacca ccatcctaaa ccagctggcc aaaacctgcc cgccggctat acactgcagg   17280
gaaccgggac tggaacaatg acagtggaga gcccaggact cgtaaccatg gatcatcatg   17340
ctcgtcatga tatcaatgtt ggcacaacac aggcacacgt gcatacactt cctcaggatt   17400
acaagctcct cccgcgttag aaccatatcc caggaacaa cccattcctg aatcagcgta    17460
aatcccacac tgcagggaag acctcgcacg taactcacgt tgtgcattgt caaagtgtta   17520
cattcgggca gcagcggatg atcctccagt atggtagcgc gggtttctgt ctcaaaagga   17580
ggtagacgat ccctactgta cggagtgcgc cgagacaacc gagatcgtgt tggtcgtagt   17640
gtcatgccaa atggaacgcc ggacgtagtc atatttcctg aagcaaaacc aggtgcgggc   17700
gtgacaaaca gatctgcgtc tccggtctcg ccgcttagat cgctctgtgt agtagttgta   17760
gtatatccac tctctcaaag catccaggcg ccccctggct tcgggttcta tgtaaactcc   17820
```

```
ttcatgcgcc gctgccctga taacatccac caccgcagaa taagccacac ccagccaacc   17880
tacacattcg ttctgcgagt cacacacggg aggagcggga agagctggaa gaaccatgtt   17940
tttttttta ttccaaaaga ttatccaaaa cctcaaaatg aagatctatt aagtgaacgc   18000
gctcccctcc ggtggcgtgg tcaaactcta cagccaaaga acagataatg gcatttgtaa   18060
gatgttgcac aatggcttcc aaaaggcaaa cggccctcac gtccaagtgg acgtaaaggc   18120
taaacccttc agggtgaatc tcctctataa acattccagc accttcaacc atgcccaaat   18180
aattctcatc tcgccacctt ctcaatatat ctctaagcaa atcccgaata ttaagtccgg   18240
ccattgtaaa aatctgctcc agagcgccct ccaccttcag cctcaagcag cgaatcatga   18300
ttgcaaaaat tcaggttcct cacagacctg tataagattc aaaagcggaa cattaacaaa   18360
aataccgcga tcccgtaggt cccttcgcag ggccagctga acataatcgt gcaggtctgc   18420
acggaccagc gcggccactt ccccgccagg aaccatgaca aaagaaccca cactgattat   18480
gacacgcata ctcggagcta tgctaaccag cgtagccccg atgtaagctt gttgcatggg   18540
cggcgatata aaatgcaagg tgctgctcaa aaaatcaggc aaagcctcgc gcaaaaaaga   18600
aagcacatcg tagtcatgct catgcagata aaggcaggta agctccggaa ccaccacaga   18660
aaaagacacc attttctct caaacatgtc tgcgggtttc tgcataaaca caaaataaaa   18720
taacaaaaaa acatttaaac attagaagcc tgtcttacaa caggaaaaac aacccttata   18780
agcataagac ggactacggc catgccggcg tgaccgtaaa aaaactggtc accgtgatta   18840
aaaagcacca ccgacagctc ctcggtcatg tccggagtca taatgtaaga ctcggtaaac   18900
acatcaggtt gattcacatc ggtcagtgct aaaaagcgac cgaaatagcc cgggggaata   18960
catcccgca ggcgtagaga caacattaca gcccccatag gaggtataac aaaattaata   19020
ggagagaaaa acacataaac acctgaaaaa ccctcctgcc taggcaaaat agcaccctcc   19080
cgctccagaa caacatacag cgcttccaca gcggcagcca taacagtcag ccttaccagt   19140
aaaaaagaaa acctattaaa aaaacaccac tcgacacggc accagctcaa tcagtcacag   19200
tgtaaaaaag ggccaagtgc agagcgagta tatataggac taaaaaatga cgtaacggtt   19260
aaagtccaca aaaaacaccc agaaaaccgc acgcgaacct acgcccagaa acgaaagcca   19320
aaaaacccac aacttcctca aatcgtcact tccgttttcc cacgttacgt cacttcccat   19380
tttaagaaaa ctacaattcc caacacatac aagttactcc gccctaaaac ctacgtcacc   19440
cgccccgttc ccacgccccg cgccacgtca caaactccac cccctcatta tcatattggc   19500
ttcaatccaa ataaggtat attattgatg atgttaatta agaattcgga tctgcgacgc   19560
gaggctggat ggccttcccc attatgattc ttctcgcttc cggcggcatc gggatgcccg   19620
cgttgcaggc catgctgtcc aggcaggtag atgacgacca tcaggacag cttcacggcc   19680
agcaaaaggc caggaaccgt aaaaaggccg cgttgctggc gttttttccat aggctccgcc   19740
cccctgacga gcatcacaaa aatcgacgct caagtcagag gtggcgaaac ccgacaggac   19800
tataaagata ccaggcgttt ccccctggaa gctccctcgt gcgctctcct gttccgaccc   19860
tgccgcttac cggatacctg tccgcctttc tcccttcggg aagcgtggcg ctttctcaat   19920
gctcacgctg taggtatctc agttcggtgt aggtcgttcg ctccaagctg ggctgtgtgc   19980
acgaacccc cgttcagccc gaccgctgcg ccttatccgg taactatcgt cttgagtcca   20040
acccggtaag acacgactta tcgccactgg cagcagccac tggtaacagg attagcagag   20100
cgaggtatgt aggcggtgct acagagttct tgaagtggtg gcctaactac ggctacacta   20160
gaaggacagt atttggtatc tgcgctctgc tgaagccagt taccttcgga aaaagagttg   20220
```

```
gtagctcttg atccggcaaa caaaccaccg ctggtagcgg tggttttttt gtttgcaagc    20280
agcagattac gcgcagaaaa aaaggatctc aagaagatcc tttgatcttt tctacggggt    20340
ctgacgctca gtggaacgaa aactcacgtt aagggatttt ggtcatgaga ttatcaaaaa    20400
ggatcttcac ctagatcctt ttaaatcaat ctaaagtata tatgagtaaa cttggtctga    20460
cagttaccaa tgcttaatca gtgaggcacc tatctcagcg atctgtctat ttcgttcatc    20520
catagttgcc tgactccccg tcgtgtagat aactacgata cgggagggct taccatctgg    20580
ccccagtgct gcaatgatac cgcgagaccc acgctcaccg gctccagatt tatcagcaat    20640
aaaccagcca gccggaaggg ccgagcgcag aagtggtcct gcaactttat ccgcctccat    20700
ccagtctatt aattgttgcc gggaagctag agtaagtagt tcgccagtta atagtttgcg    20760
caacgttgtt gccattgntg caggcatcgt ggtgtcacgc tcgtcgtttg gtatggcttc    20820
attcagctcc ggttcccaac gatcaaggcg agttacatga tcccccatgt tgtgcaaaaa    20880
agcggttagc tccttcggtc ctccgatcgt tgtcagaagt aagttggccg cagtgttatc    20940
actcatggtt atggcagcac tgcataattc tcttactgtc atgccatccg taagatgctt    21000
ttctgtgact ggtgagtact caaccaagtc attctgagaa tagtgtatgc ggcgaccgag    21060
ttgctcttgc ccggcgtcaa cacgggataa taccgcgcca catagcagaa ctttaaaagt    21120
gctcatcatt ggaaaacgtt cttcggggcg aaaactctca aggatcttac cgctgttgag    21180
atccagttcg atgtaaccca ctcgtgcacc caactgatct tcagcatctt ttactttcac    21240
cagcgtttct gggtgagcaa aaacaggaag gcaaaatgcc gcaaaaaagg gaataagggc    21300
gacacggaaa tgttgaatac tcatactctt ccttttcaa tattattgaa gcatttatca    21360
gggttattgt ctcatgagcg gatacatatt tgaatgtatt tagaaaaata aacaaatagg    21420
ggttccgcgc acatttcccc gaaaagtgcc acctgacgtc taagaaacca ttattatcat    21480
gacattaacc tataaaaata ggcgtatcac gaggcccttt cgtcttcaa               21529
```

<210> SEQ ID NO 6
<211> LENGTH: 5824
<212> TYPE: DNA
<213> ORGANISM: Artificial Sequence
<220> FEATURE:
<223> OTHER INFORMATION: Synthesized in laboratory

<400> SEQUENCE: 6

```
ggatcccctg aggggggcccc catgggctag aggatccggc ctcggcctct gcataaataa      60
aaaaaattag tcagccatga gcttggccca ttgcatacgt tgtatccata tcataatatg     120
tacatttata ttggctcatg tccaacatta ccgccatgtt gacattgatt attgactagt     180
tattaatagt aatcaattac ggggtcatta gttcatagcc catatatgga gttccgcgtt     240
acataactta cggtaaatgg cccgcctggc tgaccgccca acgacccccg cccattgacg     300
tcaataatga cgtatgttcc catagtaacg ccaataggga cttt ccattg acgtcaatgg     360 gtggagtatt tacggtaaac tgcccacttg gcagtacatc aagtgtatca tatgccaagt     420 acgccccta ttgacgtcaa tgacggtaaa tggcccgcct ggcattatgc ccagtacatg     480
accttatggg actttcctac ttggcagtac atctacgtat tagtcatcgc tattaccatg     540
gtgatgcggt tttggcagta catcaatggg cgtggatagc ggtttgactc acggggattt     600
ccaagtctcc accccattga cgtcaatggg agtttgtttt ggcaccaaaa tcaacgggac     660
tttccaaaat gtcgtaacaa ctccgcccca ttgacgcaaa tgggcggtag gcgtgtacgg     720
```

```
tgggaggtct atataagcag agctcgttta gtgaaccgtc agatcgcctg gagacgccat    780
ccacgctgtt ttgacctcca tagaagacac cgggaccgat ccagcctccc ctcgaagctt    840
acatgtggta ccgagctcgg atcctgagaa cttcagggtg agtctatggg acccttgatg    900
ttttctttcc ccttcttttc tatggttaag ttcatgtcat aggaagggga gaagtaacag    960
ggtacacata ttgaccaaat cagggtaatt ttgcatttgt aattttaaaa aatgctttct   1020
tcttttaata tacttttttg tttatcttat ttctaatact ttccctaatc tctttctttc   1080
agggcaataa tgatacaatg tatcatgcct ctttgcacca ttctaaagaa taacagtgat   1140
aatttctggg ttaaggcaat agcaatattt ctgcatataa atatttctgc atataaattg   1200
taactgatgt aagaggtttc atattgctaa tagcagctac aatccagcta ccattctgct   1260
tttattttat ggttgggata aggctggatt attctgagtc caagctaggc ccttttgcta   1320
atcatgttca tacctcttat cttcctccca cagctcctgg gcaacgtgct ggtctgtgtg   1380
ctggcccatc actttggcaa agcacgtgag atctgaattc aacagagatc gatctgtttc   1440
cttgacacta tgaagtgcct tttgtactta gccttttat tcattgggt gaattgcaag    1500
ttcaccatag ttttccaca caaccaaaaa ggaaactgga aaaatgttcc ttctaattac    1560
cattattgcc cgtcaagctc agatttaaat tggcataatg acttaatagg cacagccata   1620
caagtcaaaa tgcccaagag tcacaaggct attcaagcag acggttggat gtgtcatgct   1680
tccaaatggg tcactacttg tgatttccgc tggtatggac cgaagtatat aacacagtcc   1740
atccgatcct tcactccatc tgtagaacaa tgcaaggaaa gcattgaaca acgaaacaa    1800
ggaacttggc tgaatccagg cttccctcct caaagttgtg gatatgcaac tgtgacggat   1860
gccgaagcag tgattgtcca ggtgactcct caccatgtgc tggttgatga atacacagga   1920
gaatgggttg attcacagtt catcaacgga aaatgcagca attacatatg ccccactgtc   1980
cataactcta caacctggca ttctgactat aaggtcaaag ggctatgtga ttctaacctc   2040
atttccatgg acatcaccct cttctcagag gacgagagc tatcatccct gggaaaggag    2100
ggcacagggt tcagaagtaa ctactttgct tatgaaactg gaggcaaggc ctgcaaaatg   2160
caatactgca gcattgggg agtcagactc ccatcaggtg tctggttcga gatggctgat    2220
aaggatctct ttgctgcagc cagattccct gaatgcccag aagggtcaag tatctctgct   2280
ccatctcaga cctcagtgga tgtaagtcta attcaggacg ttgagaggat cttggattat   2340
tccctctgcc aagaaacctg gagcaaaatc agagcgggtc ttccaatctc tccagtggat   2400
ctcagctatc ttgctcctaa aaacccagga accggtcctg ctttcaccat aatcaatggt   2460
accctaaaat actttgagac cagatacatc agagtcgata ttgctgctcc aatcctctca   2520
agaatggtcg gaatgatcag tggaactacc acagaaaggg aactgtggga tgactgggca   2580
ccatatgaag acgtggaaat tggacccaat ggagttctga ggaccagttc aggatataag   2640
tttcctttat acatgattgg acatggtatg ttggactccg atcttcatct tagctcaaag   2700
gctcaggtgt tcgaacatcc tcacattcaa gacgctgctt cgcaacttcc tgatgatgag   2760
agtttatttt ttggtgatac tgggctatcc aaaaatccaa tcgagcttgt agaaggttgg   2820
ttcagtagtt ggaaaagctc tattgcctct tttttcttta tcatagggtt aatcattgga   2880
ctattcttgg ttctccgagt tggtatccat cttttgcatta aattaaagca caccaagaaa   2940
agacagattt atacagacat agagatgaac cgacttggaa agtaactcaa atcctgcaca   3000
acagattctt catgtttgga ccaaatcaac ttgtgatacc atgctcaaag aggcctcaat   3060
tatatttgag ttttaatttt ttatggaatt caccccacca gtgcaggctg cctatcagaa   3120
```

```
agtggtggct ggtgtggcta atgccctggc ccacaagttt cactaagctc gcttccttgc    3180
tgtccaattt ctattaaagg ttccttggtt ccctaagtcc aactactaaa ctggggata    3240 ttatgaaggg ccttgagcat ctggattctg cctaataaaa aacatttatt ttcattgcaa   3300
tgatgtattt aaattatttc tgaatatttt actaaaaagg gaatgtggga ggtcagtgca   3360
tttaaaacat aaagaaatga agagctagtt caaaccttgg gaaaatacac tatatcttaa   3420
actccatgaa agaaggtgag gctgcaaaca gctaatgcac attggcaaca gccctgatgc   3480
ctatgcctta ttcatccctc agaaaaggat tcaagtagag gcttgatttg gaggttaaag   3540
tttggctatg ctgtatttta cattacttat tgttttagct gtcctcatga atgtcttttc   3600
actacccatt tgcttatcct gcatctctca gccttgactc cactcagttc tcttgcttag   3660
agataccacc tttcccctga agtgttcctt ccatgtttta cggcgagatg gtttctcctc   3720
gcctggccac tcagccttag ttgtctctgt tgtcttatag aggtctactt gaagaaggaa   3780
aaacaggggg catggtttga ctgtcctgtg agcccttctt ccctgcctcc cccactcaca   3840
gtgacccgga atccctcgac atggcagtct agcactagtg cggccgcaga tctgcttcct   3900
cgctcactga ctcgctgcgc tcggtcgttc ggctgcggcg agcggtatca gctcactcaa   3960
aggcggtaat acggttatcc acagaatcag gggataacgc aggaaagaac atgtgagcaa   4020
aaggccagca aaaggccagg aaccgtaaaa aggccgcgtt gctggcgttt ttccataggc   4080 tccgccccc tgacgagcat cacaaaaatc gacgctcaag tcagaggtgg cgaaacccga    4140
caggactata aagataccag gcgtttcccc ctggaagctc cctcgtgcgc tctcctgttc   4200
cgaccctgcc gcttaccgga tacctgtccg cctttctccc ttcgggaagc gtggcgcttt   4260
ctcaatgctc acgctgtagg tatctcagtt cggtgtaggt cgttcgctcc aagctgggct   4320
gtgtgcacga accccccgtt cagcccgacc gctgcgcctt atccggtaac tatcgtcttg   4380
agtccaaccc ggtaagacac gacttatcgc cactggcagc agccactggt aacaggatta   4440
gcagagcgag gtatgtaggc ggtgctacag agttcttgaa gtggtggcct aactacggct   4500
acactagaag gacagtattt ggtatctgcg ctctgctgaa gccagttacc ttcggaaaaa   4560
gagttggtag ctcttgatcc ggcaaacaaa ccaccgctgg tagcggtggt ttttttgttt   4620
gcaagcagca gattacgcgc agaaaaaaag gatctcaaga agatcctttg atcttttcta   4680
cggggtctga cgctcagtgg aacgaaaact cacgttaagg gattttggtc atgagattat   4740
caaaaaggat cttcacctag atccttttaa attaaaaatg aagttttaaa tcaatctaaa   4800
gtatatatga gtaaacttgg tctgacagtt accaatgctt aatcagtgag gcacctatct   4860
cagcgatctg tctatttcgt tcatccatag ttgcctgact ccccgtcgtg tagataacta   4920
cgatacggga gggcttacca tctggcccca gtgctgcaat gataccgcga gacccacgct   4980
caccggctcc agatttatca gcaataaacc agccagccgg aagggccgag cgcagaagtg   5040
gtcctgcaac tttatccgcc tccatccagt ctattaattg ttgccgggaa gctagagtaa   5100
gtagttcgcc agttaatagt ttgcgcaacg ttgttgccat tgctacaggc atcgtggtgt   5160
cacgctcgtc gtttggtatg gcttcattca gctccggttc ccaacgatca aggcgagtta   5220
catgatcccc catgttgtgc aaaaaagcgg ttagctcctt cggtcctccg atcgttgtca   5280
gaagtaagtt ggccgcagtg ttatcactca tggttatggc agcactgcat aattctctta   5340
ctgtcatgcc atccgtaaga tgcttttctg tgactggtga gtactcaacc aagtcattct   5400
gagaatagtg tatgcggcga ccgagttgct cttgcccggc gtcaatacgg gataataccg   5460
```

```
cgccacatag cagaacttta aaagtgctca tcattggaaa acgttcttcg gggcgaaaac    5520
tctcaaggat cttaccgctg ttgagatcca gttcgatgta acccactcgt gcacccaact    5580
gatcttcagc atcttttact ttcaccagcg tttctgggtg agcaaaaaca ggaaggcaaa    5640
atgccgcaaa aaagggaata agggcgacac ggaaatgttg aatactcata ctcttccttt    5700
ttcaatatta ttgaagcatt tatcagggtt attgtctcat gagcggatac atatttgaat    5760
gtatttagaa aaataaacaa ataggggttc cgcgcacatt tccccgaaaa gtgccacctg    5820
acgt                                                                5824

<210> SEQ ID NO 7
<211> LENGTH: 127
<212> TYPE: DNA
<213> ORGANISM: adeno-associated virus 2

<400> SEQUENCE: 7
cgcgctcgct cgctcactga ggccgcccgg gcaaagcccg ggcgtcgggc gacctttggt      60
cgcccggcct cagtgagcga gcgagcgcgc agagagggag tggccaactc catcactagg     120
ggttcct                                                              127

<210> SEQ ID NO 8
<211> LENGTH: 123
<212> TYPE: DNA
<213> ORGANISM: adeno-associated virus 2

<400> SEQUENCE: 8
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gag                                                                  123

<210> SEQ ID NO 9
<211> LENGTH: 103
<212> TYPE: DNA
<213> ORGANISM: Artificial Sequence
<220> FEATURE:
<223> OTHER INFORMATION: Synthesized in laboratory

<400> SEQUENCE: 9
cgcgctcgct cgctcactga ggccgcccgg gcaaagcccg ggcgtcgggc gacctttggt      60
cgcccggcct cagtgagcga gcgagcgcgc agagagggag tgg                      103
```